(12) United States Patent
Corso et al.

(10) Patent No.: US 6,956,207 B2
(45) Date of Patent: Oct. 18, 2005

(54) SEPARATION MEDIA, MULTIPLE ELECTROSPRAY NOZZLE SYSTEM AND METHOD

(75) Inventors: Thomas N. Corso, Lansing, NY (US); Gary A. Schultz, Ithaca, NY (US); Simon J. Prosser, Ithaca, NY (US); Xian Huang, Ithaca, NY (US)

(73) Assignee: Advion BioScience, Inc., Ithaca, NY (US)

( * ) Notice: Subject to any disclaimer, the term of this patent is extended or adjusted under 35 U.S.C. 154(b) by 251 days.

(21) Appl. No.: 10/405,689

(22) Filed: Apr. 1, 2003

(65) Prior Publication Data

US 2003/0201390 A1 Oct. 30, 2003

Related U.S. Application Data

(62) Division of application No. 09/764,698, filed on Jan. 18, 2001, now Pat. No. 6,596,988.
(60) Provisional application No. 60/176,605, filed on Jan. 18, 2000.

(51) Int. Cl.[7] .......................... H01J 49/00; B01D 59/44
(52) U.S. Cl. ........................................ 250/288; 250/281
(58) Field of Search ................................ 250/281, 282, 250/288, 423 R; 210/198.2, 243, 656, 748

(56) References Cited

U.S. PATENT DOCUMENTS 3,150,442 A    9/1964   Straw et al.

(Continued)

FOREIGN PATENT DOCUMENTS

DE    43 18 407 A1    6/1993

(Continued)

OTHER PUBLICATIONS

Beavis et al., "Off–Line Coupling of a Microbore High–Performance Liquid Chromatograph to a Secondary Ion Time–of–Flight Mass Spectrometer," *Anal. Chem.*, 62:1259–1264 (1990).

(Continued)

*Primary Examiner*—John R. Lee
*Assistant Examiner*—David A. Vanore
(74) *Attorney, Agent, or Firm*—Nixon Peabody LLP

(57) ABSTRACT

A microfabricated silicon chip with a separation material, such as in situ prepared porous polymer monoliths in its microchannels is disclosed. The polymer monoliths are liquid-permeable and serve as microcolumns for liquid chromatography, which are prepared by in situ radical polymerization of a mixture containing vinyl monomers and solvents (porogen) in the microchannels. A method and system are disclosed to generate one or more electrospray plumes from one or more nozzles that provide an ion intensity as measured by a mass spectrometer that is approximately proportional to the number of electrospray plumes formed for analyses contained within the fluid. A plurality of electrospray devices can be used in the form of an array of miniaturized separate electrospray devices for the purpose of generating multiple electrospray plumes from multiple nozzles for the same fluid for analysis. This invention dramatically increases the sensitivity of microchip electrospray devices compared to prior disclosed systems and methods. The silicon chip having the packed microchannels disclosed herein finds application in coupling with mass spectrometry for sample analysis. Also disclosed is a separation block having multiple through-substrate channels filled with a separation material such as polymer monolith which can be stacked in multiple blocks for sequential two-dimensional chromatographic separation and integrated with the electrospray device.

9 Claims, 64 Drawing Sheets

U.S. PATENT DOCUMENTS

| | | |
|---|---|---|
| 3,538,744 A | 11/1970 | Karasek et al. |
| 3,669,881 A | 6/1972 | Cremer et al. |
| 3,738,759 A | 6/1973 | Dittrich et al. |
| 3,915,652 A | 10/1975 | Natelson |
| 3,921,916 A | 11/1975 | Bassous |
| 4,007,464 A | 2/1977 | Bassous et al. |
| 4,056,324 A | 11/1977 | Göhde |
| 4,092,166 A | 5/1978 | Olsen et al. |
| 4,209,696 A | 6/1980 | Fite |
| 4,356,722 A | 11/1982 | Bunce et al. |
| 4,366,118 A | 12/1982 | Bunce et al. |
| 4,369,664 A | 1/1983 | Bunce et al. |
| 4,403,234 A | 9/1983 | Miura et al. |
| 4,437,103 A | 3/1984 | Ikeda |
| 4,459,267 A | 7/1984 | Bunce et al. |
| 4,480,259 A | 10/1984 | Kruger et al. |
| 4,489,259 A | 12/1984 | White et al. |
| 4,490,728 A | 12/1984 | Vaught et al. |
| 4,590,482 A | 5/1986 | Hay et al. |
| 4,593,728 A | 6/1986 | Whitehead et al. |
| 4,683,042 A | 7/1987 | Scott |
| 4,708,782 A | 11/1987 | Andresen et al. |
| 4,728,392 A | 3/1988 | Miura et al. |
| 4,733,823 A | 3/1988 | Waggener et al. |
| 4,842,701 A | 6/1989 | Smith et al. |
| 4,879,097 A | 11/1989 | Whitehead et al. |
| 4,891,120 A | 1/1990 | Sethi et al. |
| 4,908,112 A | 3/1990 | Pace |
| 4,983,038 A | 1/1991 | Ohki et al. |
| 4,999,493 A | 3/1991 | Allen et al. |
| 5,015,845 A | 5/1991 | Allen et al. |
| 5,110,745 A | 5/1992 | Kricka et al. |
| 5,126,022 A | 6/1992 | Soane et al. |
| 5,132,012 A | 7/1992 | Miura et al. |
| 5,162,650 A | 11/1992 | Bier et al. |
| 5,180,480 A | 1/1993 | Manz |
| 5,182,366 A | 1/1993 | Huebner et al. |
| 5,245,185 A | 9/1993 | Busch et al. |
| 5,269,900 A | 12/1993 | Jorgenson et al. |
| 5,283,036 A | 2/1994 | Hofmann et al. |
| 5,294,426 A | 3/1994 | Sekine et al. |
| 5,296,114 A | 3/1994 | Manz |
| 5,296,375 A | 3/1994 | Kricka et al. |
| 5,302,533 A | 4/1994 | Kricka |
| 5,304,487 A | 4/1994 | Wilding et al. |
| 5,306,621 A | 4/1994 | Kricka |
| 5,316,680 A | 5/1994 | Frechet et al. |
| 5,328,578 A | 7/1994 | Gordon |
| 5,331,159 A | 7/1994 | Apffel, Jr. et al. |
| 5,332,481 A | 7/1994 | Guttman |
| 5,334,310 A | 8/1994 | Frechet |
| 5,338,427 A | 8/1994 | Shartle et al. |
| 5,349,186 A | 9/1994 | Ikonomou et al. |
| 5,374,834 A | 12/1994 | Geis et al. |
| 5,376,252 A | 12/1994 | Ekström et al. |
| 5,387,329 A | 2/1995 | Foos et al. |
| 5,401,376 A | 3/1995 | Foos et al. |
| 5,401,963 A | 3/1995 | Sittler |
| 5,415,841 A | 5/1995 | Dovichi et al. |
| 5,421,980 A | 6/1995 | Guttman |
| 5,423,964 A | 6/1995 | Smith et al. |
| 5,427,946 A | 6/1995 | Kricka et al. |
| 5,429,734 A | 7/1995 | Gajar et al. |
| 5,431,807 A | 7/1995 | Frechet et al. |
| 5,445,324 A | 8/1995 | Berry et al. |
| 5,453,185 A | 9/1995 | Frechet |
| 5,481,110 A | 1/1996 | Krishnaswamy et al. |
| 5,486,335 A | 1/1996 | Wilding et al. |
| 5,493,115 A | 2/1996 | Deinzer et al. |
| 5,495,108 A | 2/1996 | Apffel, Jr. et al. |
| 5,498,392 A | 3/1996 | Wilding et al. |
| 5,501,883 A | 3/1996 | Ishikawa et al. |
| 5,501,893 A | 3/1996 | Laermer et al. |
| 5,505,832 A | 4/1996 | Laukien et al. |
| 5,512,131 A | 4/1996 | Kumar et al. |
| 5,512,451 A | 4/1996 | Kricka |
| 5,523,566 A | 6/1996 | Fuerstenau et al. |
| 5,536,939 A | 7/1996 | Freidhoff et al. |
| 5,541,408 A | 7/1996 | Sittler |
| 5,563,639 A | 10/1996 | Cameron et al. |
| 5,572,023 A | 11/1996 | Caprioli |
| 5,608,217 A | 3/1997 | Franzen et al. |
| 5,640,010 A | 6/1997 | Twerenbold |
| 5,641,400 A | 6/1997 | Kaltenbach et al. |
| 5,644,131 A | 7/1997 | Hansen |
| 5,647,979 A | 7/1997 | Liao et al. |
| 5,652,427 A | 7/1997 | Whitehouse et al. |
| 5,705,813 A | 1/1998 | Apffel et al. |
| 5,716,825 A | 2/1998 | Hancock et al. |
| 5,747,815 A | 5/1998 | Young et al. |
| 5,750,988 A | 5/1998 | Apffel et al. |
| 5,779,868 A | 7/1998 | Parce et al. |
| 5,789,746 A | 8/1998 | Kato et al. |
| 5,800,692 A | 9/1998 | Naylor et al. |
| 5,804,022 A | 9/1998 | Kaltenbach et al. |
| 5,856,082 A | 1/1999 | Aebersold |
| 5,872,010 A | 2/1999 | Karger et al. |
| 5,876,957 A | 3/1999 | Douglas et al. |
| 5,877,495 A | 3/1999 | Takada et al. |
| 5,917,184 A | 6/1999 | Carson et al. |
| 5,917,185 A | 6/1999 | Yeung et al. |
| 5,969,351 A | 10/1999 | Nabeshima et al. |
| 5,969,353 A | 10/1999 | Hsieh |
| 5,972,187 A | 10/1999 | Parce et al. |
| 5,993,633 A | 11/1999 | Smith et al. |
| 5,994,696 A | 11/1999 | Tai et al. |
| 6,005,245 A | 12/1999 | Sakairi et al. |
| 6,007,775 A | 12/1999 | Yager |
| 6,032,876 A | 3/2000 | Bertsch et al. |
| 6,060,705 A | 5/2000 | Whitehouse et al. |
| 6,066,848 A | 5/2000 | Kassel et al. |
| 6,068,749 A | 5/2000 | Karger et al. |
| 6,110,343 A | 8/2000 | Ramsey et al. |
| 6,114,693 A | 9/2000 | Hirabayashi et al. |
| 6,171,875 B1 | 1/2001 | Silverbrook |
| 6,245,227 B1 | 6/2001 | Moon et al. |
| 6,394,942 B2 | 5/2002 | Moon et al. |
| 6,417,510 B2 | 7/2002 | Moon et al. |
| 6,432,311 B2 | 8/2002 | Moon et al. |
| 6,454,938 B2 | 9/2002 | Moon et al. |
| 6,461,516 B2 | 10/2002 | Moon et al. |
| 6,464,866 B2 | 10/2002 | Moon et al. |
| 6,596,988 B2 * | 7/2003 | Corso et al. ............... 250/288 |
| 6,627,882 B2 * | 9/2003 | Schultz et al. ............. 250/288 |
| 6,633,031 B1 * | 10/2003 | Schultz et al. ............. 250/288 |
| 6,723,985 B2 * | 4/2004 | Schultz et al. ............. 250/288 |
| 6,768,107 B2 * | 7/2004 | Schultz et al. ............. 250/288 |
| 6,787,766 B2 * | 9/2004 | Schultz et al. ............. 250/288 |
| 6,811,689 B2 * | 11/2004 | Zhang et al. ............ 210/198.2 |
| 6,814,870 B2 * | 11/2004 | Zhang et al. ............... 210/656 |
| 6,822,231 B2 * | 11/2004 | Schultz et al. ............. 250/288 |
| 2001/0001455 A1 | 5/2001 | Moon et al. |
| 2001/0001460 A1 | 5/2001 | Moon et al. |
| 2002/0123153 A1 | 9/2002 | Moon et al. |
| 2002/0158027 A1 | 10/2002 | Moon et al. |

FOREIGN PATENT DOCUMENTS

| | | |
|---|---|---|
| EP | 0 677 322 A2 | 10/1995 |
| EP | 677332 A2 | 10/1995 |
| EP | 259796 B1 | 1/1996 |
| EP | 692713 A1 | 1/1996 |

| | | |
|---|---|---|
| EP | 0 637 998 B1 | 7/1996 |
| EP | 0 639 223 B1 | 7/1996 |
| EP | 565027 B1 | 3/1997 |
| EP | 0 860858 A1 | 8/1998 |
| EP | 588952 B1 | 9/1999 |
| EP | 0 964428 A2 | 12/1999 |
| EP | 0 966022 A2 | 12/1999 |
| GB | 2260282 | 4/1993 |
| GB | 2287356 A | 9/1995 |
| WO | WO 92/03720 | 3/1992 |
| WO | WO 93/22053 | 11/1993 |
| WO | WO 93/22055 | 11/1993 |
| WO | WO 96/04547 | 2/1996 |
| WO | WO 96/14933 | 5/1996 |
| WO | WO 96/14934 | 5/1996 |
| WO | WO 96/15269 | 5/1996 |
| WO | WO 97/04297 | 2/1997 |

OTHER PUBLICATIONS

Burggraf et al., "Synchronized Cyclic Capillary Electrophoresis—A Novel Approach to Ion Separations in Solution," *J. High Resol. Chromatogr.,* 16:594–596 (1993).

Cheng et al., "Chip PCR. II. Investigation of Different PCR Amplification Systems in Microfabricated Silicon–Glass Chips," *Nucleic Acids Res.,* 24(2):380–385 (1996).

Chu et al., "Affinity Capillary Electrophoresis—Mass Spectrometry for Screening Combinatorial Libraries," *J. Am. Chem. Soc.,* pp. 7827–7835 (1996).

Cowen et al., "An On–Chip Miniature Liquid Chromatography System: Design, Construction and Characterization," *Micro Total Analysis Systems,* pp. 295–298 (1995).

Davis et al., "A Microscale Electroscopy Interface for On–Line, Capillary Liquid Chromatography/Tandem Mass Spectrometry of Complex Peptide Mixtures," *Anal. Chem.,* 67:4549–4556 (1995).

Deml et al., "Electric Sample Splitter for Capillary Zone Electrophoresis," *J. Chromatogr.,* 320:159–165 (1985).

Doherty et al., "Rapid On–Line Analysis Using a Micromachined Gas Chromatograph Coupled to a Bench–Top Quadrupole Mass Spectrometer," *LC–GC,* 12(11):846–850 (1994).

Effenhauser et al., "High–Speed Separation of Antisense Oligonucleotides on a Micromachined Capillary Electrophoresis Device," *Anal. Chem.,* 66:2949–2953 (1994).

Effenhauser et al., "Glass Chips for High–Speed Capillary Electrophoresis Separations with Submicrometer Plate Heights," *Anal. Chem.,* 65:2637–2642 (1993).

Effenhauser et al., "Manipulation of Sample Fractions on a Capillary Electrophoresis Chip," *Anal. Chem.,* 67(13):2284–2287 (1995).

Elwenspoek et al., "Silicon Microstructures for Fluid Handling," *Analysis Magazine,* pp. 1–4 (1994).

Emmett et al., "Micro–Electrospray Mass Spectrometry: Ultra–High–Sensitivity Analysis of Peptides and Proteins," *J. Am. Soc. Mass Spectrom.,* 5:605–613 (1994).

Fan et al., "Micromachining of Capillary Electrophoresis Injectors and Separators on Glass Chips and Evaluation of Flow at Capillary Intersections," *Anal. Chem.,* 66:177–184 (1994).

Fang et al., "On–Line Time–of–Flight Mass Spectrometric Analysis of Peptides Separated by Capillary Electrophoresis," *Anal. Chem.,* 66:3696–3701 (1994).

Figueroa et al., "High–Performance Immobilized–Metal Affinity Chromatography of Proteins on Iminodiacetic Acid Silica–Based Bonded Phases," *J. Chromatogr.* 371:335–352 (1986).

Harrison et al., "Rapid Separation of Fluorescein Derivatives Using a Micromachined Capillary Electrophoresis System," *Analytica Chimica Acta,* 283:361–366 (1993).

Harrison et al., "Capillary Electrophoresis and Sample Injection Systems Integrated on a Planar Glass Chip," *Anal. Chem.* 64(17):1926–1932 (1992).

Harrison et al., "Towards Miniaturized Electrophoresis and Chemical Analysis Systems on Silicon: An Alternative to Chemical Sensors," *Sensors and Actuators B,* 10:107–116 (1993).

Jacobson et al., "Microchip Electrophoresis With Sample Stacking," *Electrophoresis,* 16:481–486 (1995).

Jacobson et al., "Fused Quartz Substrates for Microchip Electrophoresis," *Anal. Chem.,* 67:2059–2063 (1996).

Jacobson et al., "Microchip Capillary Electrophoresis with an Integrated Postcolumn Reactor," *Anal. Chem.,* 66:3472–3476 (1994).

Jacobson et al., "Effects of Injection Schemes and Column Geometry on the Performance of Microchip Electrophoresis Devices," *Anal. Chem.,* 66:1107–1113 (1994).

Jacobson et al., "Integrated Microdevice for DNA Restriction Fragment Analysis," *Anal. Chem.,* 68(5):720–723 (1996).

Jacobson et al., "Precolumn Reactions with Electrophoretic Analysis Integrated on a Microchip," *Anal. Chem.,* 66:4127–4132 (1994).

Jansson et al., "Micro Vials on a Silicon Wafer for Sample Introduction in Capillary Electrophoresis," *J. Chromatogr.,* 626:310–314 (1992).

Ko et al., "Semiconductor Integrated Circuit Technology and Micromachining," pp. 109–168—undated.

Körner et al., "Nano Electrospray Combined with a Quadrupole Ion Trap for the Analysis of Peptides and Protein Digests," *J. Am. Soc. Mass. Spectrom.,* 7:150–156 (1996).

Koutny et al., "Microchip Electrophoretic Immunoassay for Serum Cortisol," *Anal. Chem.,* 68:18–22 (1996).

Kriger et al., "Durable Gold–Coated Fused Silica Capillaries for Use in Electrospray Mass Spectrometry," *Anal. Chem.,* 67:385–389 (1995).

Manz et al., "Micromachining of Monocrystalline Silicon and Glass for Chemical Analysis Systems," *Trends in Anal Chem.,* 10(5):144–149 (1991).

Manz et al., "Planar Chips Technology for Miniaturization and Integration of Separation Techniques Into Monitoring Systems," *J. Chromatogr.,* 593:253–258 (1992).

Manz et al., "Planar Chips Technology for Miniaturization of Separation Systems: A Developing Perspective in Chemical Monitoring," *Advances in Chromatography,* pp. 1–66 (1993).

Manz et al., "Design of an Open–Tubular Column Liquid Chromatograph Using Silicon Chip Technology," *Sensors and Actuators,* B1:249–255 (1990).

Manz et al., "Miniaturization of Separation Techniques Using Planar Chip Technology," *J. High Resol. Chromatogr.,* 16:433–436 (1993).

Manz et al., "Planar Chip Technology for Capillary Electrophoresis," *Fresenius J. Anal. Chem.,* 348:567–571 (1994).

Moore et al., "Microchip Separations of Neutral Species Via Micellar Electrokinetic Capillary Chromatography," *Anal. Chem.,* 67:4184–4189 (1995).

Nichols et al., "CE–MS for Industrial Applications Using a Liquid Junction With Ion–Spray and CF–FAB Mass Spectrometry," *LC–GC,* 10(9):676–686 (1992).

Ocvirk et al., "High Performance Liquid Chromatography Partially Integrated Onto a Silicon Chip," Anal. Meth. Instrumen., 2(2):74–82 (1995).

Olivares et al., "On–Line Mass Spectrometric Detection for Capillary Zone Electrophoresis," Anal. Chem., 59:1230–1232 (1987).

Overton et al., "Development of a Temperature Programmed Microchip, High Resolution Gas Chromatograph/Mass Spectrometer for Volatile Organic Compound Analysis," pp. 395–398.

Petersen, "Biomedical Applications of MEMS," IEEE, pp. 239–242 (1996).

Raymond et al., "Continuous Sample Pretreatment Using a Free–Flow Electrophoresis Device Integrated Onto a Silicon Chip," Anal. Chem., 66:2858–2865 (1994).

Roeraade, "Nano–Sized Systems for Bioanalysis," Eighth International Symposium on High Performance Capillary Electrophoresis, pp. 3, 19, 68 (1996) (abstract).

Seiler et al., "Electroosmotic Pumping and Valveless Control of Fluid Flow Within a Manifold of Capillaries on a Glass Chip," Anal. Chem., 66(20):3485–3491 (1994).

Seiler et al., "Planar Glass Chips for Capillary Electrophoresis: Repetitive Sample Injection, Quantitation, and Separation Efficiency," Anal. Chem., 65:1481–1488 (1993).

Shoffner et al., "Chip PCR. I. Surface Passivation of Microfabricated Silicon–Glass Chips for PCR," Nucleic Acids Res., 24(2):375–379 (1996).

Sjölander et al., "Integrated Fluid Handling System for Biomolecular Interaction Analysis," Anal. Chem., 63(20):2338–2345 (1991).

Smith et al., "Improved Electrospray Ionization Interface for Capillary Zone Electrophoresis–Mass Spectrometry," Anal. Chem., 60:1948–1952 (1988).

Valaskovic et al., "Attomole–Sensitivity Electrospray Source for Large–Molecule Mass Spectrometry," Anal. Chem., 67:3802–3805 (1995).

Wahl et al., "Sheathless Capillary Electrophoresis–Electrospray Ionization Mass–Spectrometry Using 10 µm I.D. Capillaries: Analyses of Tryptic Digests of Cytochrome c," J. Chromatogr. A. 659:217–222 (1994).

Whitehouse et al., "Electrospray Interface for Liquid Chromatographs and Mass Spectrometers," Anal. Chem., 57:675–679 (1985).

Woolley et al., "Ultra–High–Speed DNA Sequencing Using Capillary Electrophoresis Chips," Anal. Chem., 67:3676–3680 (1995).

Woolley et al., "Ultra–High–Speed DNA Fragment Separations Using Microfabricated Capillary Array Electrophoresis Chips," Proc. Natl. Acad. Sci. USA, 91:11348–11352 (1994).

Yoshida et al., "Direct Measurement of Mass Fragmentograms for Eluents From a Micro–Liquid Chromatograph Using an Improved Nebulizing Interface," J. HRC&CC, 3:16–20 (1980).

Smith et al., "New Developments in Microscale Separations and Mass Spectrometry for Biomonitoring: Capillary Electrophoresis and Electrospray Ionization Mass Spectrometry," J. Toxicol. and Environ. Health, 40:147–158 (1993).

Wilm et al., "Analytical Properties of the Nanoelectrospray Ion Source," Anal. Chem., 68:1–8 (1996).

Figeys et al., "A Microfabricated Device for Rapid Protein Identification by Microelectrospray Ion Trap Mass Spectrometry," Anal. Chem., 69:3153–3160 (1997).

Vanhouttte et al., "Development of a Nanoscale Liquid Chromatography/Electrospray Mass Spectrometry Methodology for the Detection and Identification of DNA Adducts," Anal. Chem., 69:3161–3168 (1997).

Andren et al., "Micro–Electrospray: Zeptomole/Attomole per Microlitter Sensitivity for Peptides," J. Am. Soc. Mass Spectrom., 5:867–869 (1994).

Angell et al., "Silicon Micromechanical Devices," Scientific American, 248(4):44–55 (1983).

Beavis et al., "Automated Dry Fraction Collection for Microbore High–Performance Liquid Chromatography–Mass Spectrometry," J. Chromatography, 359:489–497 (1986).

Snyder, Introduction to Modern Liquid Chromatography, John Wiley & Sons, Inc., pp. 270–272 and 277–278 (1979).

Knox, "Theoretical Aspects of LC with Packed and Open Small–Bore Columns," Journal of Chromatographic Science 18:453–461 (1980).

Alexander et al., "Development of a Nano–electrospray Mass Spectrometry Source for Nanoscale Liquid Chromatography and Sheathless Capillary Electrophoresis," Rapid Commun. Mass Spectrom., 12:1187–1191 (1998).

Harrison et al., "Micromachining a Miniaturized Capillary Electrophoresis–Based Chemical Analysis System on a Chip," Science 261:895–897 (1993).

Jacobson et al., "High–Speed Separations on a Microchip," Anal. Chem. 66:1114–1118 (1994).

Jacobson et al., "Open Channel Electrochromatography on a Microchip," Anal. Chem. 66:2369–2373 (1994).

Kutter et al., "Integrated Microchip Device with Electrokinetically Controlled Solvent Mixing for Isocratic and Gradient Elution in Micellar Electrokinetic Chromatography," Anal. Chem. 69:5165–5171 (1997).

He et al., "Fabrication of Nanocolumns for Liquid Chromatography," Anal. Chem. 70:3790–3797 (1998).

Dole et al., "Molecular Beams of Macroions," The Journal of Chemical Physics 49:2240–2249 (1968).

Yamashita et al., "Electrospray Ion Source. Another Variation on the Free–Jet Theme," The Journal of Physical Chemistry 88(20):4451–4459 (1984).

David P.H. Smith, "The Electrohydrodynamic Atomization of Liquids," IEEE Transactions on Industry Applications IA–22(3):527–535 (1986).

Electrospray Ionization Mass Spectrometry: Fundamentals, Instrumentation, and Applications, ed. R.B. Cole, ISBN 0–471–14564–5, New York, New York:John Wiley & Sons, Inc., pp. 3–63 (1997).

Gale et al., "Small Volume and Low Flow–rate Electrospray Ionization Mass Spectrometry of Aqueous Samples," Rapid Commun. Mass Spectrom. 7:1017–1021 (1993).

Wilm et al., "Electrospray and Taylor–Cone Theory, Dole's Beam of Macromolecules at Last?" Intl. J. Mass Spectrom. Ion Processes 136:167–180 (1994).

Ramsey et al., "Generating Electrospray from Microchip Devices Using Electroosmotic Pumping," Anal. Chem. 69:1174–1178 (1997).

Xue et al., "Multichannel Microchip Electrospray Mass Spectrometry," *Anal. Chem.* 69:426–430 (1997).

Lee et al., "A MEMS Electrospray Nozzel for Mass Spectroscopy," *1997 Int. Conference on Solid State Sensors and Actuators,* Chicago, pp. 927–930 (Jun. 16–19, 1997).

Lee et al., "Polymer–Based Electrospray Chips for Mass Spectrometry," *Twelfth IEEE International Conference on Micro Electro Mechanical Systems,* Orlando, Florida, pp. 523–528 (1999).

Laermer et al., "Bosch Deep Silicon Etching: Improving Uniformity and Etch Rate for Advanced Mems Applications," *Twelfth IEEE International Conference on Micro Electro Mechanical Systems,* Orlando, Florida, pp. 211–216 (1999).

Peters et al., "Rigid Macroporous Polymer Monoliths," *Advanced Materials,* 11(14):1169–1181 (1999).

* cited by examiner

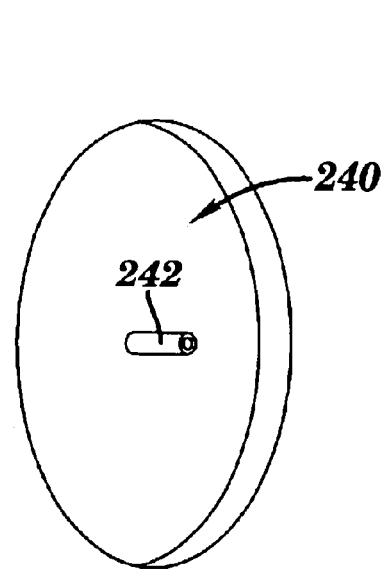 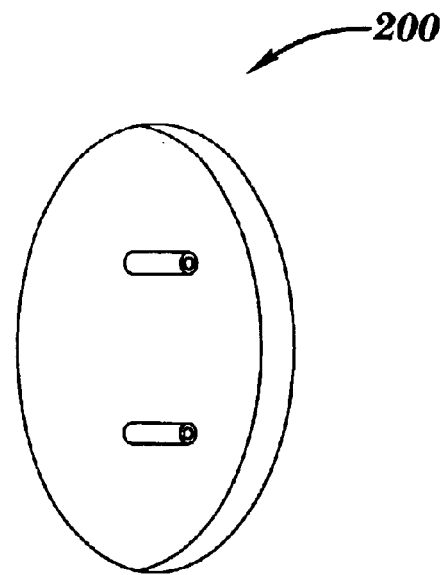
FIG. 1H      FIG. 1I
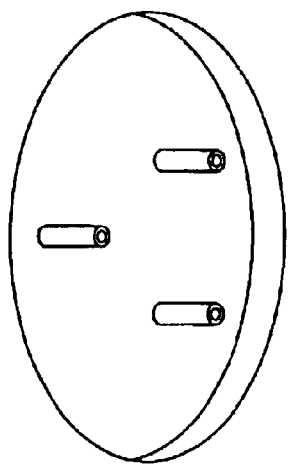 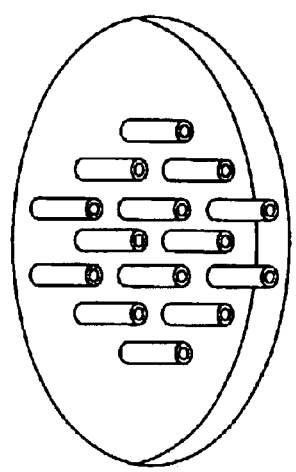
FIG. 1J      FIG. 1K

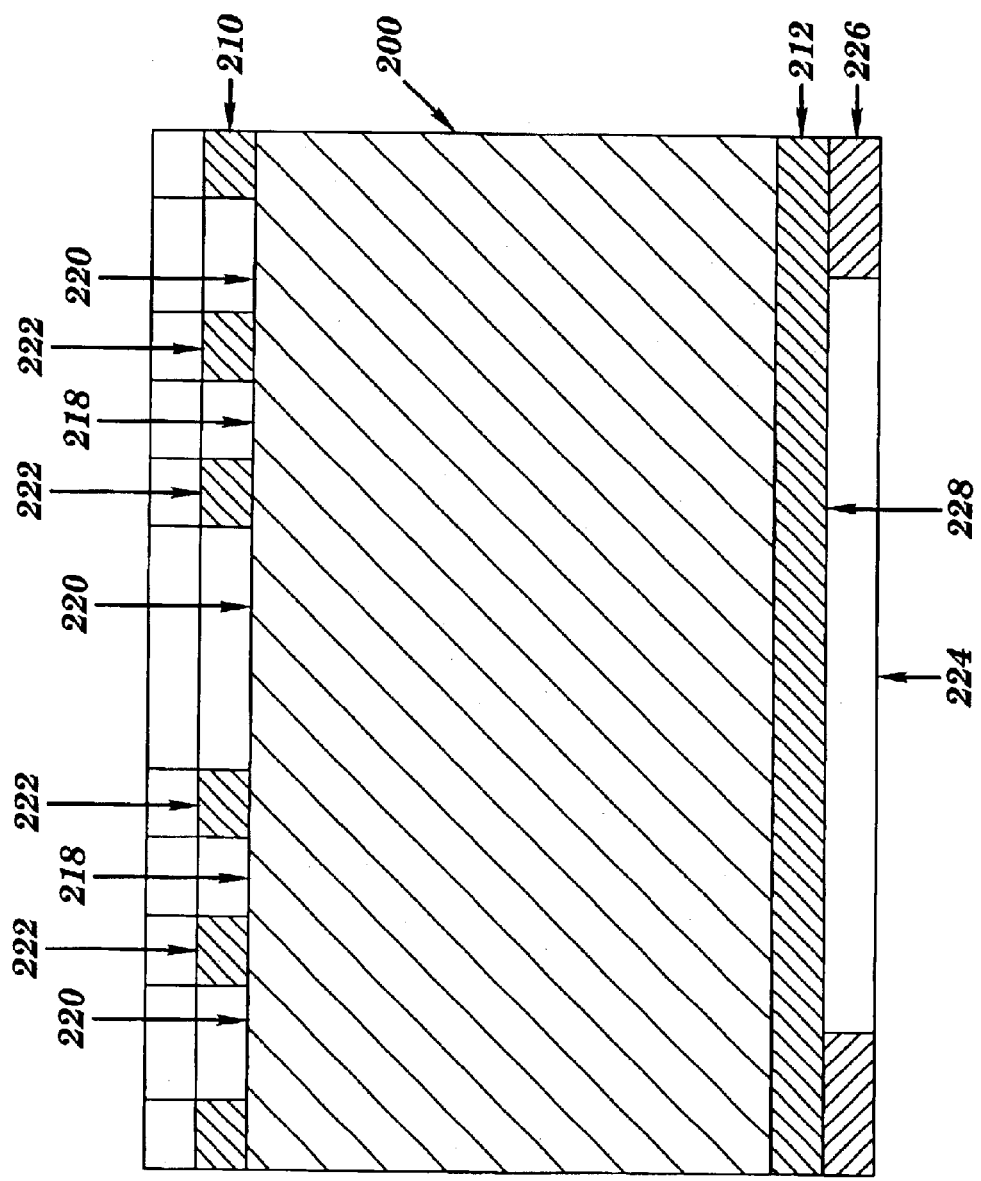

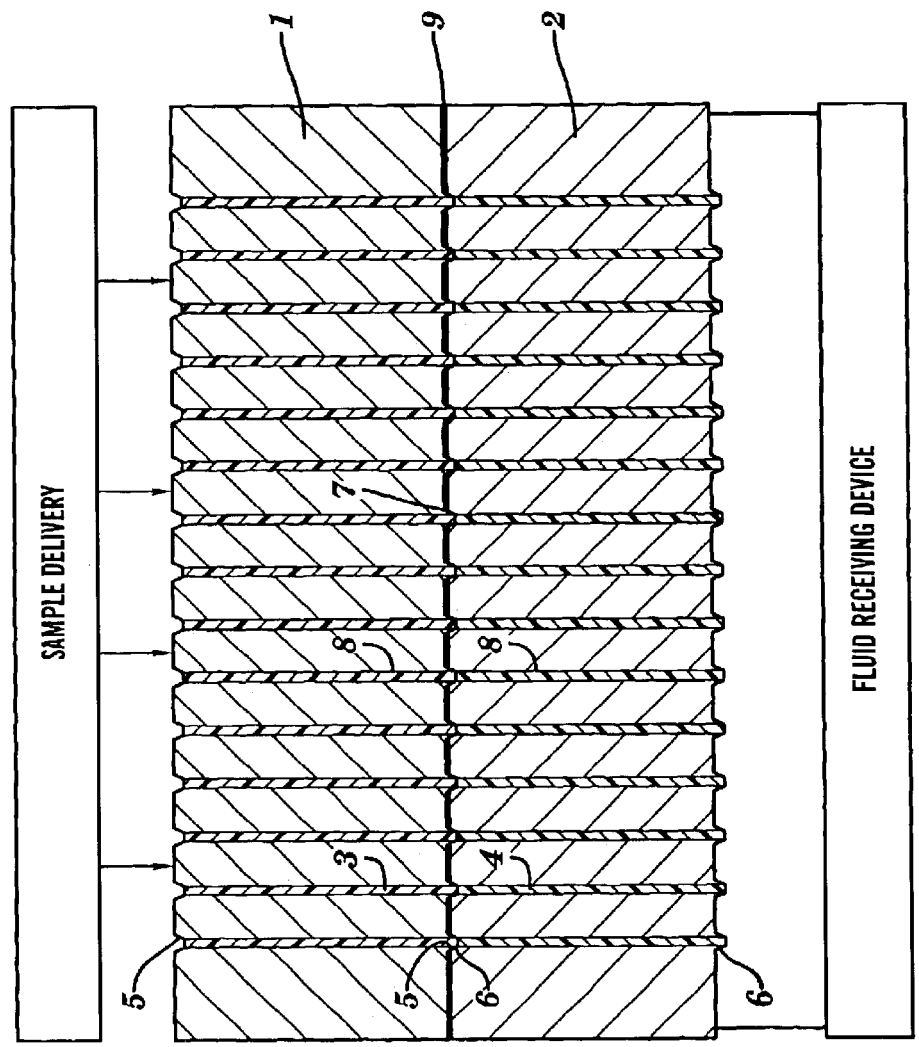

SEPARATION MEDIA, MULTIPLE ELECTROSPRAY NOZZLE SYSTEM AND METHOD

This application is a division of U.S. patent application Ser. No. 09/764,698, filed Jan. 18, 2001 now U.S. Pat. No. 6,596,988.

This application claims the benefit of U.S. Provisional Patent Application Ser. No. 60/176,605, filed Jan. 18, 2000, which is herein incorporated by reference in its entirety.

FIELD OF THE INVENTION

The present invention relates generally to an integrated miniaturized fluidic system fabricated using Micro-ElectroMechanical System (MEMS) technology, particularly to an integrated monolithic microfabricated device capable of generating multiple sprays from a single fluid stream and a separation material, preferably a porous monolithic polymer bed, for chromatographic separations.

BACKGROUND OF THE INVENTION

New trends in drug discovery and development are creating new demands on analytical techniques. For example, combinatorial chemistry is often employed to discover new lead compounds, or to create variations of a lead compound. Combinatorial chemistry techniques can generate thousands of compounds (combinatorial libraries) in a relatively short time (on the order of days to weeks). Testing such a large number of compounds for biological activity in a timely and efficient manner requires high-throughput screening methods which allow rapid evaluation of the characteristics of each candidate compound.

The quality of the combinatorial library and the compounds contained therein is used to assess the validity of the biological screening data. Confirmation that the correct molecular weight is identified for each compound or a statistically relevant number of compounds along with a measure of compound purity are two important measures of the quality of a combinatorial library. Compounds can be analytically characterized by removing a portion of solution from each well and injecting the contents into a separation device such as liquid chromatography or capillary electrophoresis instrument coupled to a mass spectrometer.

Development of viable screening methods for these new targets will often depend on the availability of rapid separation and analysis techniques for analyzing the results of assays. For example, an assay for potential toxic metabolites of a candidate drug would need to identify both the candidate drug and the metabolites of that candidate. An understanding of how a new compound is absorbed in the body and how it is metabolized can enable prediction of the likelihood for an increased therapeutic effect or lack thereof.

Given the enormous number of new compounds that are being generated daily, an improved system for identifying molecules of potential therapeutic value for drug discovery is also critically needed. Accordingly, there is a critical need for high-throughput screening and identification of compound-target reactions in order to identify potential drug candidates.

Liquid chromatography (LC) is a well-established analytical method for separating components of a fluid for subsequent analysis and/or identification. Traditionally, liquid chromatography utilizes a separation column, such as a cylindrical tube with dimensions 4.6 mm inner diameter by 25 cm length, filled with tightly packed particles of 5 $\mu$m diameter. More recently, particles of 3 $\mu$m diameter are being used in shorter length columns. The small particle size provides a large surface area that can be modified with various chemistries creating a stationary phase. A liquid eluent is pumped through the LC column at an optimized flow rate based on the column dimensions and particle size. This liquid eluent is referred to as the mobile phase. A volume of sample is injected into the mobile phase prior to the LC column. The analytes in the sample interact with the stationary phase based on the partition coefficients for each of the analytes. The partition coefficient is defined as the ratio of the time an analyte spends interacting with the stationary phase to the time spent interacting with the mobile phase. The longer an analyte interacts with the stationary phase, the higher the partition coefficient and the longer the analyte is retained on the LC column. The diffusion rate for an analyte through a mobile phase (mobile-phase mass transfer) also affects the partition coefficient. The mobile-phase mass transfer can be rate limiting in the performance of the separation column when it is greater than 2 $\mu$m (Knox, J. H. J. *J. Chromatogr. Sci.* 18:453–461 (1980)). Increases in chromatographic separation are achieved when using a smaller particle size as the stationary phase support.

The purpose of the LC column is to separate analytes such that a unique response for each analyte from a chosen detector can be acquired for a quantitative or qualitative measurement. The ability of a LC column to generate a separation is determined by the dimensions of the column and the particle size supporting the stationary phase. A measure of the ability of LC columns to separate a given analyte is referred to as the theoretical plate number N. The retention time of an analyte can be adjusted by varying the mobile phase composition and the partition coefficient for an analyte. Experimentation and a fundamental understanding of the partition coefficient for a given analyte determine which stationary phase is chosen.

To increase the throughput of LC analyses requires a reduction in the dimensions of the LC column and the stationary phase particle dimensions. Reducing the length of the LC column from 25 cm to 5 cm will result in a factor of 5 decrease in the retention time for an analyte. At the same time, the theoretical plates are reduced 5-fold. To maintain the theoretical plates of a 25 cm length column packed with 5 $\mu$m particles, a 5 cm column would need to be packed with 1 $\mu$m particles. However, the use of such small particles results in many technical challenges.

One of these technical challenges is the backpressure resulting from pushing the mobile phase through each of these columns. The backpressure is a measure of the pressure generated in a separation column, due to pumping a mobile phase at a given flow rate through the LC column. For example, the typical backpressure of a 4.6 mm inner diameter by 25 cm length column packed with 5 $\mu$m particles generates a backpressure of 100 bar at a flow rate of 1.0 mL/min. A 5 cm column packed with 1 $\mu$m particles generates a back pressure 5 times greater than a 25 cm column packed with 5 $\mu$m particles. Most commercially available LC pumps are limited to operating pressures less than 400 bar and thus using an LC column with these small particles is not feasible.

More recently, Fréchet in U.S. Pat. Nos. 5,334,310 and 5,453,185, which are each herein incorporated by reference in their entirety, describe the use of a continuous polymer bed formed by in situ polymerization of a monomer solution containing a porogen within a column. Many examples on the use of these continuous or monolithic polymer supports are available in the literature. Liao in U.S. Pat. No. 5,647,979 describes a similar use of a continuous polymer bed for reversed-phase chromatography and capillary electrochromatography in capillary columns.

Detection of analytes separated on an LC column has traditionally been accomplished by use of spectroscopic detectors. Spectroscopic detectors rely on a change in refractive index, ultraviolet and/or visible light absorption, or fluorescence after excitation with a suitable wavelength to detect the separated components. Additionally, the effluent from an LC column may be nebulized to generate an aerosol which is sprayed into a chamber to measure the light scattering properties of the analytes eluting from the column. Alternatively, the separated components may be passed from the liquid chromatography column into other types of analytical instruments for analysis. The volume from the LC column to the detector is minimized in order to maintain the separation efficiency and analysis sensitivity. All system volume not directly resulting from the separation column is referred to as the dead volume or extra-column volume.

The miniaturization of liquid separation techniques to the nano-scale involves small column internal diameters (<100 $\mu$m i.d.) and low mobile phase flow rates (<300 nL/min). Currently, techniques such as capillary zone electrophoresis (CZE), nano-LC, open tubular liquid chromatography (OTLC), and capillary electrochromatography (CEC) offer numerous advantages over conventional scale high performance liquid chromatography (HPLC). These advantages include higher separation efficiencies, high-speed separations, analysis of low volume samples, and the coupling of 2-dimensional techniques. One challenge to using miniaturized separation techniques is detection of the small peak volumes and a limited number of detectors that can accommodate these small volumes. However, coupling of low flow rate liquid separation techniques to electrospray mass spectrometry results in a combination of techniques that are well suited as demonstrated in J. N. Alexander IV, et al., *Rapid Commun. Mass Spectrom.* 12:1187–91(1998). The process of electrospray at flow rates on the order of nanoliters ("nL") per minute has been referred to as "nano-electrospray".

Capillary electrophoresis is a technique that utilizes the electrophoretic nature of molecules and/or the electroosmotic flow of fluids in small capillary tubes to separate components of a fluid. Typically, a fused silica capillary of 100 $\mu$m inner diameter or less is filled with a buffer solution containing an electrolyte. Each end of the capillary is placed in a separate fluidic reservoir containing a buffer electrolyte. A potential voltage is placed in one of the buffer reservoirs and a second potential voltage is placed in the other buffer reservoir. Positively and negatively charged species will migrate in opposite directions through the capillary under the influence of the electric field established by the two potential voltages applied to the buffer reservoirs. Electroosmotic flow is defined as the fluid flow along the walls of a capillary due to the migration of charged species from the buffer solution under the influence of the applied electric field. Some molecules exist as charged species when in solution and will migrate through the capillary based on the charge-to-mass ratio of the molecular species. This migration is defined as electrophoretic mobility. The electroosmotic flow and the electrophoretic mobility of each component of a fluid determine the overall migration for each fluidic component. The fluid flow profile resulting from electroosmotic flow is flat due to the reduction in frictional drag along the walls of the separation channel. This results in improved separation efficiency compared to liquid chromatography where the flow profile is parabolic resulting from pressure driven flow.

Capillary electrochromatography is a hybrid technique that utilizes the electrically driven flow characteristics of electrophoretic separation methods within capillary columns packed with a solid stationary phase typical of liquid chromatography. It couples the separation power of reversed-phase liquid chromatography with the high efficiencies of capillary electrophoresis. Higher efficiencies are obtainable for capillary electrochromatography separations over liquid chromatography, because the flow profile resulting from electroosmotic flow is flat due to the reduction in frictional drag along the walls of the separation channel when compared to the parabolic flow profile resulting from pressure driven flows. Furthermore, smaller particle sizes can be used in capillary electrochromatography than in liquid chromatography, because no backpressure is generated by electroosmotic flow. In contrast to electrophoresis, capillary electrochromatography is capable of separating neutral molecules due to analyte partitioning between the stationary and mobile phases of the column particles using a liquid chromatography separation mechanism.

Microchip-based separation devices have been developed for rapid analysis of large numbers of samples. Compared to other separation devices, these microchip-based separation devices have higher sample throughput, reduced sample and reagent consumption, and reduced chemical waste. The liquid flow rates for microchip-based separation devices range from approximately 1–300 nanoliters per minute for most applications. Examples of microchip-based separation devices include those for capillary electrophoresis ("CE"), capillary electrochromatography ("CEC") and high-performance liquid chromatography ("HPLC") include Harrison et al., *Science* 261:859–97 (1993); Jacobson et al., *Anal. Chem.* 66:1114–18 (1994), Jacobson et al., *Anal. Chem.* 66:2369–73 (1994), Kutter et al., *Anal. Chem.* 69:5165–71 (1997) and He et al., *Anal. Chem.* 70:3790–97 (1998). Such separation devices are capable of fast analyses and provide improved precision and reliability compared to other conventional analytical instruments.

The work of He et al., *Anal. Chem.* 70:3790–97 (1998) demonstrates some of the types of structures that can be fabricated in a glass substrate. This work shows that co-located monolithic support structures (or posts) can be etched reproducibly in a glass substrate using reactive ion etching (RIE) techniques. Currently, anisotropic RIE techniques for glass substrates are limited to etching features that are 20 $\mu$m or less in depth. This work shows rectangular 5 $\mu$m by 5 $\mu$m width by 10 $\mu$m in depth posts and stated that deeper structures were difficult to achieve. The posts are also separated by 1.5 $\mu$m. The posts supports the stationary phase just as with the particles in LC and CEC columns. An advantage to the posts over conventional LC and CEC is that the stationary phase support structures are monolithic with the substrate and therefore, immobile.

He et. al., also describes the importance of maintaining a constant cross-sectional area across the entire length of the separation channel. Large variations in the cross-sectional area can create pressure drops in pressure driven flow systems. In electrokinetically driven flow systems, large variations in the cross-sectional area along the length of a separation channel can create flow restrictions that result in bubble formation in the separation channel. Since the fluid flowing through the separation channel functions as the source and carrier of the mobile solvated ions, formation of a bubble in a separation channel will result in the disruption of the electroosmotic flow.

Electrospray ionization provides for the atmospheric pressure ionization of a liquid sample. The electrospray process creates highly-charged droplets that, under evaporation, create ions representative of the species contained in the solution. An ion-sampling orifice of a mass spectrometer may be used to sample these gas phase ions for mass analysis. When a positive voltage is applied to the tip of the capillary relative to an extracting electrode, such as one provided at the ion-sampling orifice of a mass spectrometer, the electric field causes positively-charged ions in the fluid to migrate to the surface of the fluid at the tip of the capillary. When a negative voltage is applied to the tip of the capillary relative to an extracting electrode, such as one provided at the ion-sampling orifice to the mass spectrometer, the electric field causes negatively-charged ions in the fluid to migrate to the surface of the fluid at the tip of the capillary.

When the repulsion force of the solvated ions exceeds the surface tension of the fluid being electrosprayed, a volume of the fluid is pulled into the shape of a cone, known as a Taylor cone, which extends from the tip of the capillary. A liquid jet extends from the tip of the Taylor cone and becomes unstable and generates charged-droplets. These small charged droplets are drawn toward the extracting electrode. The small droplets are highly-charged and solvent evaporation from the droplets results in the excess charge in the droplet residing on the analyte molecules in the electrosprayed fluid. The charged molecules or ions are drawn through the ion-sampling orifice of the mass spectrometer for mass analysis. This phenomenon has been described, for example, by Dole et al., *Chem. Phys.* 49:2240 (1968) and Yamashita et al., *J. Phys. Chem.* 88:4451 (1984). The potential voltage ("V") required to initiate an electrospray is dependent on the surface tension of the solution as described by, for example, Smith, *IEEE Trans. Ind. Appl.* 1986, IA-22:527–35 (1986). Typically, the electric field is on the order of approximately $10^6$ V/m. The physical size of the capillary and the fluid surface tension determines the density of electric field lines necessary to initiate electrospray.

When the repulsion force of the solvated ions is not sufficient to overcome the surface tension of the fluid exiting the tip of the capillary, large poorly charged droplets are formed. Fluid droplets are produced when the electrical potential difference applied between a conductive or partly conductive fluid exiting a capillary and an electrode is not sufficient to overcome the fluid surface tension to form a Taylor cone.

*Electrospray Ionization Mass Spectrometry: Fundamentals, Instrumentation, and Applications,* edited by R. B. Cole, ISBN 0-471-14564-5, John Wiley & Sons, Inc., New York summarizes much of the fundamental studies of electrospray. Several mathematical models have been generated to explain the principals governing electrospray. Equation 1 defines the electric field $E_c$ at the tip of a capillary of radius $r_c$ with an applied voltage $V_c$ at a distance d from a counter electrode held at ground potential:

$$E_c = \frac{2V_c}{r_c \ln(4/dr_c)} \quad (1)$$

The electric field $E_{on}$ required for the formation of a Taylor cone and liquid jet of a fluid flowing to the tip of this capillary is approximated as:

$$E_{on} \approx \left(\frac{2\gamma \cos\theta}{\varepsilon_0 r_c}\right)^{1/2} \quad (2)$$

where $\gamma$ is the surface tension of the fluid, $\theta$ is the half-angle of the Taylor cone and $\varepsilon_0$ is the permittivity of vacuum. Equation 3 is derived by combining equations 1 and 2 and approximates the onset voltage $V_{on}$ required to initiate an electrospray of a fluid from a capillary:

$$V_{on} \approx \left(\frac{r_c \gamma \cos\theta}{2\varepsilon_0}\right)^{1/2} \ln(4d/r_c) \quad (3)$$

As can be seen by examination of equation 3, the required onset voltage is more dependent on the capillary radius than the distance from the counter-electrode.

It would be desirable to define an electrospray device that could form a stable electrospray of all fluids commonly used in CE, CEC, and LC. The surface tension of solvents commonly used as the mobile phase for these separations range from 100% aqueous ($\gamma$=0.073 N/m) to 100% methanol ($\gamma$=0.0226 N/m). As the surface tension of the electrospray fluid increases, a higher onset voltage is required to initiate an electrospray for a fixed capillary diameter. As an example, a capillary with a tip diameter of 14 $\mu$m is required to electrospray 100% aqueous solutions with an onset voltage of 1000 V. The work of M. S. Wilm et al., *Int. J. Mass Spectrom, Ion Processes* 136:167–80 (1994), first demonstrates nanoelectrospray from a fused-silica capillary pulled to an outer diameter of 5 $\mu$m at a flow rate of 25 nL/min. Specifically, a nanoelectrospray at 25 nL/min was achieved from a 2 $\mu$m inner diameter and 5 $\mu$m outer diameter pulled fused-silica capillary with 600–700 V at a distance of 1–2 mm from the ion-sampling orifice of an electrospray equipped mass spectrometer.

Electrospray in front of an ion-sampling orifice of an API mass spectrometer produces a quantitative response from the mass spectrometer detector due to the analyte molecules present in the liquid flowing from the capillary. One advantage of electrospray is that the response for an analyte measured by the mass spectrometer detector is dependent on the concentration of the analyte in the fluid and independent of the fluid flow rate. The response of an analyte in solution at a given concentration would be comparable using electrospray combined with mass spectrometry at a flow rate of 100 $\mu$L/min compared to a flow rate of 100 nL/min. D. C. Gale et al., *Rapid Commun. Mass Spectrom.* 7:1017 (1993) demonstrate that higher electrospray sensitivity is achieved at lower flow rates due to increased analyte ionization efficiency. Thus by performing electrospray on a fluid at flow rates in the nanoliter per minute range provides the best sensitivity for an analyte contained within the fluid when combined with mass spectrometry.

Thus, it is desirable to provide an electrospray device for integration of microchip-based separation devices with API-MS instruments. This integration places a restriction on the capillary tip defining a nozzle on a microchip. This nozzle will, in all embodiments, exist in a planar or near planar geometry with respect to the substrate defining the separation device and/or the electrospray device. When this co-planar or near planar geometry exists, the electric field lines emanating from the tip of the nozzle will not be enhanced if the electric field around the nozzle is not defined and controlled and, therefore, an electrospray is only achievable with the application of relatively high voltages applied to the fluid.

Attempts have been made to manufacture an electrospray device for microchip-based separations. Ramsey et al., *Anal. Chem.* 69:1174–78 (1997) describes a microchip-based separations device coupled with an electrospray mass spectrometer. This separation device is limited by the fact that the separation channels are located on the surface of the substrate, thus limiting the density of an array of such devices. Previous work from this research group including Jacobson et al., *Anal. Chem.* 66:1114–18 (1994) and Jacobson et al., *Anal. Chem.* 66:2369–73 (1994) demonstrate impressive separations using on-chip fluorescence detection. This more recent work demonstrates nanoelectrospray at 90 nL/min from the edge of a planar glass microchip. The microchip-based surface separation channel has dimensions of 10 μm deep, 60 μm wide, and 33 mm in length. Electroosmotic flow is used to generate fluid flow at 90 nL/min. Application of 4,800 V to the fluid exiting the separation channel on the edge of the microchip at a distance of 3–5 mm from the ion-sampling orifice of an API mass spectrometer generates an electrospray. Approximately 12 nL of the sample fluid collects at the edge of the microchip before the formation of a Taylor cone and stable nanoelectrospray from the edge of the microchip. The volume of this microchip-based separation channel is 19.8 nL. Nanoelectrospray from the edge of this microchip device after capillary electrophoresis or capillary electrochromatography separation is rendered impractical since this system has a dead-volume approaching 60% of the column (channel) volume. Furthermore, because this device provides a flat surface, and, thus, a relatively small amount of physical asperity for the formation of the electrospray, the device requires an impractically high voltage to overcome the fluid surface tension to initiate an electrospray.

Xue, Q. et al., *Anal. Chem.* 69:426–30 (1997) also describes a stable nanoelectrospray from the edge of a planar glass microchip with a closed channel 25 μm deep, 60 μm wide, and 35–50 mm in length. An electrospray is formed by applying 4,200 V to the fluid exiting the separation channel on the edge of the microchip at a distance of 3–8 mm from the ion-sampling orifice of an API mass spectrometer. A syringe pump is utilized to deliver the sample fluid to the glass microchip at a flow rate of 100 to 200 nL/min. The edge of the glass microchip is treated with a hydrophobic coating to alleviate some of the difficulties associated with nanoelectrospray from a flat surface that slightly improves the stability of the nanoelectrospray. Nevertheless, the volume of the Taylor cone on the edge of the microchip is too large relative to the volume of the separation channel, making this method of electrospray directly from the edge of a microchip impracticable when combined with a chromatographic separation device.

T. D. Lee et. al., 1997 *International Conference on Solid-State Sensors and Actuators* Chicago, pp. 927–30 (Jun. 16–19, 1997) describes a multi-step process to generate a nozzle on the edge of a silicon microchip 1–3 μm in diameter or width and 40 μm in length and applying 4,000 V to the entire microchip at a distance of 0.25–0.4 mm from the ion-sampling orifice of an API mass spectrometer. Because a relatively high voltage is required to form an electrospray with the nozzle positioned in very close proximity to the mass spectrometer ion-sampling orifice, this device produces an inefficient electrospray that does not allow for sufficient droplet evaporation before the ions enter the orifice. The extension of the nozzle from the edge of the microchip also exposes the nozzle to accidental breakage. More recently, T. D. Lee et. al., in 1999 *Twelfth IEEE International Micro Electro Mechanical Systems Conference* (Jan. 17–21, 1999), presented this same concept where the electrospray component was fabricated to extend 2.5 mm beyond the edge of the microchip to overcome this phenomenon of poor electric field control within the proximity of a surface.

Thus, it is also desirable to provide an electrospray device with controllable spraying and a method for producing such a device that is easily reproducible and manufacturable in high volumes.

U.S. Pat. No. 5,501,893 to Laermer et. al., reports a method of anisotropic plasma etching of silicon (Bosch process) that provides a method of producing deep vertical structures that is easily reproducible and controllable. This method of anisotropic plasma etching of silicon incorporates a two step process. Step one is an anisotropic etch step using a reactive ion etching (RIE) gas plasma of sulfur hexafluoride ($SF_6$). Step two is a passivation step that deposits a polymer on the vertical surfaces of the silicon substrate. This polymerizing step provides an etch stop on the vertical surface that was exposed in step one. This two step cycle of etch and passivation is repeated until the depth of the desired structure is achieved. This method of anisotropic plasma etching provides etch rates over 3 μm/min of silicon depending on the size of the feature being etched. The process also provides selectivity to etching silicon versus silicon dioxide or resist of greater than 100:1 which is important when deep silicon structures are desired. Laermer et. al., in 1999 *Twelfth IEEE International Micro Electro Mechanical Systems Conference* (Jan. 17–21, 1999), reported improvements to the Bosch process. These improvements include silicon etch rates approaching 10 μm/min, selectivity exceeding 300:1 to silicon dioxide masks, and more uniform etch rates for features that vary in size.

The study of expressed proteins within an organism or specific cell type is known as proteomics. The study of a proteome may involve the analysis of complex mixtures of up to several thousand different proteins within a sample. Analysis of these complex mixtures requires a multidimensional separation of the components of the mixture in order to identify and quantify the levels of the specific proteins. The prior art demonstrates 2-dimensional ("2D") gel electrophoresis as the most common means of performing this first separation. Excising of protein spots from the 2D gel, proteolytically digesting the proteins in each spot followed by mass spectrometry/mass spectrometry ("MS/MS") analysis is well demonstrated. This approach is limited by the ability to quantify and image the protein spots in the gel matrix.

Recently, 2D liquid chromatography ("LC") separations have been demonstrated for complex protein analysis using capillary LC columns. Combining the LC-LC separation with MS/MS results in a powerful, multidimensional separation of complex proteomic samples. The first LC separation phase is commonly based on ion exchange (strong cation exchange) or size exclusion separation modes. The second phase is most commonly based on a reversed phase separation mode. In the case of ion exchange, a complex protein sample may be separated using an increasing salt concentration in the elution buffer over time. By performing a salt gradient in a stepwise method, for example, fractionation of complex mixtures from the first phase being an ion exchange phase to a second phase being a reversed phase provides for a 2D separation of the sample. The prior art teaches this for use in a microcolumn. Further combining this with mass spectrometry/mass spectrometry provides for 2 additional dimensions of separation based on mass/charge ratio. The prior art teaches that by using LC/LC additional proteins are identified compared to 2D gel electrophoresis approaches.

The present invention is directed toward a novel utilization of these features to improve the sensitivity of prior disclosed microchip-based electrospray systems and integration of microchip-based separations and electrospray ionization within a single microfabricated device.

SUMMARY OF THE INVENTION

The present invention relates to an electrospray device for spraying a fluid which includes a substrate having an injection surface and an ejection surface opposing the injection surface. The substrate is preferably an integral monolith and has at least one spray unit. Each spray unit includes an entrance orifice on the injection surface; an exit orifice on the ejection surface; a channel extending through the substrate between the entrance orifice and the exit orifice; and a recess extending into the ejection surface and surrounding the exit orifice. A separation material is associated with the device at a location suitable to effect chromatographic separation of analytes passing through the device. The electrospray device also includes an electric field generating source positioned to define an electric field surrounding at least one exit orifice. In one embodiment, the electric field generating source includes a first electrode attached to the substrate to impart a first potential to the substrate and a second electrode to impart a second potential. The first and the second electrodes are positioned to define an electric field surrounding the exit orifice. This device can be operated to generate multiple electrospray plumes of fluid from each spray unit, to generate a single combined electrospray plume of fluid from a plurality of spray units, and to generate multiple electrospray plumes of fluid from a plurality of spray units. The device can also be used in conjunction with a system for processing an electrospray of fluid, a method of generating an electrospray of fluid, a method of mass spectrometric analysis, and a method of liquid chromatographic analysis.

According to another aspect of the invention, the electrospray device further includes a reservoir upstream of and in fluid communication with the entrance orifice, wherein the reservoir is filled with a separation material suitable to effect chromatographic separation of analytes passing through the electrospray device.

Another aspect of the present invention is directed to an electrospray system for generating multiple sprays from a single fluid stream. The system includes an array of a plurality of the above electrospray devices. The electrospray devices can be provided in the array at a device density exceeding about 5 devices/cm$^2$, about 16 devices/cm$^2$, about 30 devices/cm$^2$, or about 81 devices/cm$^2$. The electrospray devices can also be provided in the array at a device density of from about 30 devices/cm$^2$ to about 100 devices/cm$^2$.

Another aspect of the present invention is directed to an array of a plurality of the above electrospray devices for generating multiple sprays from a single fluid stream. The electrospray devices can be provided in an array wherein the spacing on the ejection surface between adjacent devices is about 9 mm or less, about 4.5 mm or less, about 2.2 mm or less, about 1.1 mm or less, about 0.56 mm or less, or about 0.28 mm or less, respectively.

Another aspect of the present invention is directed to a method of generating an electrospray wherein an electrospray device is provided for spraying a fluid. The electospray device includes a substrate having an injection surface and an ejection surface opposing the injection surface. The substrate is preferably an integral monolith and includes an entrance orifice on the injection surface; an exit orifice on the ejection surface; a channel extending through the substrate between the entrance orifice and the exit orifice; and a recess surrounding the exit orifice and positioned between the injection surface and the ejection surface. The method can be performed to generate multiple electrospray plumes of fluid from each spray unit, to generate a single combined electrospray plume of fluid from a plurality of spray units, and to generate multiple electrospray plumes of fluid from a plurality of spray units. The electrospray device also includes an electric field generating source positioned to define an electric field surrounding the exit orifice. In one embodiment, the electric field generating source includes a first electrode attached to the substrate to impart a first potential to the substrate and a second electrode to impart a second potential. The first and the second electrodes are positioned to define an electric field surrounding the exit orifice. Analyte from a fluid sample is deposited on the injection surface and then eluted with an eluting fluid. The eluting fluid containing analyte is passed into the entrance orifice through the channel and through the exit orifice. A first potential is applied to the first electrode and a second potential is applied to the fluid through the second electrode. The first and second potentials are selected such that fluid discharged from the exit orifice of each of the spray units forms an electrospray.

Another aspect of the present invention is directed a method of producing an electrospray device including providing a substrate having opposed first and second surfaces, at least the first side is coated with a photoresist over an etch-resistant material. The photoresist on the first surface is exposed to an image to form a pattern in the form of at least one ring on the first surface. The exposed photoresist is removed on the first surface which is outside and inside the at least one ring leaving the unexposed photoresist. The etch-resistant material is removed from the first surface of the substrate where the exposed photoresist was removed to form holes in the etch-resistant material. Photoresist is removed from the first surface. Photoresist is provided over an etch-resistant material on the second surface and exposed to an image to form a pattern circumscribing extensions of the at least one ring formed in the etch-resistant material of the first surface. The exposed photoresist on the second surface is removed. The etch-resistant material on the second surface is removed coincident with where the photoresist was removed. Material is removed from the substrate coincident with where the etch-resistant material on the second surface was removed to form a reservoir extending into the substrate. The remaining photoresist on the second surface is removed. The second surface is coated with an etch-resistant material. The first surface is coated with a second coating of photoresist. The second coating of photoresist within the at least one ring is exposed to an image. The exposed second coating of photoresist is removed from within the at least one ring to form at least one hole. Material is removed from the substrate coincident with the at least one hole in the second layer of photoresist on the first surface to form at least one passage extending through the second layer of photoresist on the first surface and into substrate to the extent needed to reach the etch-resistant material coating the reservoir. Photoresist from at least the first surface is removed. An etch-resistant layer is applied to all exposed surfaces of the substrate. Material is removed from the substrate exposed by the removed etch-resistant layer around the at least one ring to define at least one nozzle on the first surface. The etch-resistant material coating the reservoir is removed from the substrate. An etch resistant material is applied to coat all exposed surfaces of the substrate. At least one of the reservoir and the at least one passage is filled with a polymerizable material. The polymerizable material is then polymerized.

Another aspect of the present invention relates to a method of producing an electrospray device. An electrospray device is provided having an injection surface having an entrance orifice and a reservoir in fluid communication with the entrance orifice. An ejection surface opposes the injection surface and has an exit orifice. A channel extends through the substrate between the entrance orifice and the exit orifice. A recess extends into the ejection surface and surrounds the exit orifice. An electric field generating source is positioned to define an electric field which surrounds the exit orifice. At least one of the passage and the reservoir is filled with a polymerizable material and polymerized.

Another aspect of the present invention relates to a separation block. The separation block includes an injection surface having a plurality of entrance orifices. An ejection surface opposes the injection surface and has a plurality of exit orifices each corresponding to a respective one of the plurality of entrance orifices. A plurality of channels extends through the substrate between one of the plurality of entrance orifices and the corresponding one of the plurality of exit orifices. The channels are filled with a separation material suitable to effect chromatographic separation of analytes passing through the block.

Another aspect of the present invention relates to a separation block system including a plurality of separation blocks described above, wherein the separation blocks are stacked one upon the other and each of the plurality of exit orifices of one block are aligned with the corresponding one of the plurality of entrance orifices of the other block.

Another aspect of the present invention relates to a method for processing samples of fluid including passing at least one sample through a respective one of a first array of multiple through-substrate channels containing a first separation material suitable to effect chromatographic separation of analytes passing through. The at least one sample is passed from the first array through a respective one of a second array of multiple through-substrate channels containing a second separation material having the same or different separation characteristics than the first separation material. Optionally, the previous step is repeated sequentially with one or a plurality of arrays of multiple through-substrate channels. The at least one sample is passed to corresponding entrance orifices of a system of electrospray devices. The at least one sample is electrosprayed and passed to a detector, which detects at least one analyte in the electrospray. The electrospray can be detected by sequentially spraying each electrospray in communication with the detector. The electrospray can also be detected by simultaneously spraying a plurality of electrosprays and sweeping the detector in communication with the electrosprays.

The present invention relates to the complete integration of microchip-based separations and electrospray ionization within a single microfabricated device. A continuous or monolithic polymer bed formed by in situ polymerization of a monomer solution containing a porogen can be contained within the separation channel in this integrated device. The present invention is directed toward improving coupling of microchip-based separations and electrospray mass spectrometry. This present invention discloses the integration of a polymer monolith within a separation channel formed through a silicon monolith together with an electrospray nozzle microfabricated using Micro-ElectroMechanical Systems technology. The integration of a microchip-based polymer monolithic column and electrospray is a significant advance over prior disclosed systems and methods.

The electrospray device of the present invention can generate multiple electrospray plumes from a single fluid stream and be simultaneously combined with mass spectrometry. Each electrospray plume generates a signal for an analyte contained within a fluid that is proportional to that analytes concentration. When multiple electrospray plumes are generated from one nozzle, the ion intensity for a given analyte will increase with the number of electrospray plumes emanating from that nozzle as measured by the mass spectrometer. When multiple nozzle arrays generate one or more electrospray plumes, the ion intensity will increase with the number of nozzles times the number of electrospray plumes emanating from the nozzle arrays.

The present invention achieves a significant advantage in terms of high-sensitivity analysis of analytes by liquid phase separations-electrospray mass spectrometry. A method of control of the electric field around closely positioned electrospray nozzles provides a method of generating multiple electrospray plumes from closely positioned nozzles in a well-controlled process. An array of electrospray nozzles is disclosed for generation of multiple electrospray plumes of a solution for the purpose of generating an ion response as measured by a mass spectrometer that increases with the total number of generated electrospray plumes. The present invention achieves a significant advantage in comparison to prior disclosed electrospray systems and methods for combination with microfluidic chip-based separation devices incorporating a single nozzle forming a single electrospray.

The electrospray device of the present invention generally includes a silicon substrate material defining a through-substrate channel between an entrance orifice on an injection surface and a nozzle on an ejection surface (the major surface) such that the electrospray generated by the device is generally perpendicular to the ejection surface. The nozzle has an inner and an outer diameter and is defined by an annular portion recessed from the ejection surface. The recessed annular region extends radially from the outer diameter. The tip of the nozzle is co-planar or level with and does not extend beyond the ejection surface. Thus, the nozzle is protected against accidental breakage. The nozzle, the channel, and the recessed annular region are etched from the silicon substrate by deep reactive-ion etching and other standard semiconductor processing techniques.

All surfaces of the silicon substrate preferably have insulating layers thereon to electrically isolate the liquid sample from the substrate and the ejection and injection surfaces from each other such that different potential voltages may be individually applied to each surface, the silicon substrate and the liquid sample. The insulating layer generally constitutes a silicon dioxide layer combined with a silicon nitride layer. The silicon nitride layer provides a moisture barrier against water and ions from penetrating through to the substrate thus preventing electrical breakdown between a fluid moving in the channel and the substrate. The electrospray apparatus preferably includes at least one controlling electrode electrically contacting the substrate for the application of an electric potential to the substrate.

Preferably, the nozzle, channel and recess are etched from the silicon substrate by reactive-ion etching and other standard semiconductor processing techniques. The injection-side features, through-substrate fluid channel, ejection-side features, and controlling electrodes are formed monolithically from a monocrystalline silicon substrate—i.e., they are formed during the course of and as a result of a fabrication sequence that requires no manipulation or assembly of separate components.

Because the electrospray device is manufactured using reactive-ion etching and other standard semiconductor processing techniques, the dimensions of such a device nozzle can be very small, for example, as small as 2 $\mu$m inner diameter and 5 $\mu$m outer diameter. Thus, a through-substrate fluid channel having, for example, 5 $\mu$m inner diameter and a substrate thickness of 250 $\mu$m only has a volume of 4.9 pL ("picoliters"). The micrometer-scale dimensions of the electrospray device minimize the dead volume and thereby increase efficiency and analysis sensitivity when combined with a separation device.

The electrospray device of the present invention provides for the efficient and effective formation of an electrospray. By providing an electrospray surface (i.e., the tip of the nozzle) from which the fluid is ejected with dimensions on the order of micrometers, the device limits the voltage required to generate a Taylor cone and subsequent electrospray. The nozzle of the electrospray device provides the physical asperity on the order of micrometers on which a large electric field is concentrated. Further, the nozzle of the electrospray device contains a thin region of conductive silicon insulated from a fluid moving through the nozzle by the insulating silicon dioxide and silicon nitride layers. The fluid and substrate voltages and the thickness of the insulating layers separating the silicon substrate from the fluid determine the electric field at the tip of the nozzle. Additional electrode(s) on the ejection surface to which electric potential(s) may be applied and controlled independent of the electric potentials of the fluid and the substrate may be incorporated in order to advantageously modify and optimize the electric field in order to focus the gas phase ions produced by the electrospray.

The microchip-based electrospray device of the present invention provides minimal extra-column dispersion as a result of a reduction in the extra-column volume and provides efficient, reproducible, reliable and rugged formation of an electrospray. This electrospray device is perfectly suited as a means of electrospray of fluids from microchip-based separation devices. The design of this electrospray device is also robust such that the device can be readily mass-produced in a cost-effective, high-yielding process.

The electrospray device may be interfaced to or integrated downstream from a sampling device, depending on the particular application. For example, the analyte may be electrosprayed onto a surface to coat that surface or into another device for purposes of conveyance, analysis, and/or synthesis. As described previously, highly charged droplets are formed at atmospheric pressure by the electrospray device from nanoliter-scale volumes of an analyte. The highly charged droplets produce gas-phase ions upon sufficient evaporation of solvent molecules which may be sampled, for example, through an ion-sampling orifice of an atmospheric pressure ionization mass spectrometer ("API-MS") for analysis of the electrosprayed fluid.

A multi-system chip thus provides a rapid sequential chemical analysis system fabricated using Micro-ElectroMechanical System ("MEMS") technology. The multi-system chip enables automated, sequential separation and injection of a multiplicity of samples, resulting in significantly greater analysis throughput and utilization of the mass spectrometer instrument for high-throughput detection of compounds for drug discovery.

Another aspect of the present invention provides a silicon microchip-based electrospray device for producing electrospray of a liquid sample. The electrospray device may be interfaced downstream to an atmospheric pressure ionization mass spectrometer ("API-MS") for analysis of the electrosprayed fluid.

The use of multiple nozzles for electrospray of fluid from the same fluid stream extends the useful flow rate range of microchip-based electrospray devices. Thus, fluids may be introduced to the multiple electrospray device at higher flow rates as the total fluid flow is split between all of the nozzles. For example, by using 10 nozzles per fluid channel, the total flow can be 10 times higher than when using only one nozzle per fluid channel. Likewise, by using 100 nozzles per fluid channel, the total flow can be 100 times higher than when using only one nozzle per fluid channel. The fabrication methods used to form these electrospray nozzles allow for multiple nozzles to be easily combined with a single fluid stream channel greatly extending the useful fluid flow rate range and increasing the mass spectral sensitivity for microfluidic devices.

The use of polymer monoliths contained within the through-substrate channels of this electrospray device incorporating multiple nozzles is a significant advance compared to prior disclosed microchip-based separations-electrospray systems and methods combined with mass spectrometry. Polymer monoliths have demonstrated that faster separations are possible while maintaining chromatographic resolution simply by increasing the linear flow velocity of the mobile phase. The use of multiple electrospray nozzles for one separation channel will be able to accommodate the higher flow rates necessary for fast, rapid microchip-based separations using polymer monolithic beds. The use of through-substrate channels allows for simultaneous deposition of discreet sample volumes on the polymer monoliths on the injection side of the substrate. The analytes contained within the sample volumes will partition into the polymer monolith while the fluid droplets evaporate. A fluidic probe or array of probes can then interface to the injection side of the microchip to deliver a mobile phase to the device to cause the separation and electrospray mass spectrometry analysis of the transferred analytes.

BRIEF DESCRIPTION OF THE DRAWINGS

FIG. 1H shows a perspective view of a one-nozzle electrospray device of the present invention.

FIG. 1I shows a perspective view of a two-nozzle electrospray device of the present invention.

FIG. 1J shows a perspective view of a three-nozzle electrospray device of the present invention.

FIG. 1K shows a perspective view of a fourteen-nozzle electrospray device of the present invention.

FIG. 14C is a cross-sectional view of a silicon substrate 200 showing of removal of photoresist layer 226 to form a pattern of 224 in the photoresist and exposing the silicon dioxide 228 of silicon dioxide layer 212.

FIG. 20A shows two stacked separation blocks each having a plurality of separation channels filled with a porous polymeric material.

DETAILED DESCRIPTION OF THE INVENTION

Figure 1A:
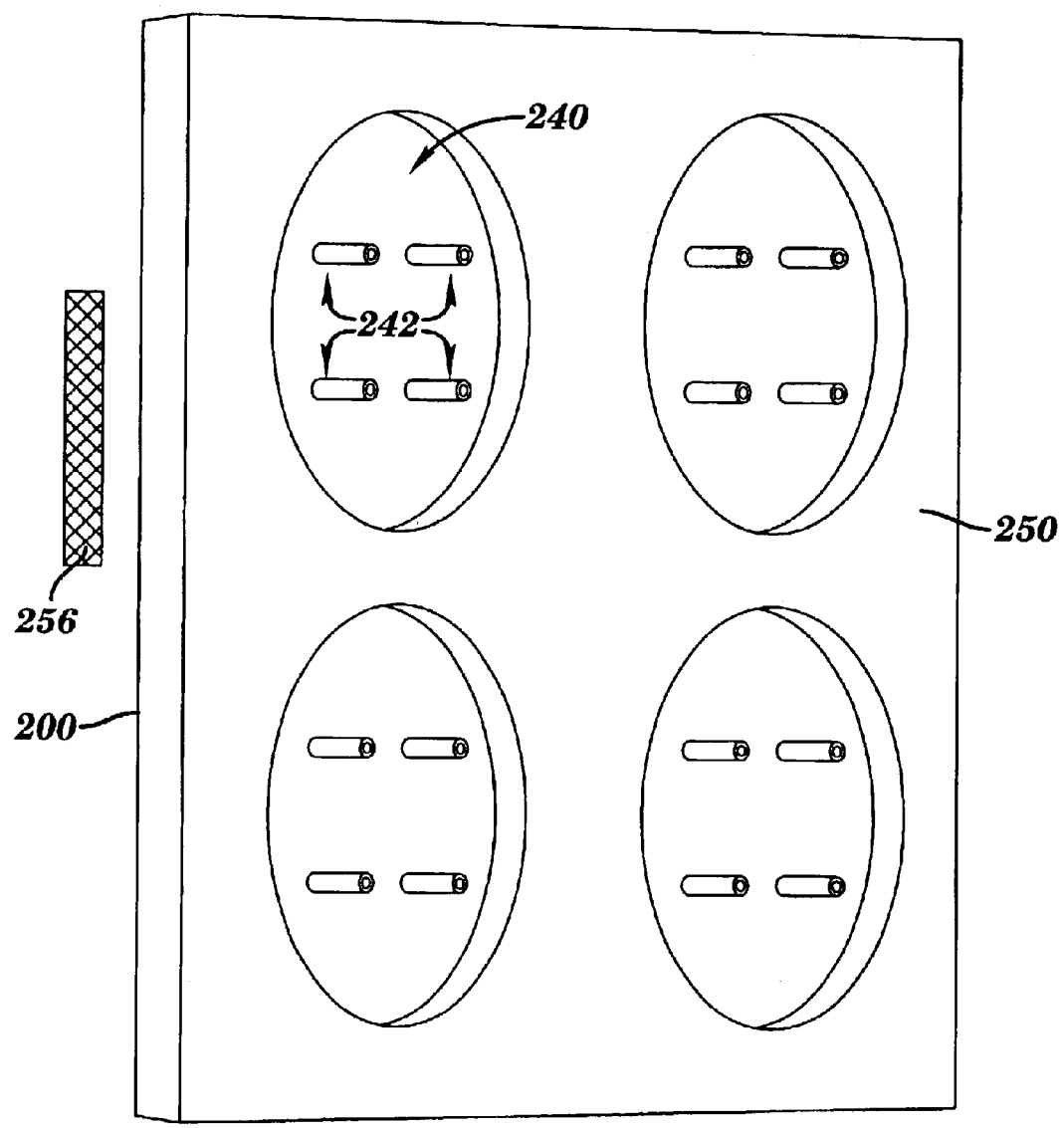
FIG. 1A shows a perspective view of the ejection or nozzle side polymer monolith/multiple-nozzle electrospray device of the present invention.

Control of the electric field at the tip of a nozzle is an important component for successful generation of an electrospray for microfluidic microchip-based systems. This invention provides sufficient control and definition of the electric field in and around a nozzle microfabricated from a monolithic silicon substrate for the formation of multiple electrospray plumes from closely positioned nozzles. The present nozzle system is fabricated using MicroElectroMechanical System ("MEMS") fabrication technologies designed to micromachine 3-dimensional features from a silicon substrate. MEMS technology, in particular, deep reactive ion etching ("DRIE"), enables etching of the small vertical features required for the formation of micrometer dimension surfaces in the form of a nozzle for successful nanoelectrospray of fluids. Insulating layers of silicon dioxide and silicon nitride are also used for independent application of an electric field surrounding the nozzle, preferably by application of a potential voltage to a fluid flowing through the silicon device and a potential voltage applied to the silicon substrate. This independent application of a potential voltage to a fluid exiting the nozzle tip and the silicon substrate creates a high electric field, on the order of $10^8$ V/m, at the tip of the nozzle. This high electric field at the nozzle tip causes the formation of a Taylor cone, fluidic jet and highly-charged fluidic droplets characteristic of the electrospray of fluids. These two voltages, the fluid voltage and the substrate voltage, control the formation of a stable electrospray from this microchip-based electrospray device.

The electrical properties of silicon and silicon-based materials are well characterized. The use of silicon dioxide and silicon nitride layers grown or deposited on the surfaces of a silicon substrate are well known to provide electrical insulating properties. Incorporating silicon dioxide and silicon nitride layers in a monolithic silicon electrospray device with a defined nozzle provides for the enhancement of an electric field in and around features etched from a monolithic silicon substrate. This is accomplished by independent application of a voltage to the fluid exiting the nozzle and the region surrounding the nozzle. Silicon dioxide layers may be grown thermally in an oven to a desired thickness. Silicon nitride can be deposited using low pressure chemical vapor deposition ("LPCVD"). Metals may be further vapor deposited on these surfaces to provide for application of a potential voltage on the surface of the device. Both silicon dioxide and silicon nitride function as electrical insulators allowing the application of a potential voltage to the substrate that is different than that applied to the surface of the device. An important feature of a silicon nitride layer is that it provides a moisture barrier between the silicon substrate, silicon dioxide and any fluid sample that comes in contact with the device. Silicon nitride prevents water and ions from diffusing through the silicon dioxide layer to the silicon substrate which may cause an electrical breakdown between the fluid and the silicon substrate. Additional layers of silicon dioxide, metals and other materials may further be deposited on the silicon nitride layer to provide chemical functionality to silicon-based devices.

Arrays of multiple electrospray nozzles of any nozzle number and format may be fabricated according to the present invention. FIG. 1A illustrates a two by two array of groups of four electrospray nozzles for one common fluid stream. FIG. 1A shows a perspective view of the ejection or nozzle side a four-nozzle electrospray device array 250 of the present invention. Each recessed annular region 240 has four nozzles 242 that generate one or more electrosprays for the same fluid stream introduced to a reservoir containing a polymer monolith on the injection side of the device. Each device has a group of four electrospray nozzles in fluid communication with one common reservoir containing a single fluid sample source. Thus, this system can generate multiple sprays for each fluid stream up to four different fluid streams. An electrode 256 is placed on the silicon substrate 200 for application of a potential voltage to the substrate.

Figure 1B:
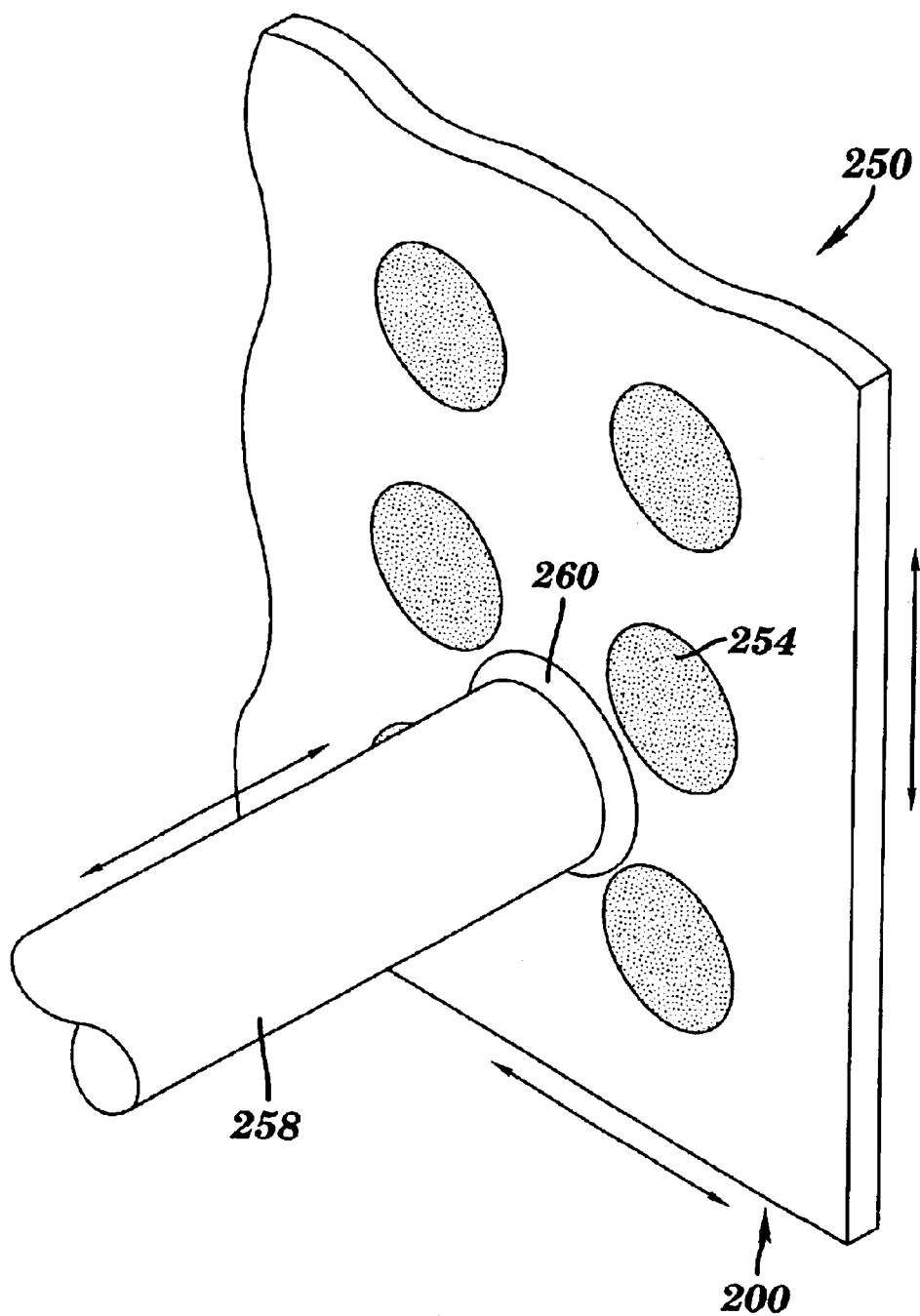
FIG. 1B shows a perspective view of the injection or polymer monolith side of a polymer monolith/multiple-nozzle electrospray device of the present invention.

FIG. 1B shows a perspective view of the injection side of a polymer monolith/multi-nozzle electrospray device 250 of the present invention. FIG. 1B shows a perspective view of the injection or polymer monolith side of a four-nozzle electrospray device array 250 of the present invention. This figure shows a fluid delivery device 258 incorporating a seal 260 for sealing against the injection side surface circumscribing the reservoir containing a polymer monolith 254.

Figure 1C:
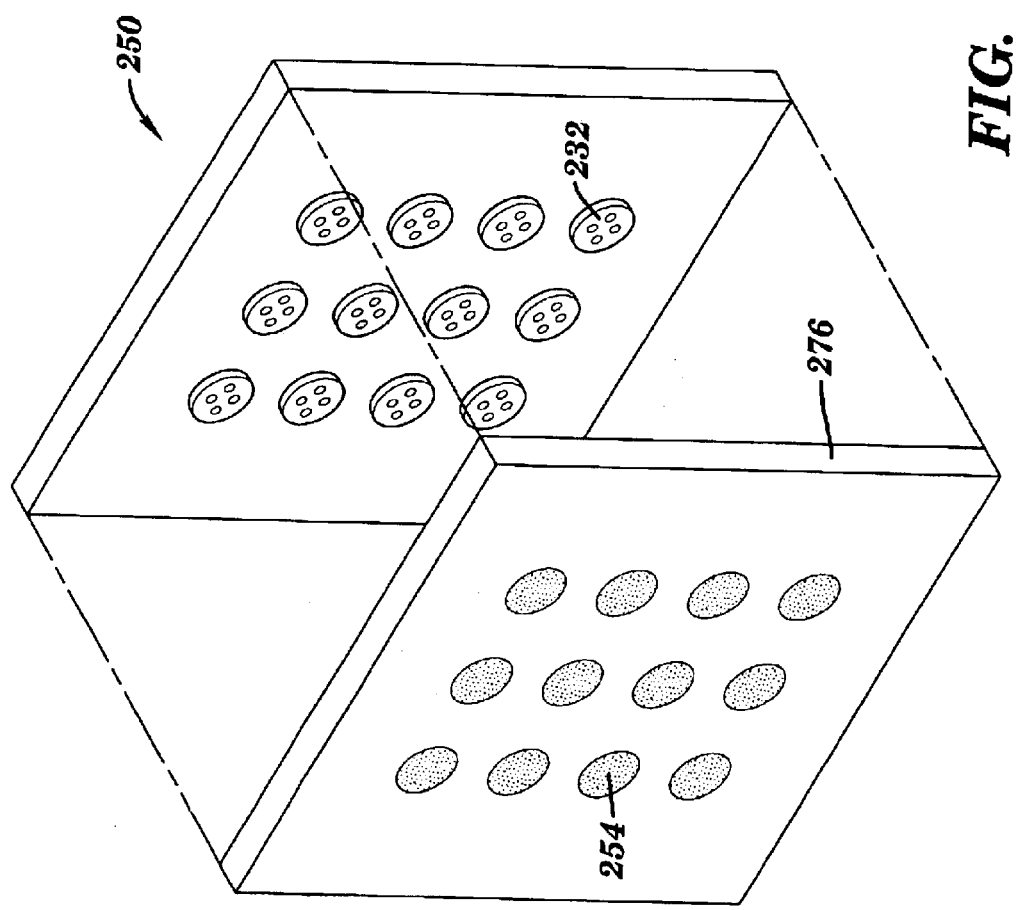
FIG. 1C shows a perspective view of the injection or polymer monolith side of a polymer monolith/multiple-nozzle electrospray device of the present invention showing reservoir extension block 276. The reservoir extension block can function as a larger fluid reservoir or contain polymer monolith to increase the separation column length.

FIG. 1C shows an array 250 of reservoirs 232 in alignment with a polymer separation block 276. The polymer separation block 276 has an array of channels 254 containing the polymer separation monolith which is aligned with the array 250 of reservoirs 232.

Figure 1D:
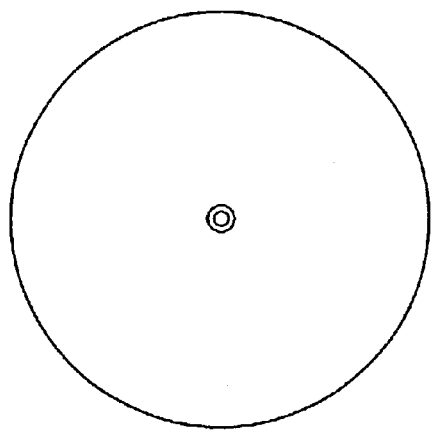
FIG. 1D shows a plan view of a one-nozzle electrospray device of the present invention.
Figure 1E:
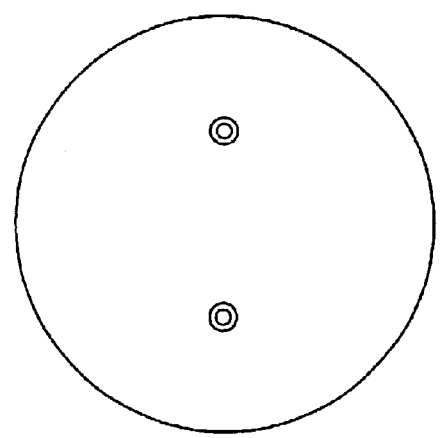
FIG. 1E shows a plan view of a two-nozzle electrospray device of the present invention.
Figure 1F:
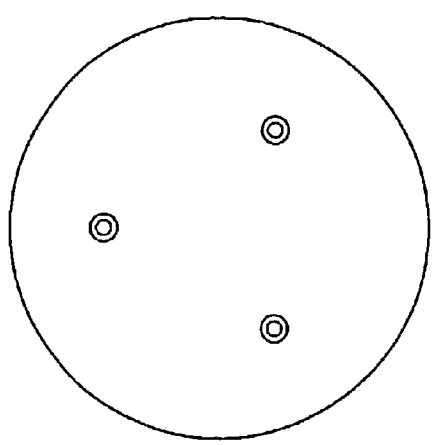
FIG. 1F shows a plan view of a three-nozzle electrospray device of the present invention.
Figure 1G:
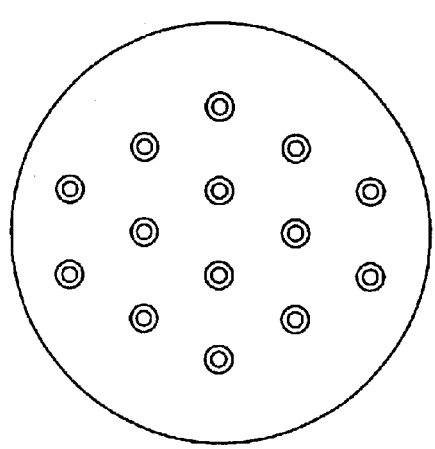
FIG. 1G shows a plan view of a fourteen-nozzle electrospray device of the present invention.
Figure 1L:
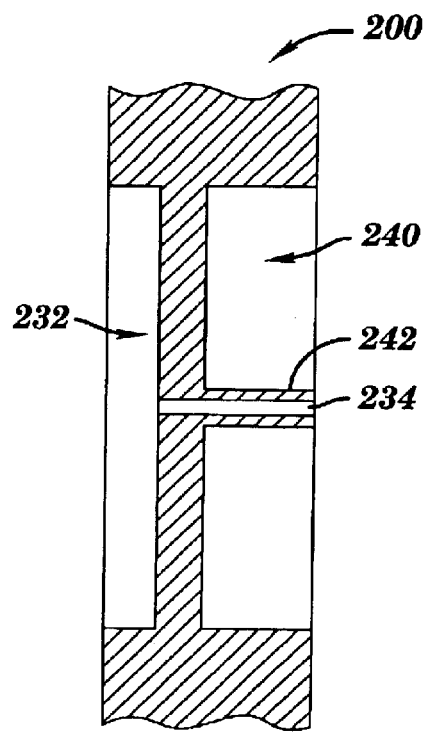
FIG. 1L shows a cross-sectional view of a one-nozzle electrospray device of the present invention.
Figure 1M:
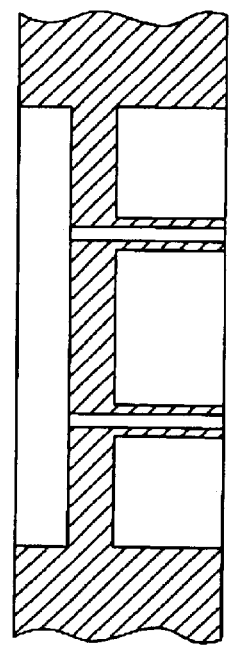
FIG. 1M shows a cross-sectional view of a two-nozzle electrospray device of the present invention.
Figure 1N:
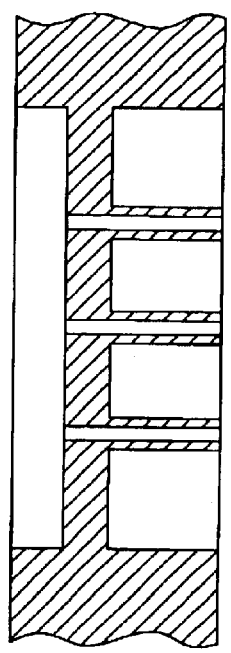
FIG. 1N shows a cross-sectional view of a three-nozzle electrospray device of the present invention.
Figure 1O:
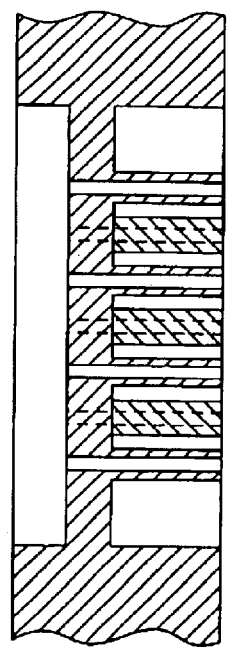
FIG. 1O shows a cross-sectional view of a fourteen-nozzle electrospray device of the present invention.

FIGS. 1D–1E show plan views of 1, 2, 3 and 14 nozzle electrospray devices, respectively, of the present invention. FIGS. 1H–1K show perspective views of the nozzle side of an electrospray device showing 1, 2, 3 and 14 nozzles 242, respectively, etched in the recessed annular region 240 of the silicon substrate 200. FIGS. 1L–1O show cross-sectional views of 1, 2, 3 and 14 nozzle electrospray devices, respectively. The nozzle 242 or ejection side of the device and the reservoir 232 or injection side of the device are connected by the through-substrate channels 234 thus creating a fluidic path through the silicon substrate 200.

Fluids may be introduced to this microfabricated electrospray device by a fluid delivery device such as a probe, conduit, capillary, micropipette, microchip, or the like. The perspective view of FIG. 1B shows a probe 258 that moves into contact with the injection or reservoir side of the electrospray device of the present invention. The probe can have a disposable tip. This fluid probe has a seal 260, for example an o-ring, at the tip to form a seal between the probe tip and the injection surface of the substrate 200. FIG. 1B shows an array of a plurality of electrospray devices fabricated on a monolithic substrate. One liquid sample handling device is shown for clarity, however, multiple liquid sampling devices can be utilized to provide one or more fluid samples to one or more electrospray devices in accordance with the present invention. The fluid probe and the substrate can be manipulated in 3-dimensions for staging of, for example, different devices in front of a mass spectrometer or other sample detection apparatus.

Figure 2A:
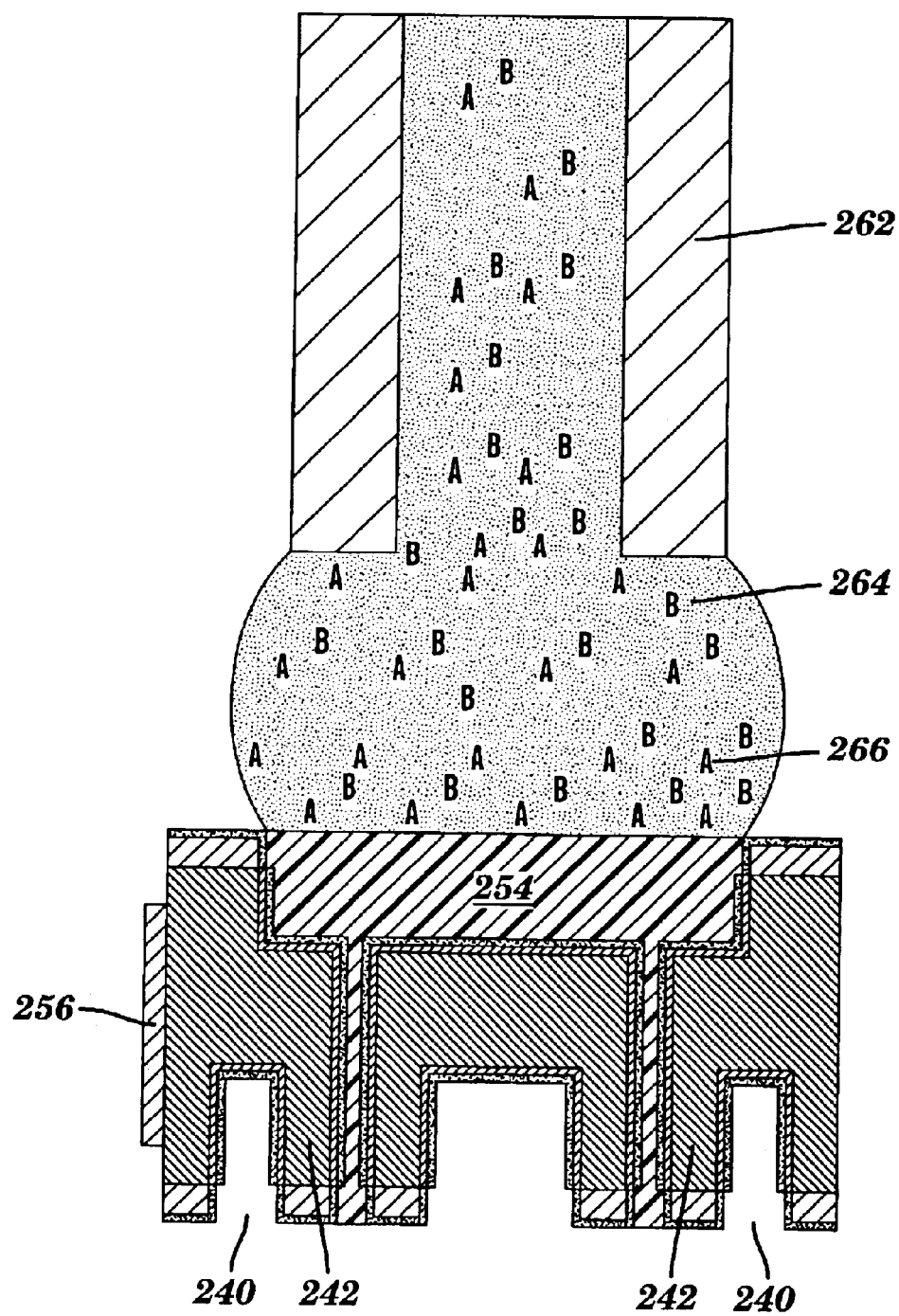
FIGS. 2A–2E show a cross-sectional view of a polymer monolith/multiple-nozzle electrospray device of the present invention illustrating the transfer of a discreet sample volume to polymer monolith on the injection side. The analytes A and B partition to the polymer monolith, the sample volume evaporates, mobile phase is delivered to the microchip via a fluid delivery device and reconstitution and liquid separation-electrospray mass spectrometry analysis of the analytes A and B is performed.
Figure 2B:
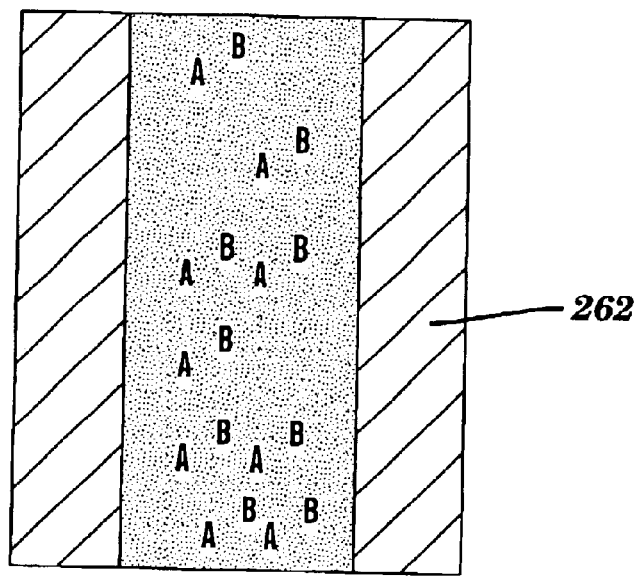
Figure 2B:
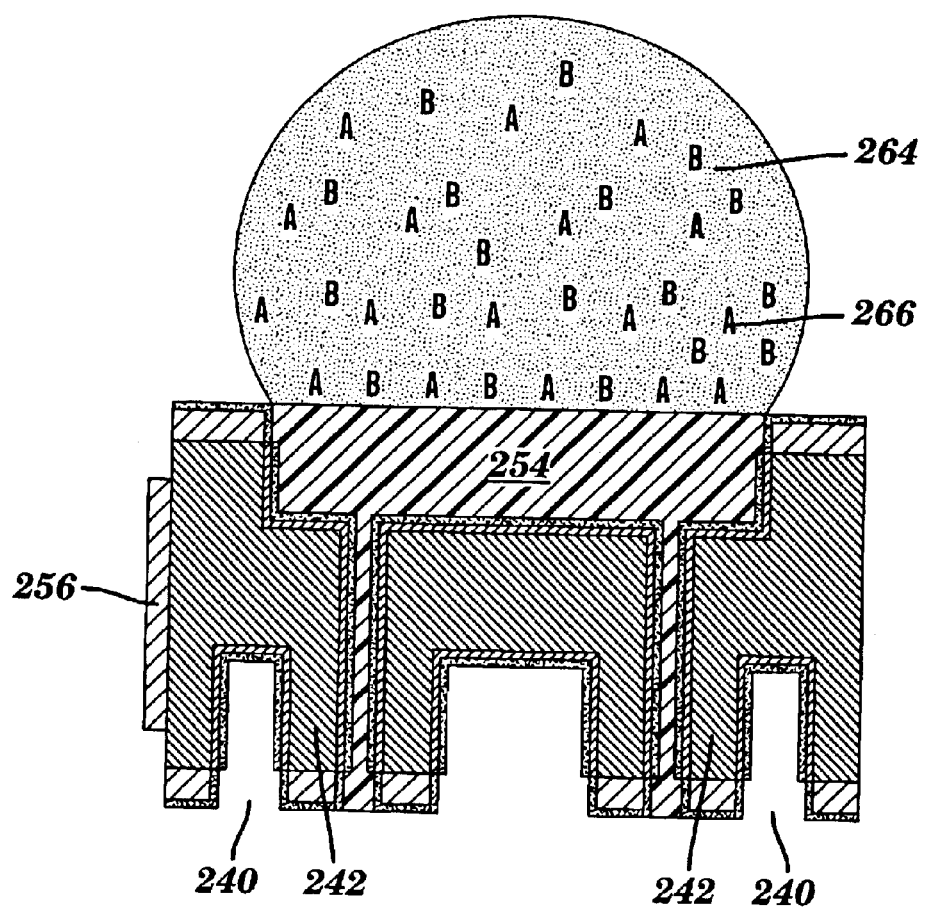
Figure 2C:
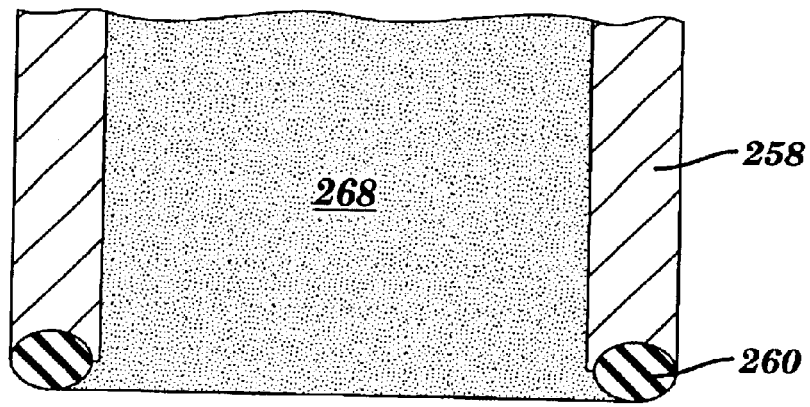
Figure 2C:
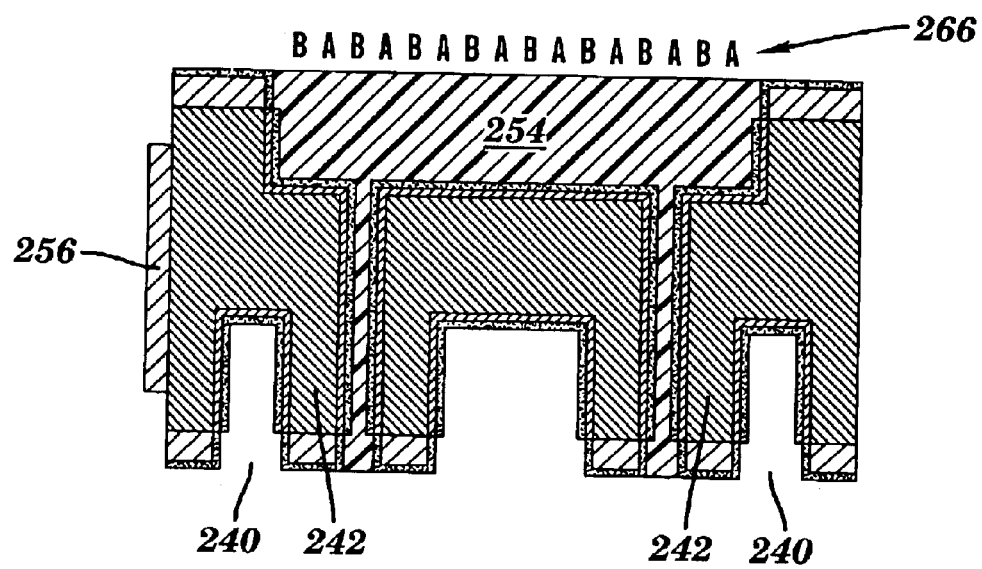
Figure 2D:
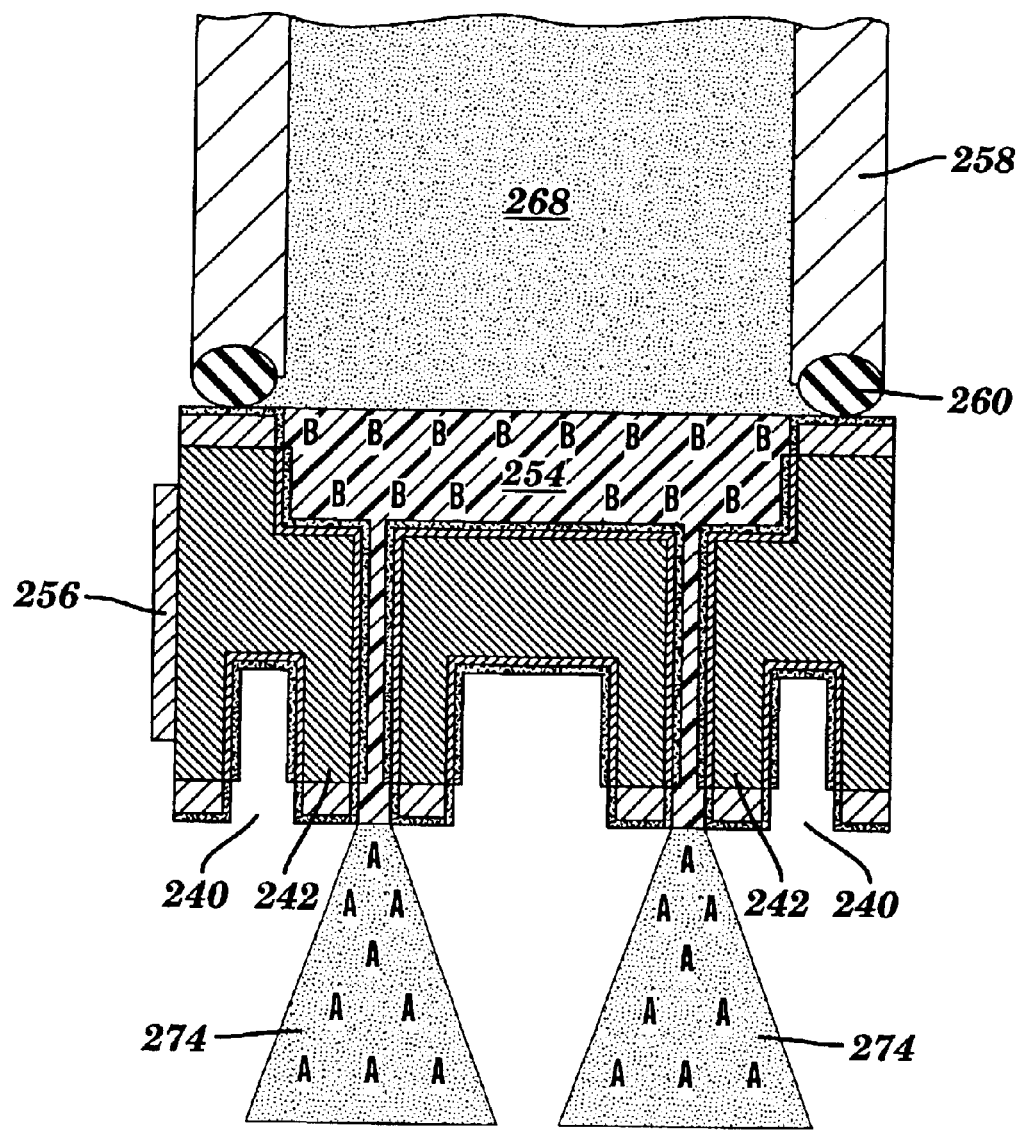
Figure 2E:
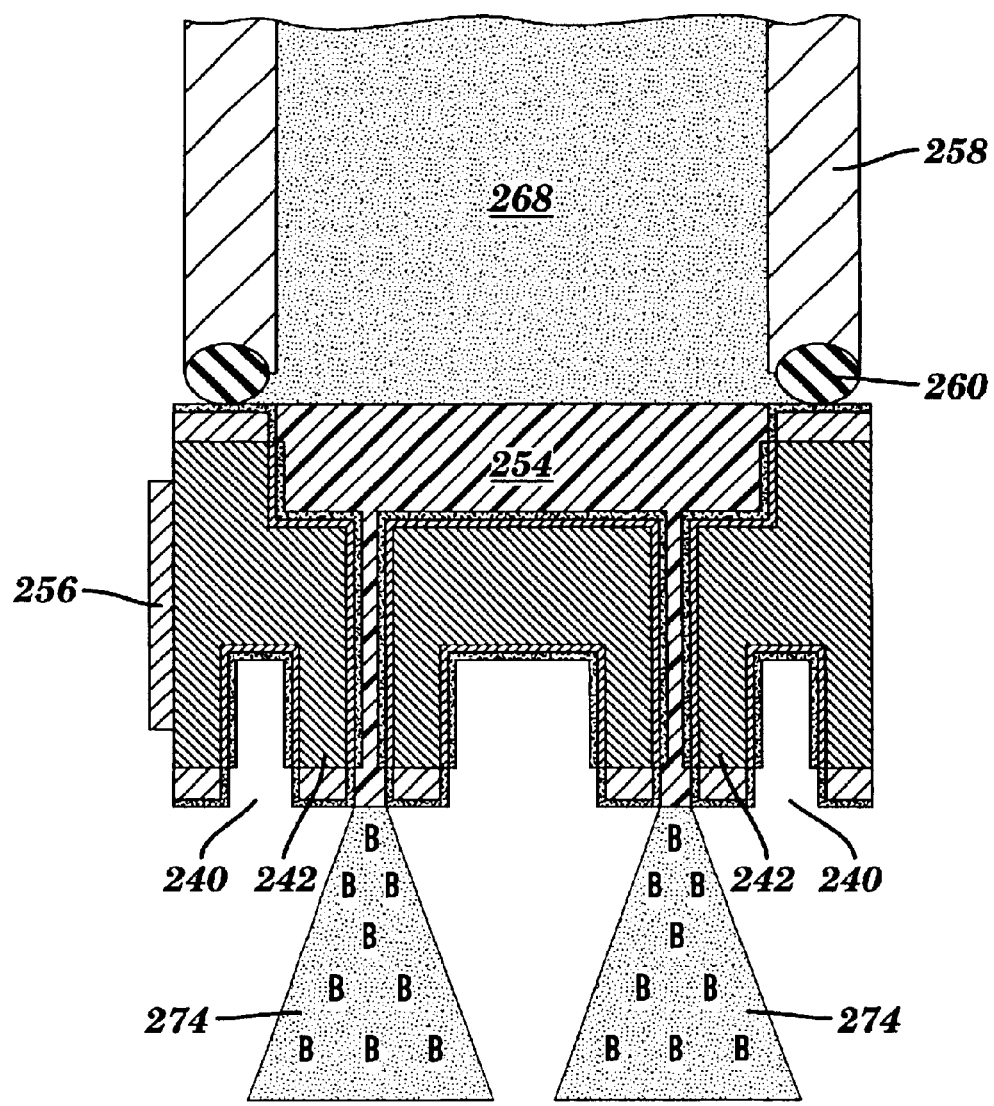

FIGS. 2A–2C illustrate the deposition of a discreet sample onto a polymer monolith/multiple-electrospray device 250 of the present invention. The figures show a fluidic probe 262 depositing or transferring a sample to a polymer monolith 254 on the injection surface. The fluidic sample 264 is delivered to the polymer monolith 254 as a discreet volume, generally less than 100 nL. Alternately, this reservoir surface may be coated with a different retentive phase, such as a hydrophobic C18-like phase commonly used for LC applications, for increasing the partition of analytes contained within the fluid delivered to the reservoir surface. The analytes 266 A & B partition into the polymer monolith 254 while the fluid droplets 264 evaporate. As shown in FIGS. 2D–2E, a fluid delivery probe 258 is sealed against the injection surface by a seal 260 to deliver a fluid mobile phase to the microchip to reconstitute the transferred analytes 266 for separation and electrospray mass spectrometry analysis.

FIG. 2A shows a probe 262 that apportions a fluid 264 containing analytes 266 A & B onto the polymer monolith 254 contained within a reservoir on the injection side of a polymer monolith/multiple electrospray device 250 of the present invention. FIG. 2B shows the fluid delivery device 262 retracted from the device 250 leaving a fluid droplet 264 on the polymer monolith 254. The analyte molecules 266 will partition onto the polymer monolith while the fluid droplet 264 evaporates to dryness as shown in FIG. 2C. FIG. 2D shows a fluid delivery device 258 incorporating a seal 260 to the injection side of the device 250 used to deliver a solution 268 suitable to elute the analytes 266 through the polymer monolith 254 for electrospray mass spectrometry analysis of the eluted analytes. The fluid probe 258 and the polymer monolith/multiple electrospray device 250 can be manipulated in 3-dimensions for staging of different devices in front of a mass spectrometer. The probe can have a disposable tip, such as a capillary, micropipette, or microchip.

Figure 3A:
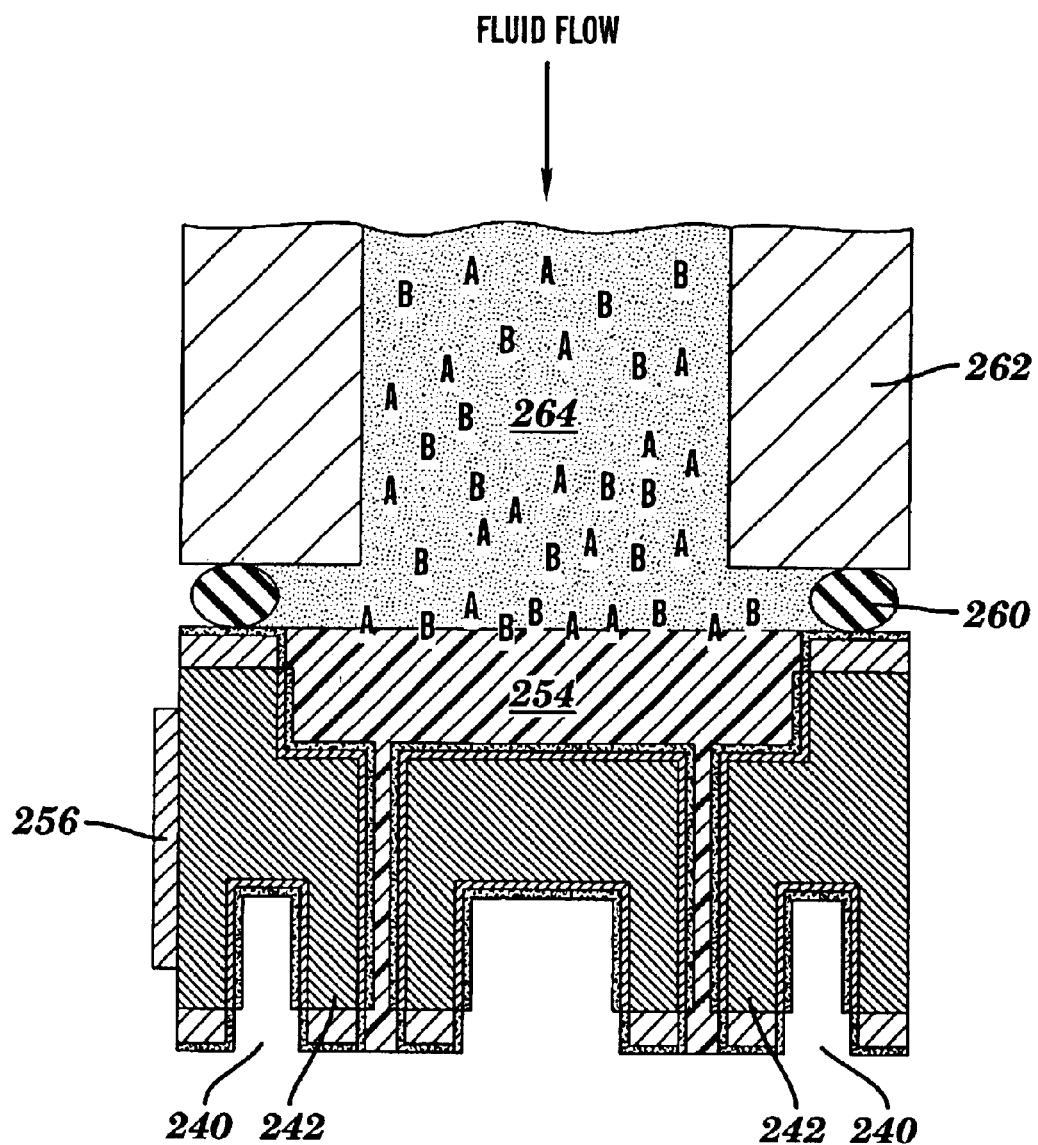
FIGS. 3A–3D show a cross-sectional view of a polymer monolith/multiple-nozzle electrospray-device of the present invention illustrating the loading of a large sample volume to the reservoir. The polymer monolith is contained within the injection side of the present invention. Analytes A and B are adsorbed to the polymer monolith, the sample volume evaporates, a mobile phase is delivered to the microchip via a fluid delivery device and reconstitution and liquid separation-electrospray mass spectrometry analysis of the analytes A and B is performed.
Figure 3B:
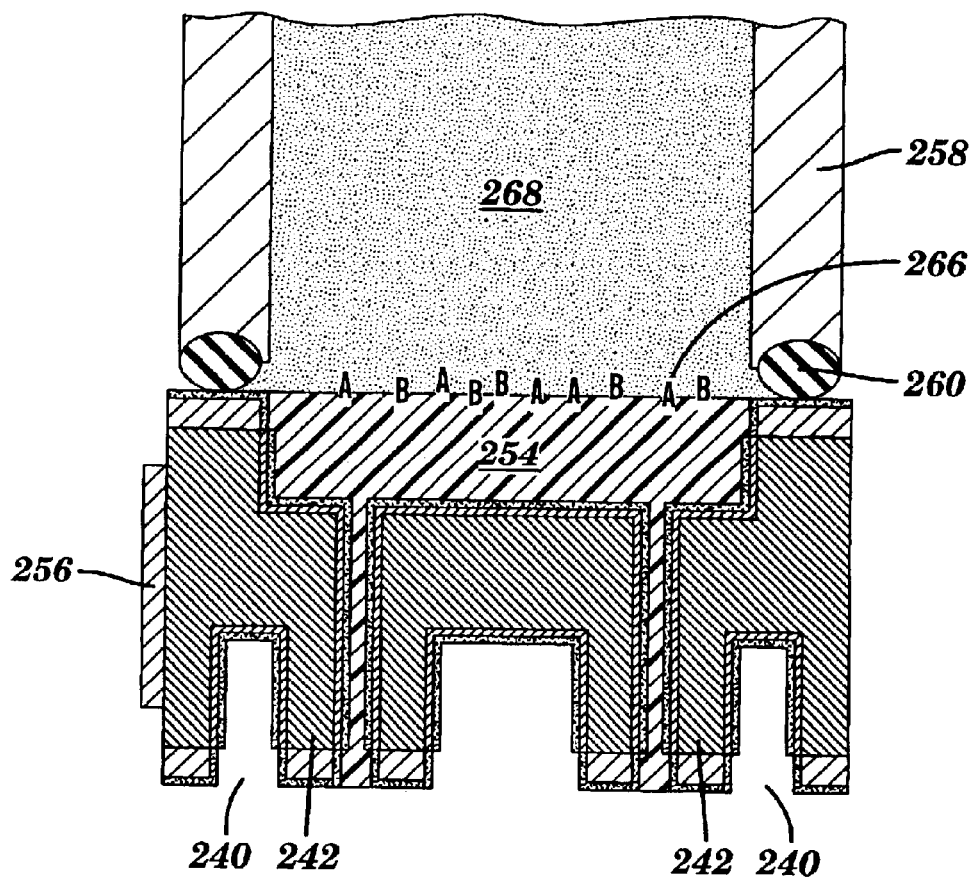
Figure 3C:
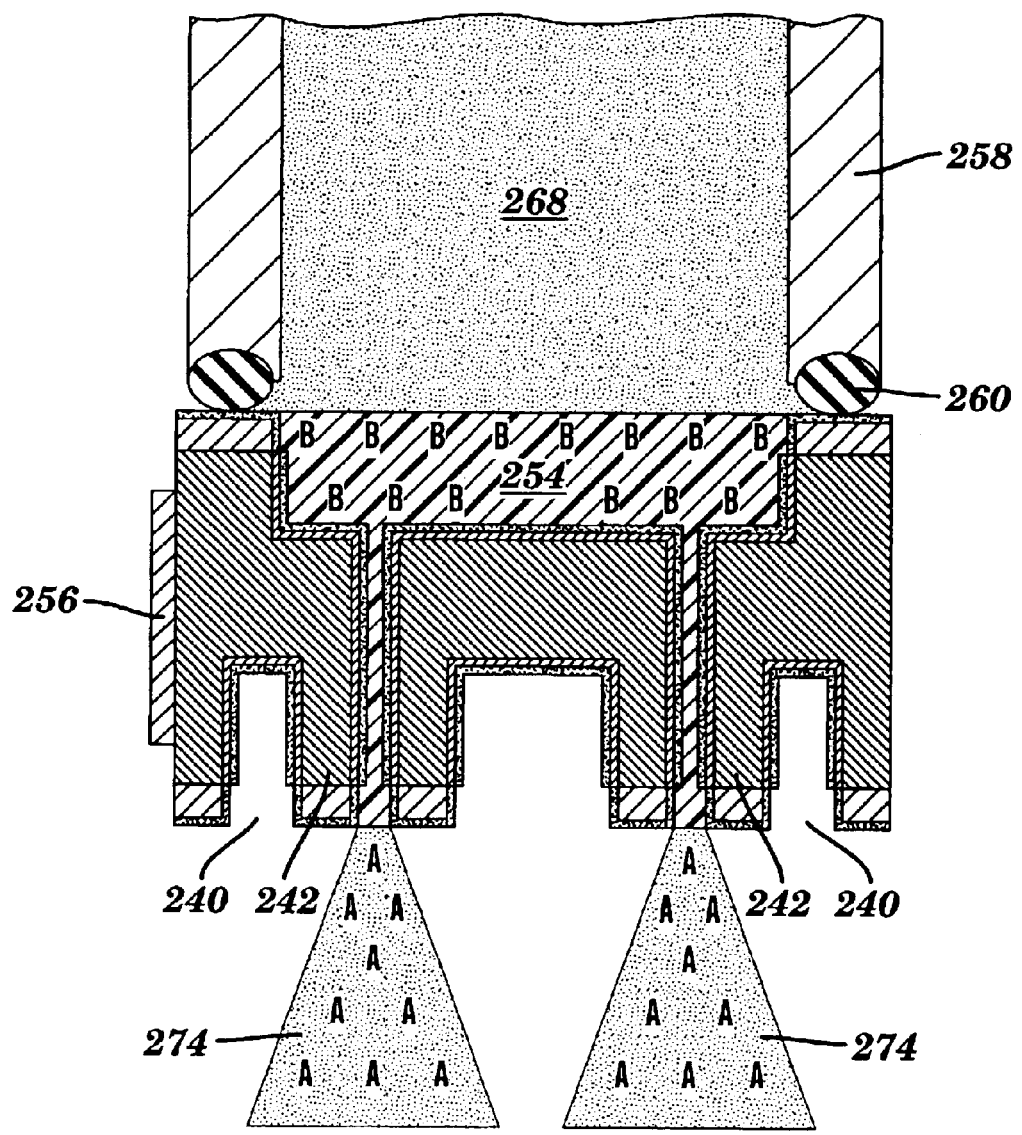
Figure 3D:
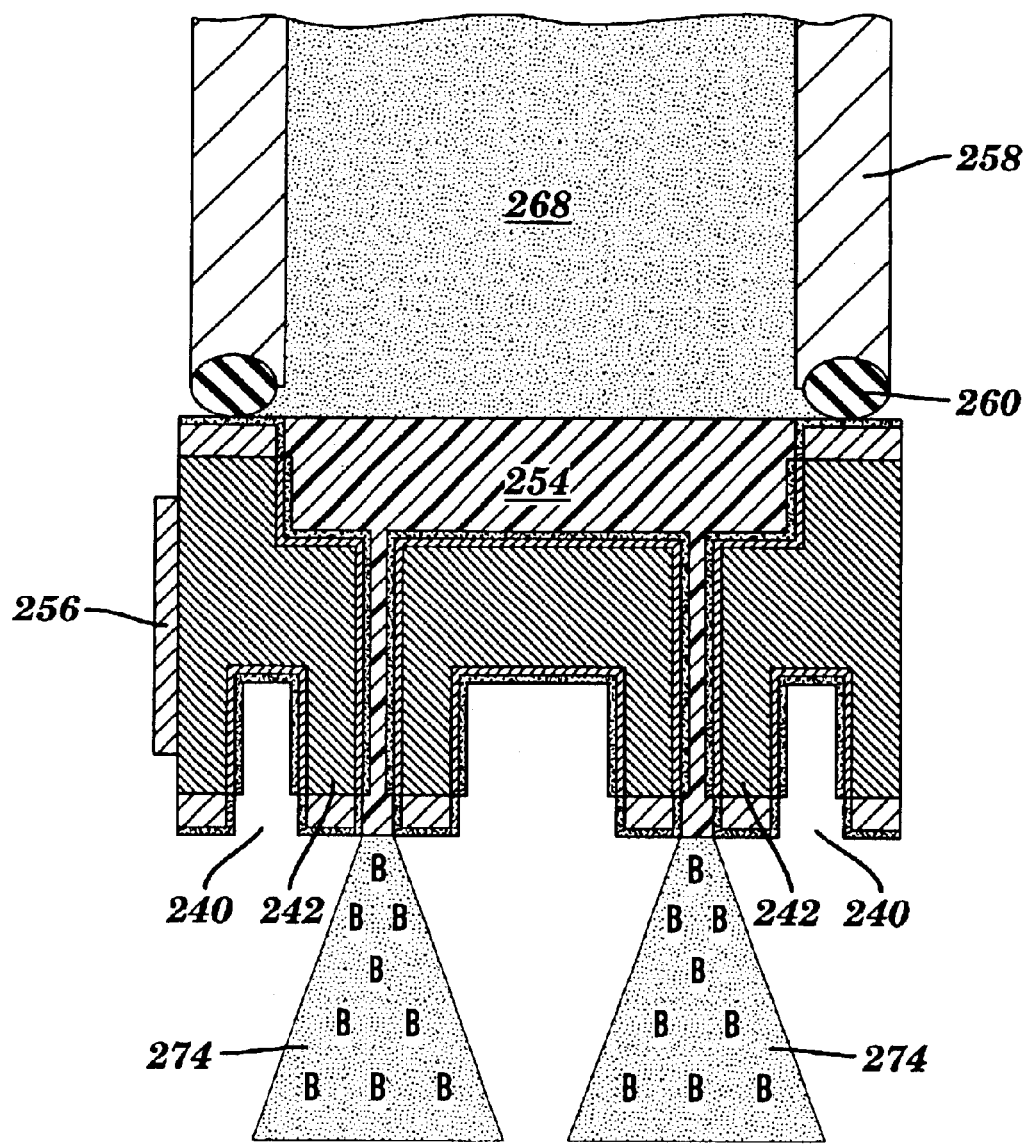

FIGS. 3A–3D illustrate the loading of a larger sample volume, such as a direct interface stream, by directly sealing a fluid delivery probe to the injection surface of the polymer monolith/multiple-electrospray device of the present invention. FIG. 3A shows the loading of the sample on the polymer monolith. FIG. 3B shows an eluting solution delivered to the loaded monolith to separate and elute the analytes as shown in FIGS. 3C–3D.

Figure 4A:
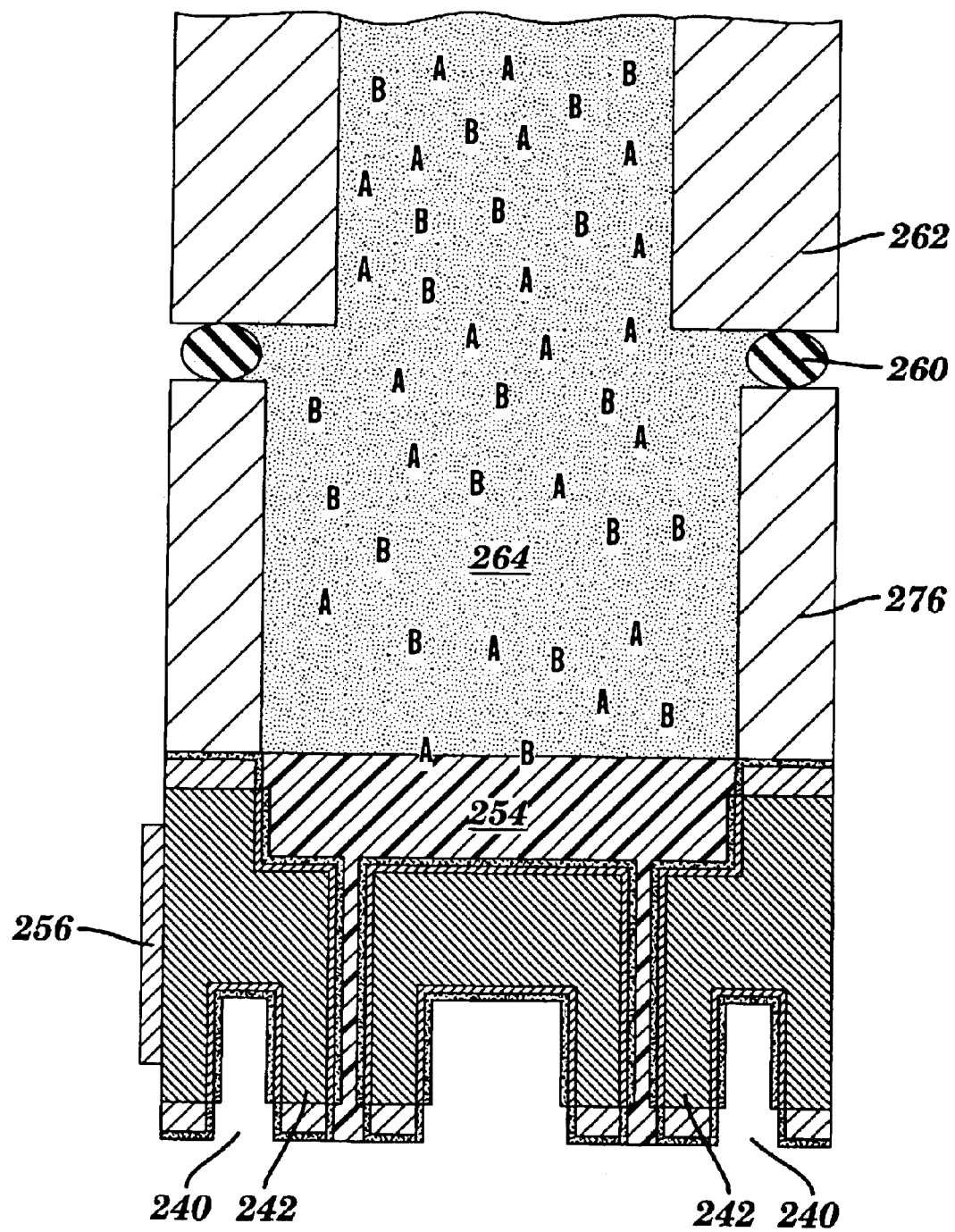
FIGS. 4A–4E show a cross-sectional view of a polymer monolith/multiple-nozzle electrospray device of the present invention bonded to a reservoir substrate. These Figures illustrate the loading of a large sample volume to a reservoir bonded to the injection side of the present invention, partition of the analytes A and B to the polymer monolith, evaporation of the sample volume, delivery of a mobile phase to the microchip via a fluid delivery device and reconstitution and liquid separation-electrospray mass spectrometry analysis of the analytes A and B.
Figure 4B:
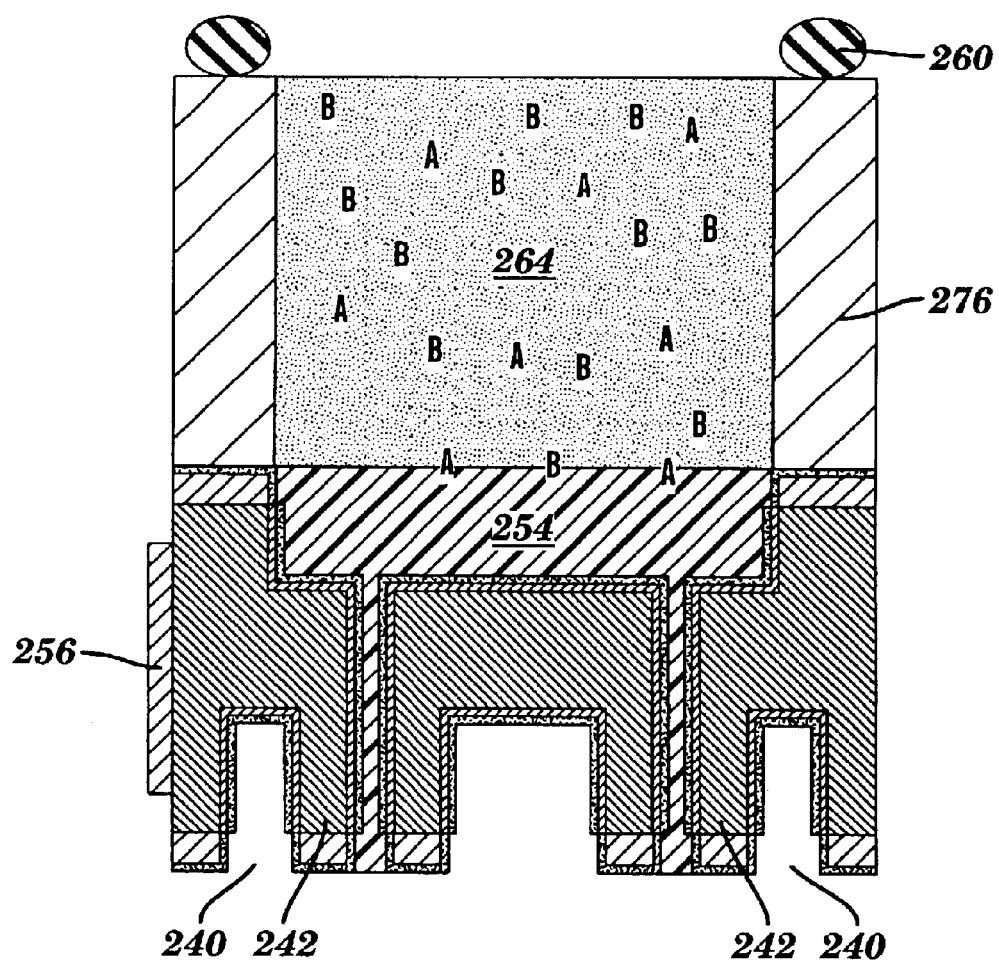
Figure 4C:
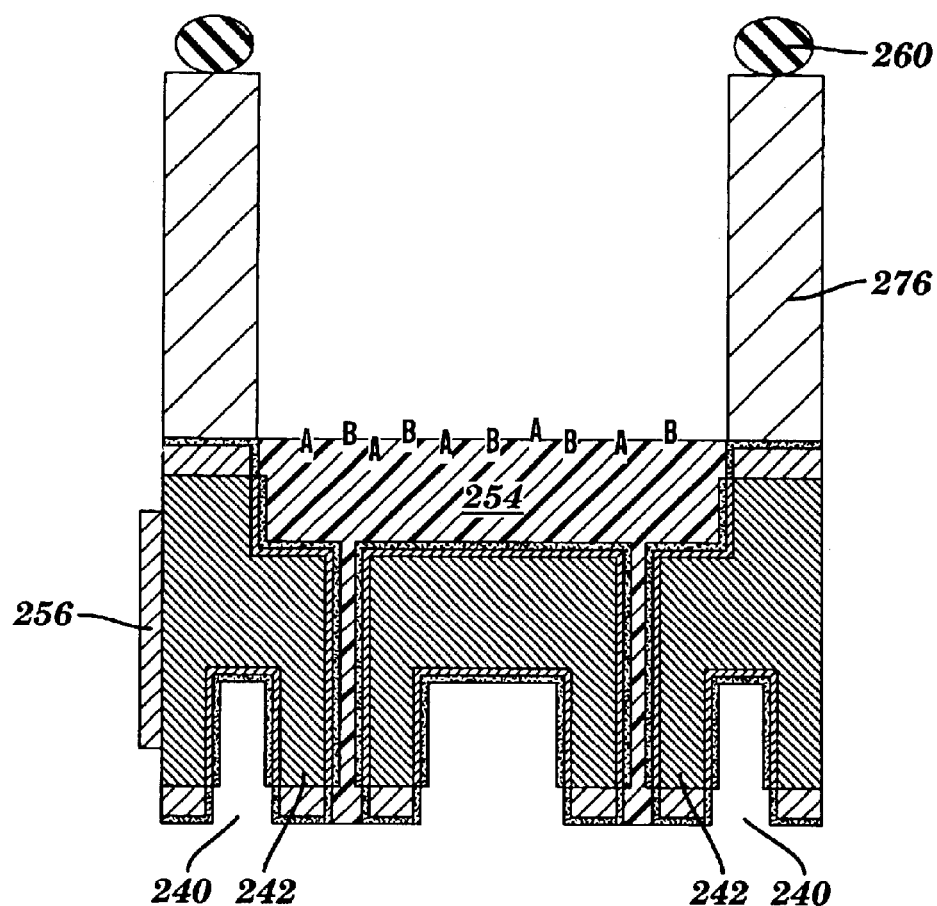
Figure 4D:
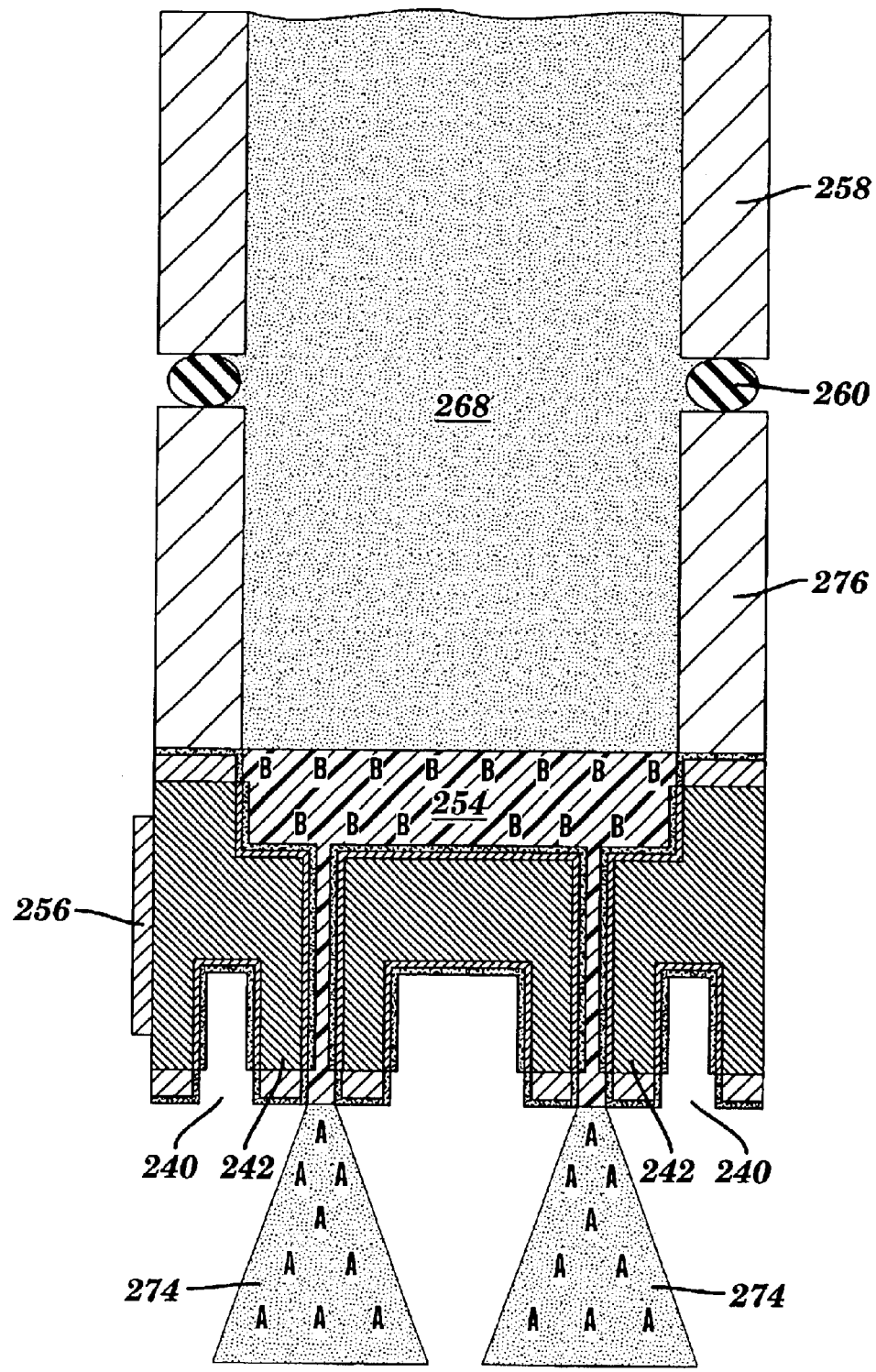
Figure 4E:
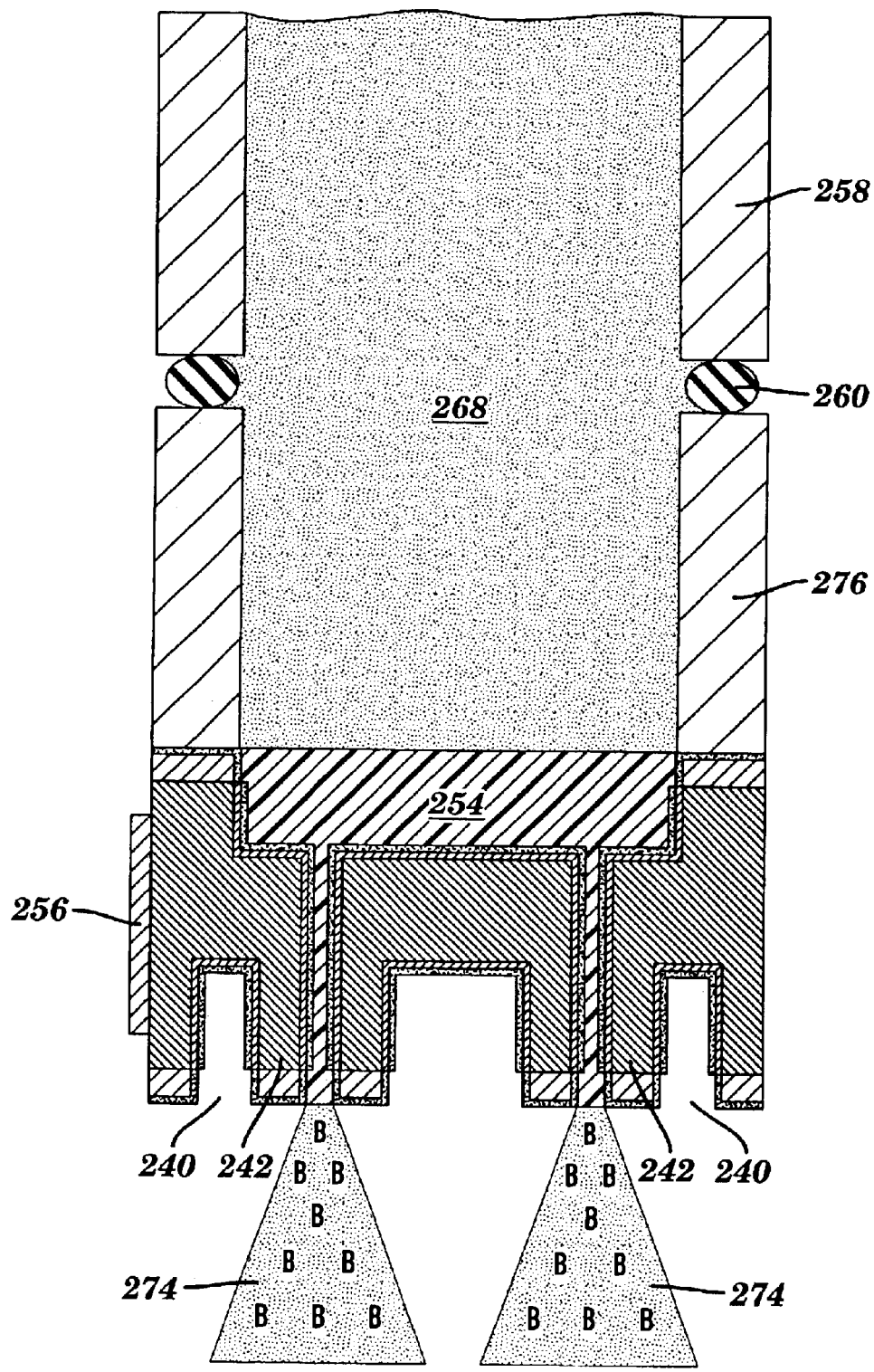

FIGS. 4A–E illustrates a reservoir 276 bonded to the injection side of the device for acceptance of higher fluid volumes. FIG. 4A shows the loading of a larger sample volume 264 by directly sealing a fluid delivery probe 262 to the reservoir 276 on the injection surface of the polymer monolith/multiple-electrospray device of the present invention. The analyte molecules A & B will partition onto the polymer monolith 254 as shown in FIGS. 4B–4C. FIG. 4D shows a fluid delivery device 258 incorporating a seal 260 to the injection side of the device 250 used to deliver a solution 268 suitable to elute the analytes A & B through the polymer monolith 254 for electrospray mass spectrometry analysis of the eluted analytes. FIGS. 4D–4E show an eluting solution delivered to the loaded monolith to separate and elute the analytes from the monolith.

Figure 5A:
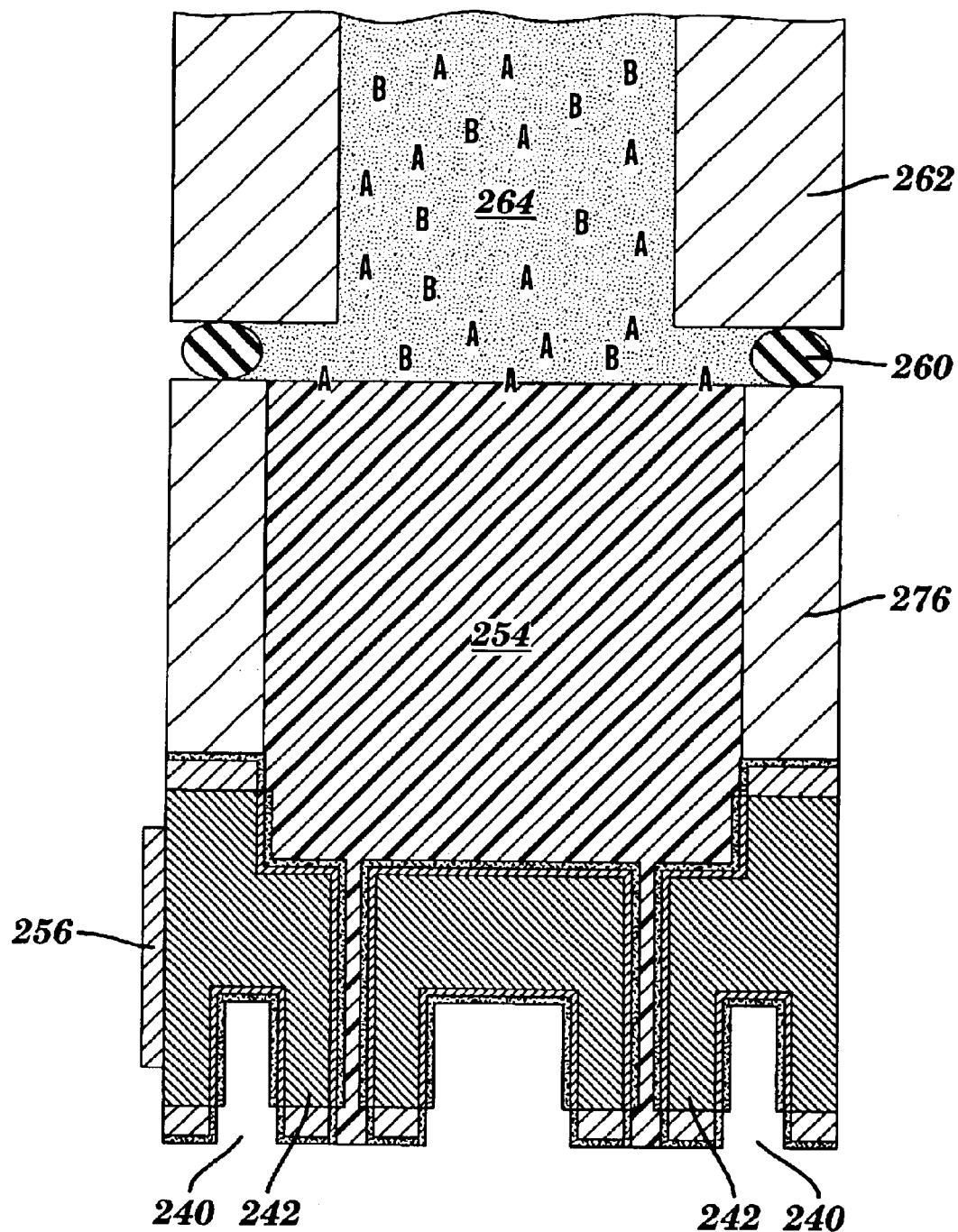
FIGS. 5A–5D show a cross-sectional view of a polymer monolith/multiple-nozzle electrospray device of the present invention bonded to a reservoir substrate wherein the polymer monolith is contained within the reservoir and the microchip. These Figures illustrate the loading of a large sample volume the polymer monolith, evaporation of the sample volume, delivery of a mobile phase to the microchip via a fluid delivery device and reconstitution and liquid separation-electrospray mass spectrometry analysis of the analytes A and B.
Figure 5B:
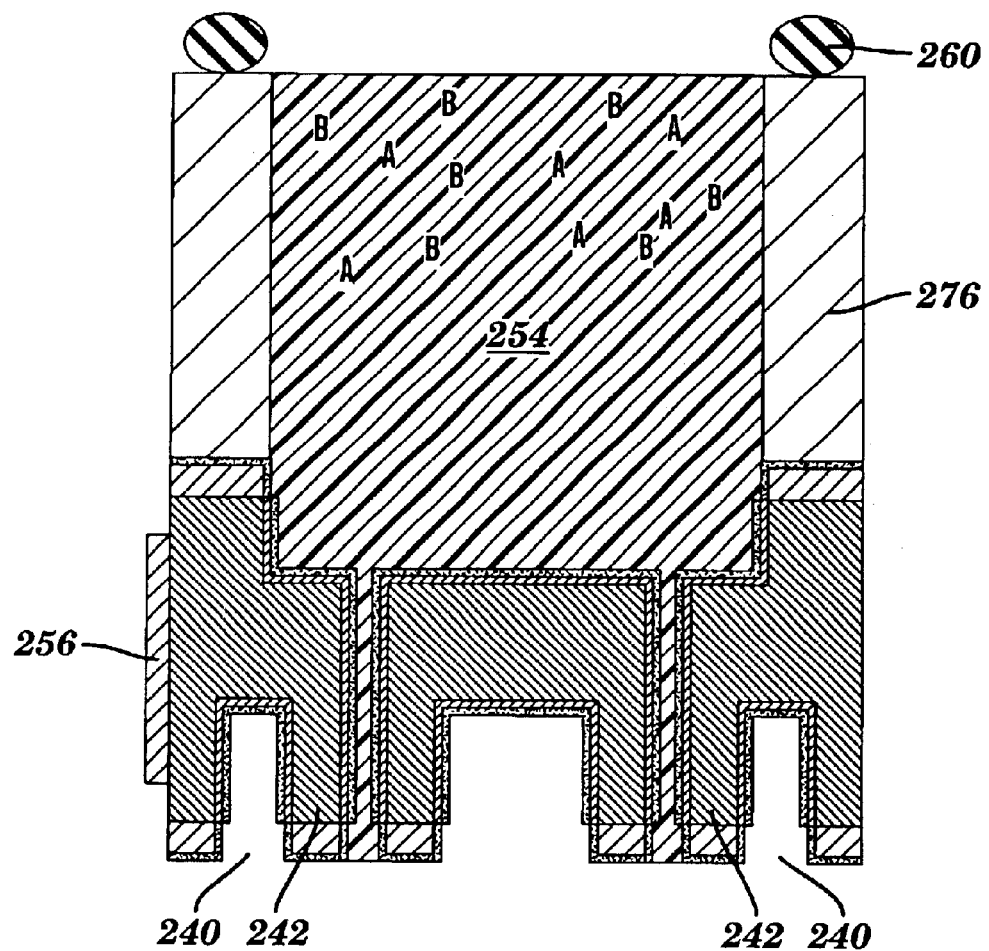
Figure 5C:
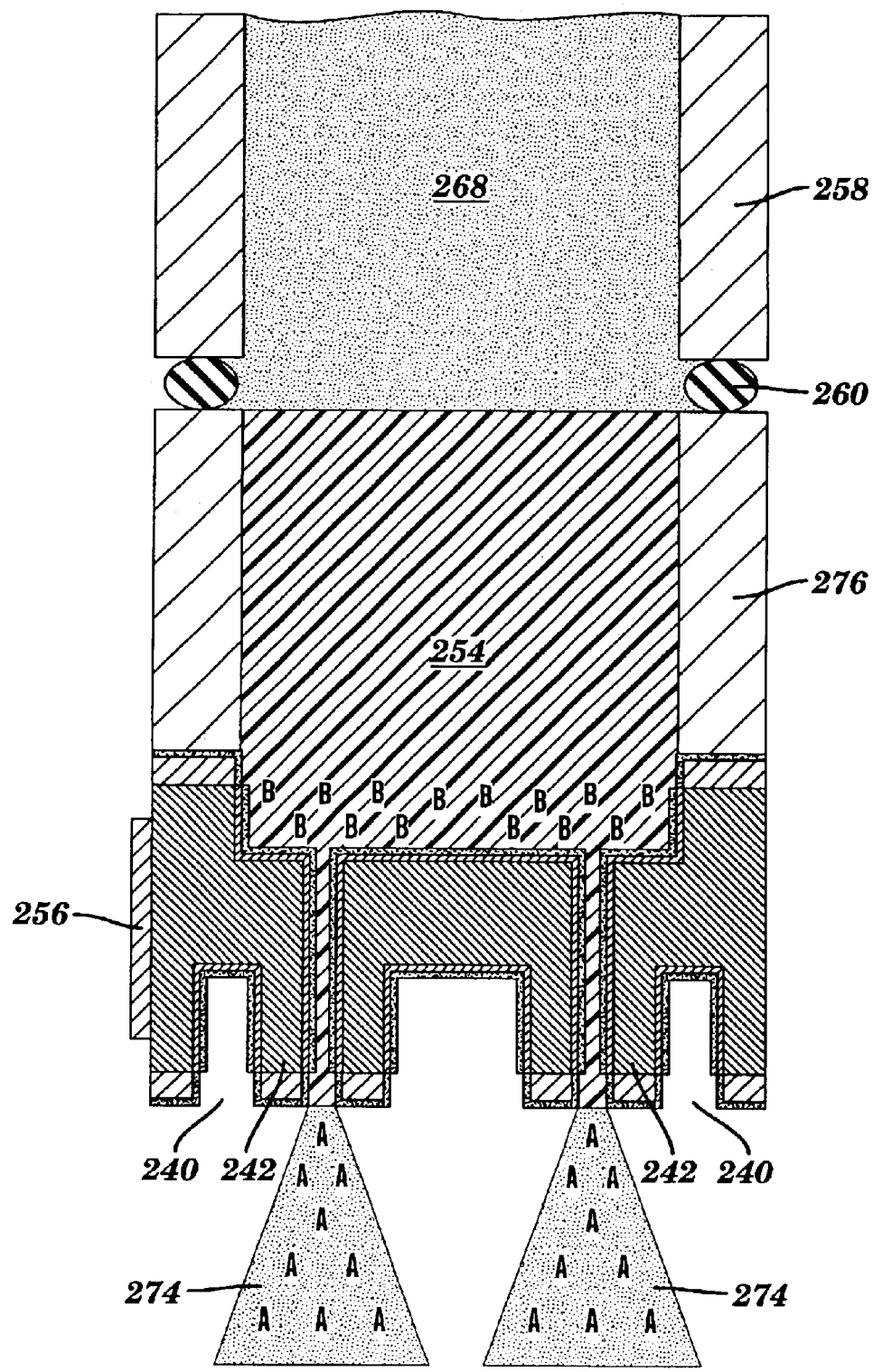
Figure 5D:
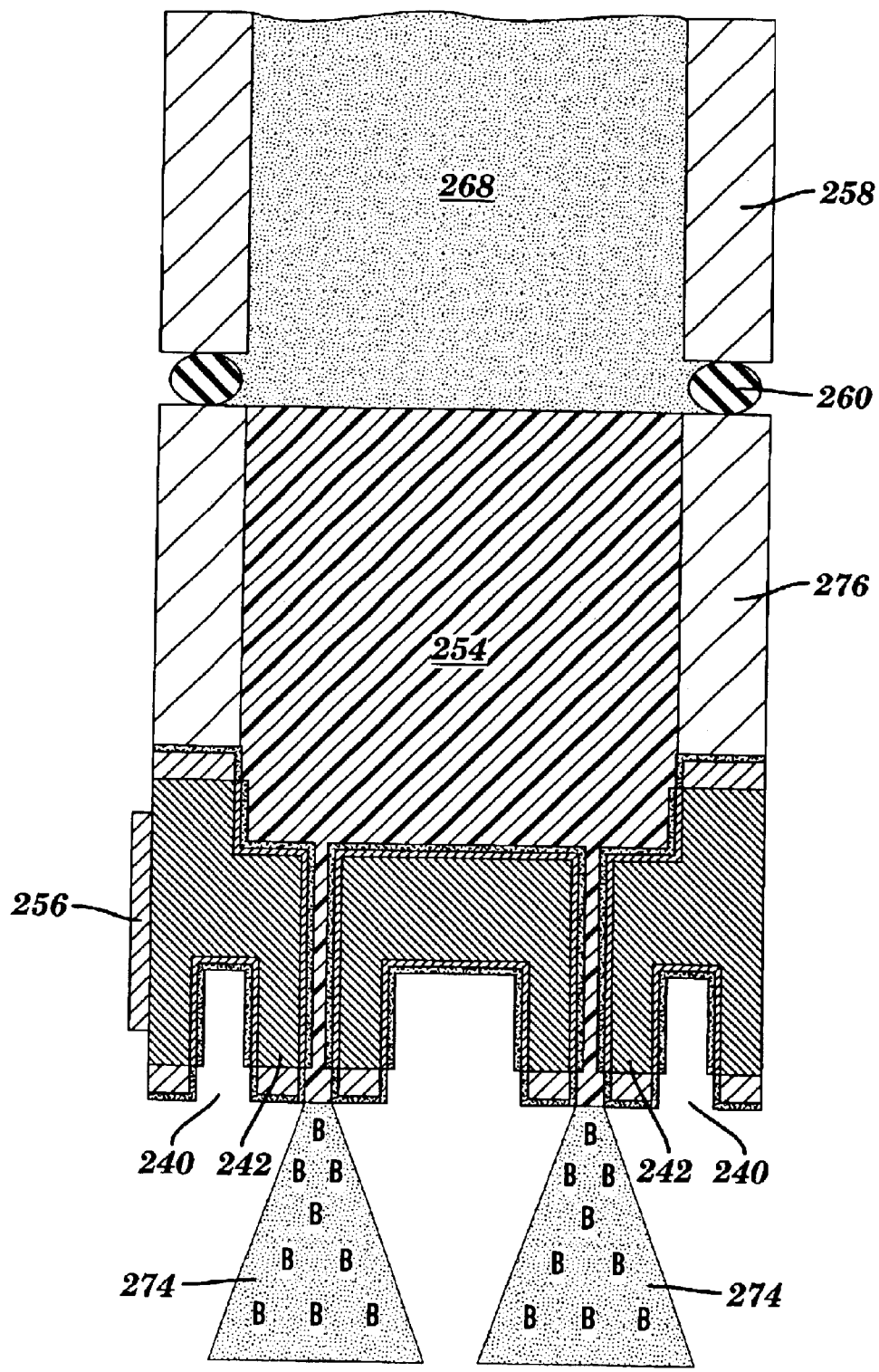

FIGS. 5A–D show the reservoir 276 also containing polymer monolith to increase the length of the separation bed for these through-substrate separations. FIG. 5A shows the loading of a larger sample volume 264 by directly sealing a fluid delivery probe 262 to the reservoir 276 on the injection surface of the polymer monolith/multiple-electrospray device of the present invention. The analyte molecules A & B will partition onto the polymer monolith 254 as shown in FIG. 5B. FIG. 5D shows a fluid delivery device 258 incorporating a seal 260 to the injection side of the device 250 used to deliver a solution 268 suitable to elute the analytes A & B through the polymer monolith 254 for electrospray mass spectrometry analysis of the eluted analytes. FIGS. 5C–5D show an eluting solution delivered to the loaded monolith to separate and elute the analytes from the monolith.

Figure 6A:
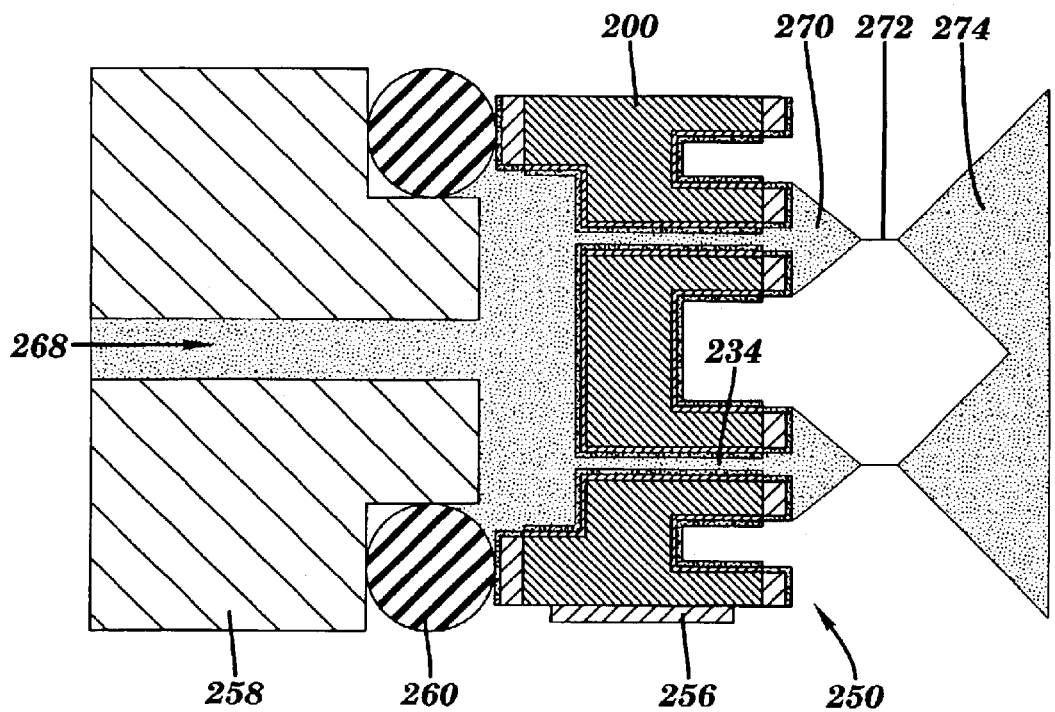
FIG. 6A shows a cross-sectional view of a two-nozzle electrospray device of the present invention generating one electrospray plume from each nozzle.
Figure 6B:
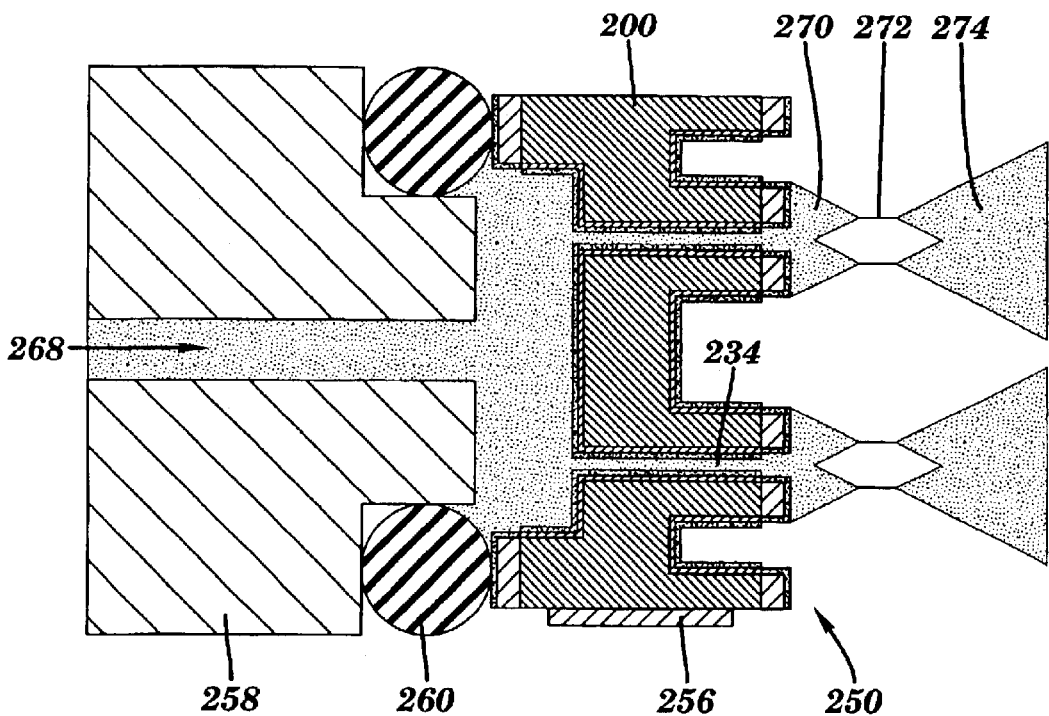
FIG. 6B shows a cross-sectional view of a two-nozzle electrospray device of the present invention generating two electrospray plumes from each nozzle.
Figure 7A:
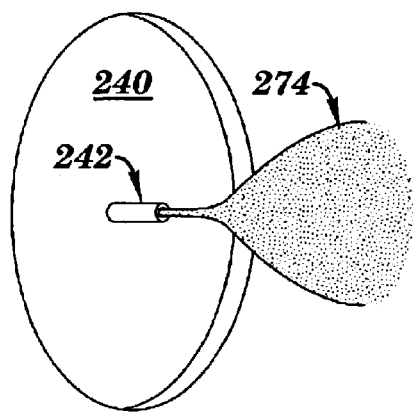
FIG. 7A shows a perspective view of a one-nozzle electrospray device of the present invention generating one electrospray plume from one nozzle.
Figure 7B:
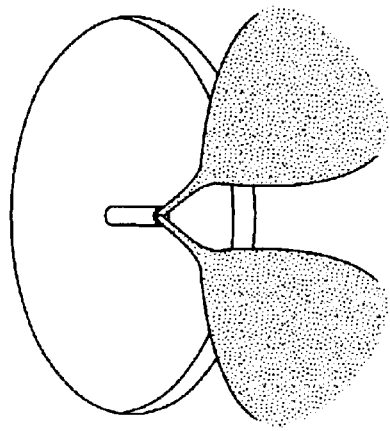
FIG. 7B shows a perspective view of a, one-nozzle electrospray device of the present invention generating two electrospray plumes from one nozzle.
Figure 7C:
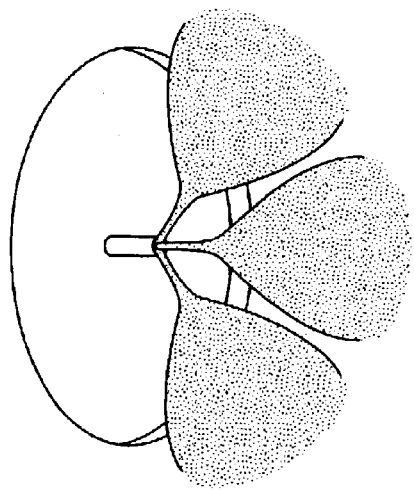
FIG. 7C shows a perspective view of a one-nozzle electrospray device of the present invention generating three electrospray plumes from one nozzle.
Figure 7D:
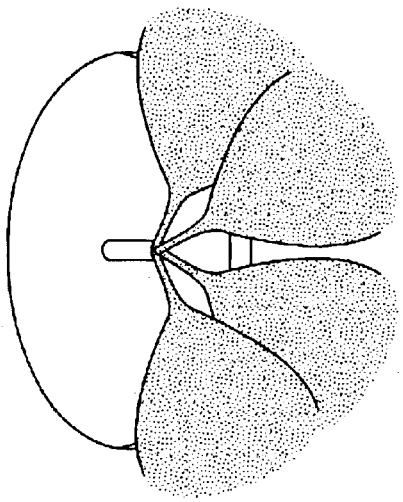
FIG. 7D shows a perspective view of a one-nozzle electrospray device of the present invention generating four electrospray plumes from one nozzle.

FIG. 6 shows a cross-sectional view of a two-nozzle array of the present invention. As shown in FIG. 6, to generate an electrospray, fluid 268 may be delivered to the through-substrate channel 234 of the device 250 by a conduit 258, for example, such as a capillary, micropipette, or microchip. The fluid 268 is subjected to a potential voltage in the conduit 258 or in the reservoir 232 or via an electrode provided on the reservoir surface (not shown) and isolated from the surrounding surface region and the substrate 200. A potential voltage may also be applied to the silicon substrate via the electrode 256 on the edge of the silicon substrate 200 the magnitude of which is preferably adjustable for optimization of the electrospray characteristics. The fluid flows through the channel 234 and exits from the nozzle 242 in the form of a Taylor cone 270, liquid jet 272, and very fine, highly charged fluidic droplets 274. FIG. 6A shows a cross-sectional view of a 2 nozzle electrospray device generating one electrospray plume from each nozzle for one fluid stream. FIG. 6B shows a cross-sectional view of a 2 nozzle electrospray device generating 2 electrospray plumes from each nozzle for one fluid stream.

The nozzle 242, shown in FIGS. 6A–B, provides the physical asperity to promote the formation of a Taylor cone 270 and efficient electrospray 274 of a fluid 268. The nozzle 242 also forms a continuation of and serves as an exit orifice of the through-substrate channel 234. The recessed annular region 240 serves to physically isolate the nozzle 242 from the surface. The present invention allows the optimization of the electric field lines emanating from the fluid 268 exiting the nozzle 242, for example, through independent control of the potential voltage of the fluid 268 and the potential voltage of the substrate 200 of each nozzle.

Figure 8B:
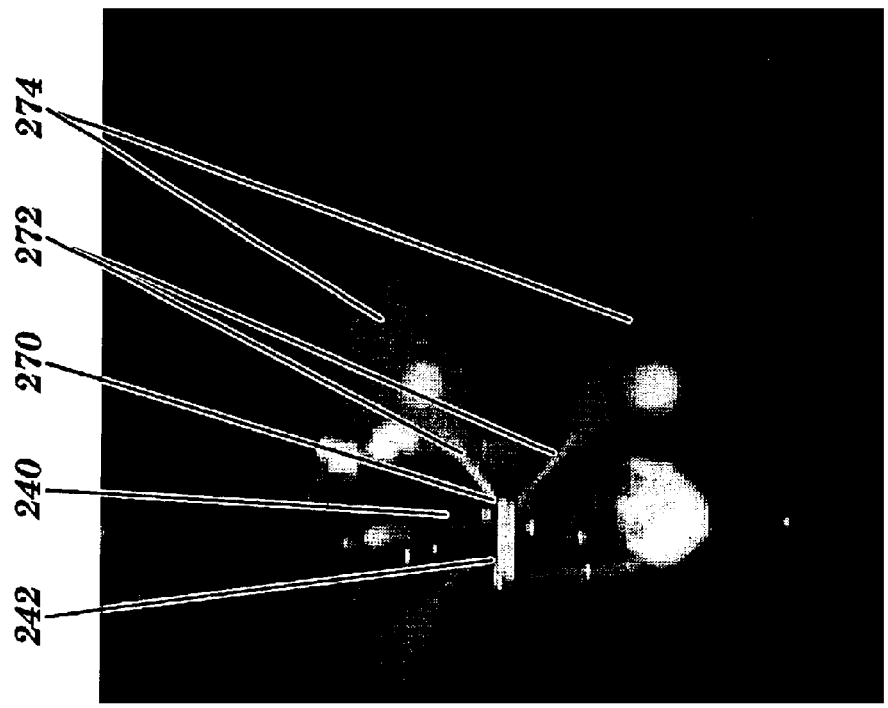
FIG. 8B shows a video capture picture of a microfabricated electrospray nozzle generating two electrospray plumes from one nozzle.
Figure 8A:
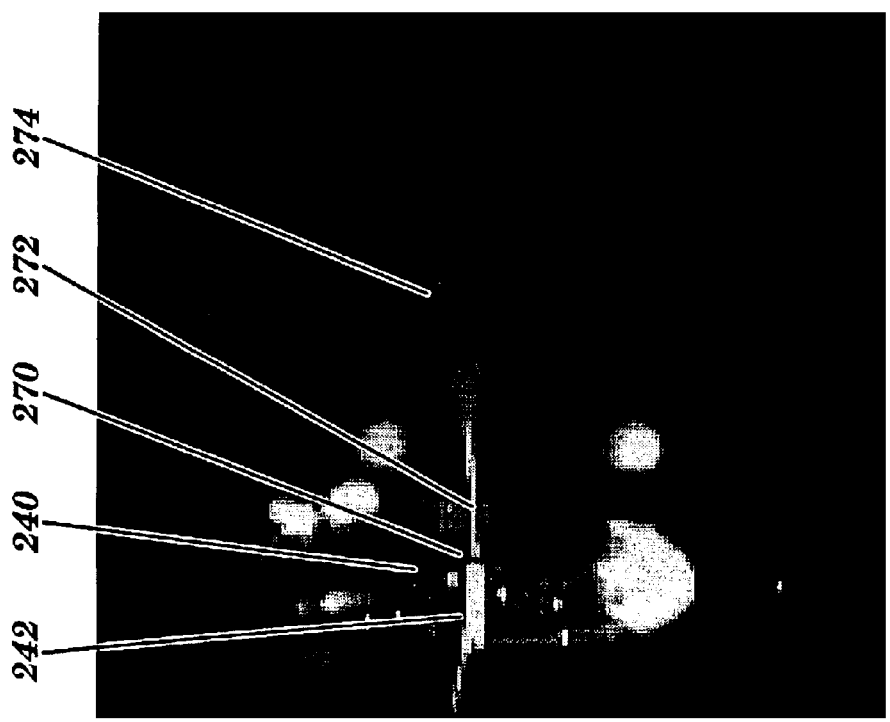
FIG. 8A shows a video capture picture of a microfabricated electrospray nozzle generating one electrospray plume from one nozzle.
Figure 9B:
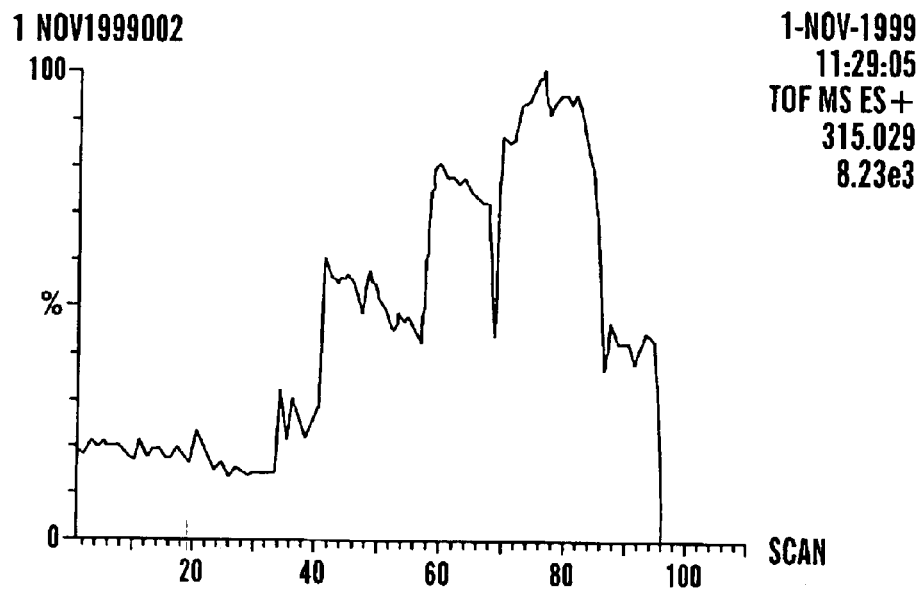
FIG. 9B shows the mass chromatogram for the protonated analyte at m/z 315. Region 1 is the resulting ion intensity from one electrospray plume from one nozzle. Region 2 is from two electrospray plumes from one nozzle. Region 3 is from three electrospray plumes from one nozzle. Region 4 is from four electrospray plumes from one nozzle. Region 5 is from two electrospray plumes from one nozzle.
Figure 9A:
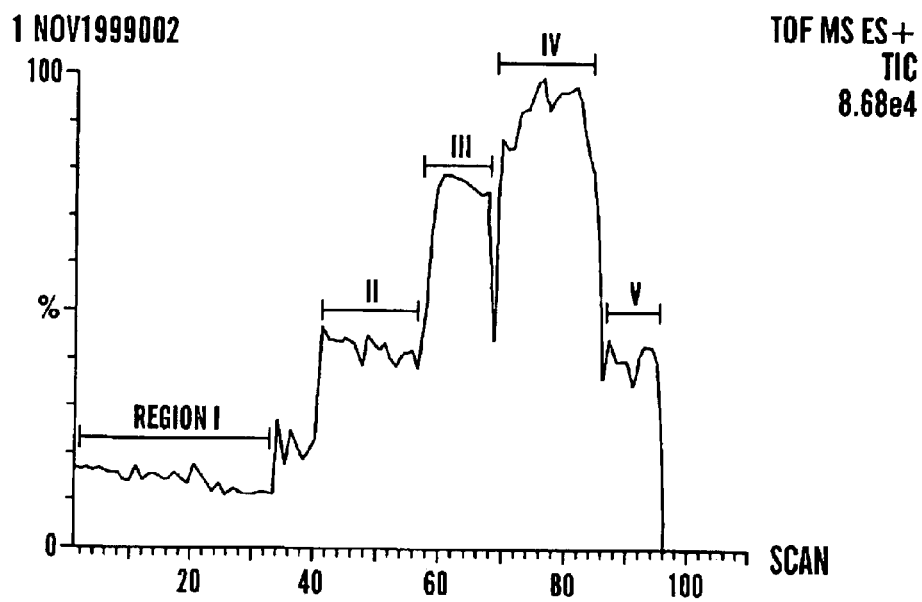
FIG. 9A shows the total ion chromatogram (TIC) of a solution undergoing electrospray from a single nozzle generating one through four electrospray plumes.

FIGS. 7A–7D illustrate 1, 2, 3 and 4 electrospray plumes, respectively, generated from one nozzle 242. FIGS. 8A–8B show video capture pictures of a microfabricated electrospray device of the present invention generating one electrospray plume from one nozzle and two electrospray plumes from one nozzle, respectively. FIG. 9 shows mass spectral results acquired from a microfabricated electrospray device of the present invention generating from 1 to 4 electrospray plumes from a single nozzle. The applied fluid potential voltage relative to the applied substrate potential voltage controls the number of electrospray plumes generated. FIG. 9A shows the total ion chromatogram ("TIC") of a solution containing an analyte at a concentration of 5 $\mu$M resulting from electrospray of the fluid from a microfabricated electrospray device of the present invention. The substrate voltage for this example is held at zero V while the fluid voltage is varied to control the number of electrospray plumes exiting the nozzle. FIG. 9B shows the selected mass chromatogram for the analyte at m/z 315. In this example, Region I has one electrospray plume exiting the nozzle tip with a fluid voltage of 950V. Region II has two electrospray plumes exiting the nozzle tip with a fluid voltage of 1050V. Region III has three electrospray plumes exiting the nozzle tip with a fluid voltage of 1150 V. Region IV has four electrospray plumes exiting the nozzle tip with a fluid voltage of 1250V. Region V has two electrospray plumes exiting the nozzle tip.

Figure 10A:
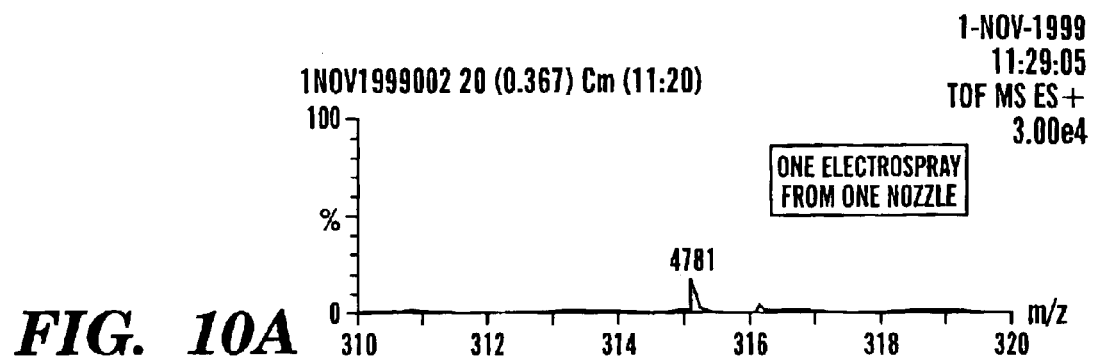
FIG. 10A shows the mass spectrum from region I.
Figure 10B:
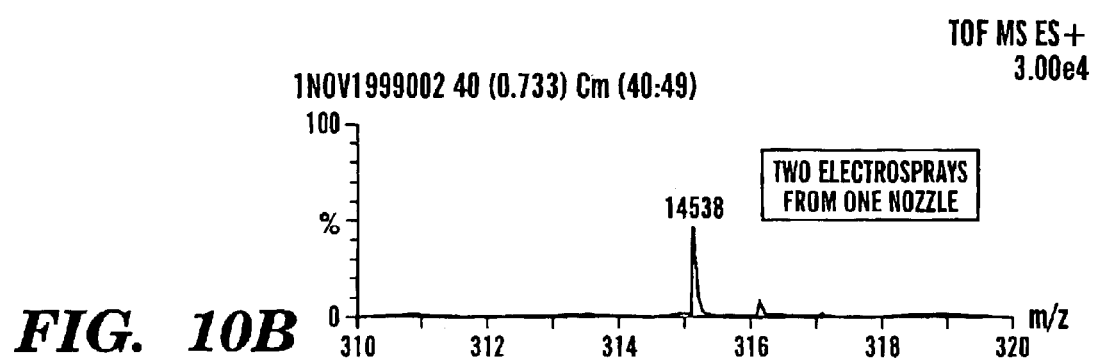
FIG. 10B shows the mass spectrum from region II.
Figure 10C:
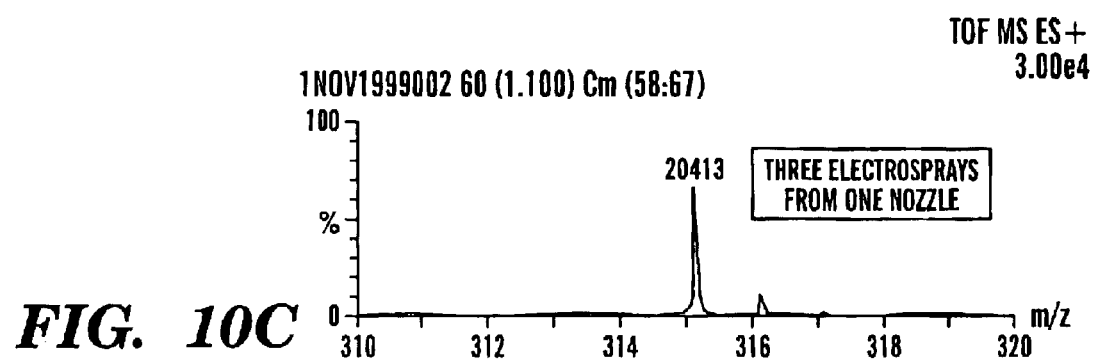
FIG. 10C shows the mass spectrum from region III.
Figure 10D:
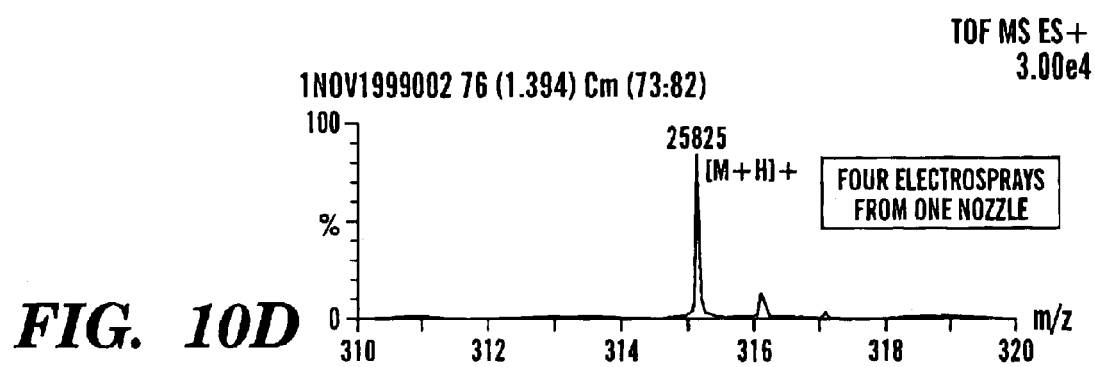
FIG. 10D shows the mass spectrum from region IV.
Figure 11:
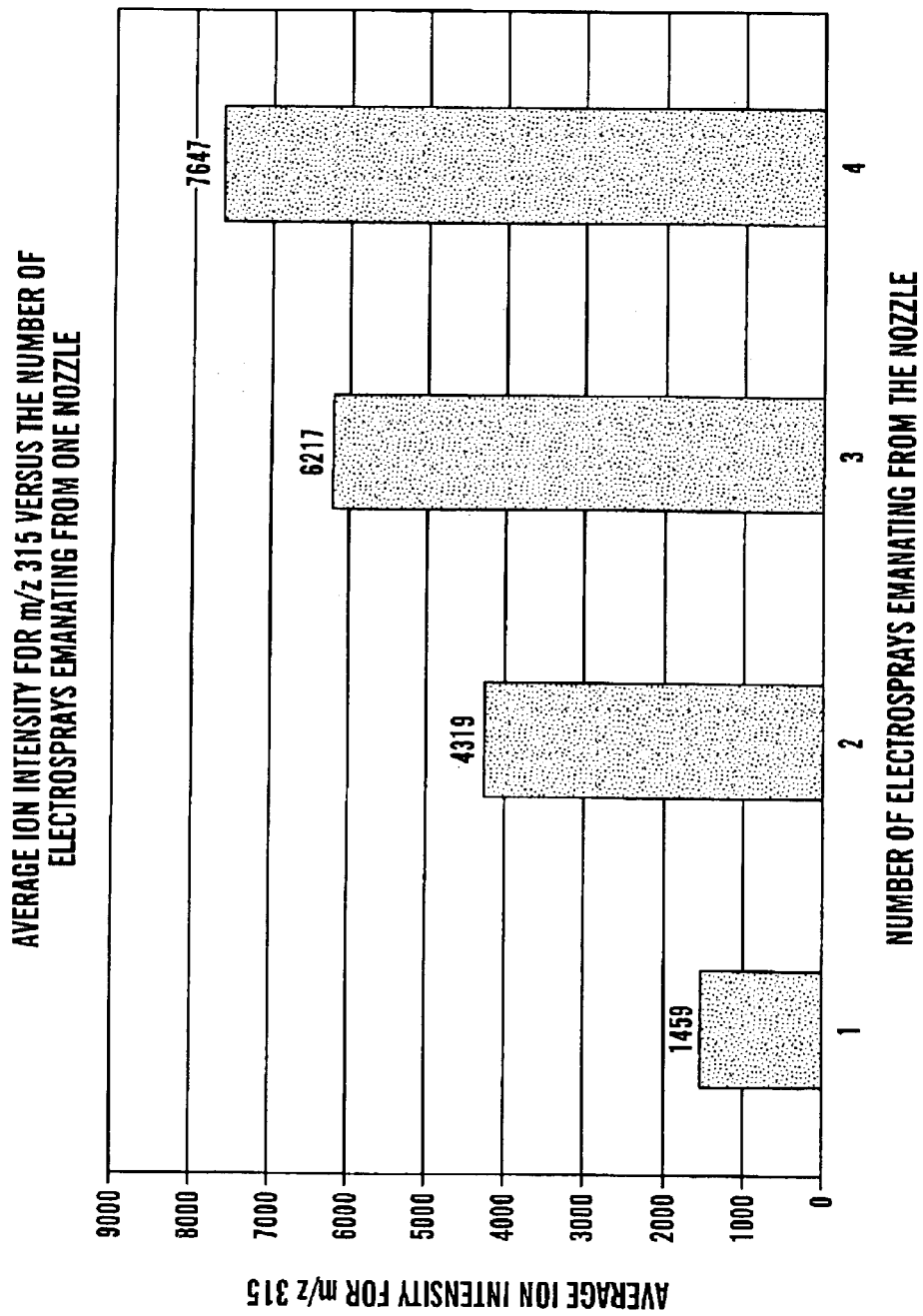
FIG. 11 is a chart of the ion intensity for m/z 315 versus the number of electrospray plumes emanating from one nozzle.

FIG. 10A shows the mass spectrum resulting from Region I with one electrospray plume. FIG. 10B shows the mass spectrum resulting from Region II with two electrospray plumes. FIG. 10C shows the mass spectrum resulting from Region III with three electrospray plumes. FIG. 10D shows the mass spectrum resulting from Region IV with four electrospray plumes exiting the nozzle tip. It is clear from the results that this invention can provide an increase in the analyte response measured by a mass spectrometer proportional to the number of electrospray plumes exiting the nozzle tip. FIG. 11 charts the ion intensity for m/z 315 for 1, 2, 3 and 4 electrospray plumes exiting the nozzle tip.

Figure 12A:
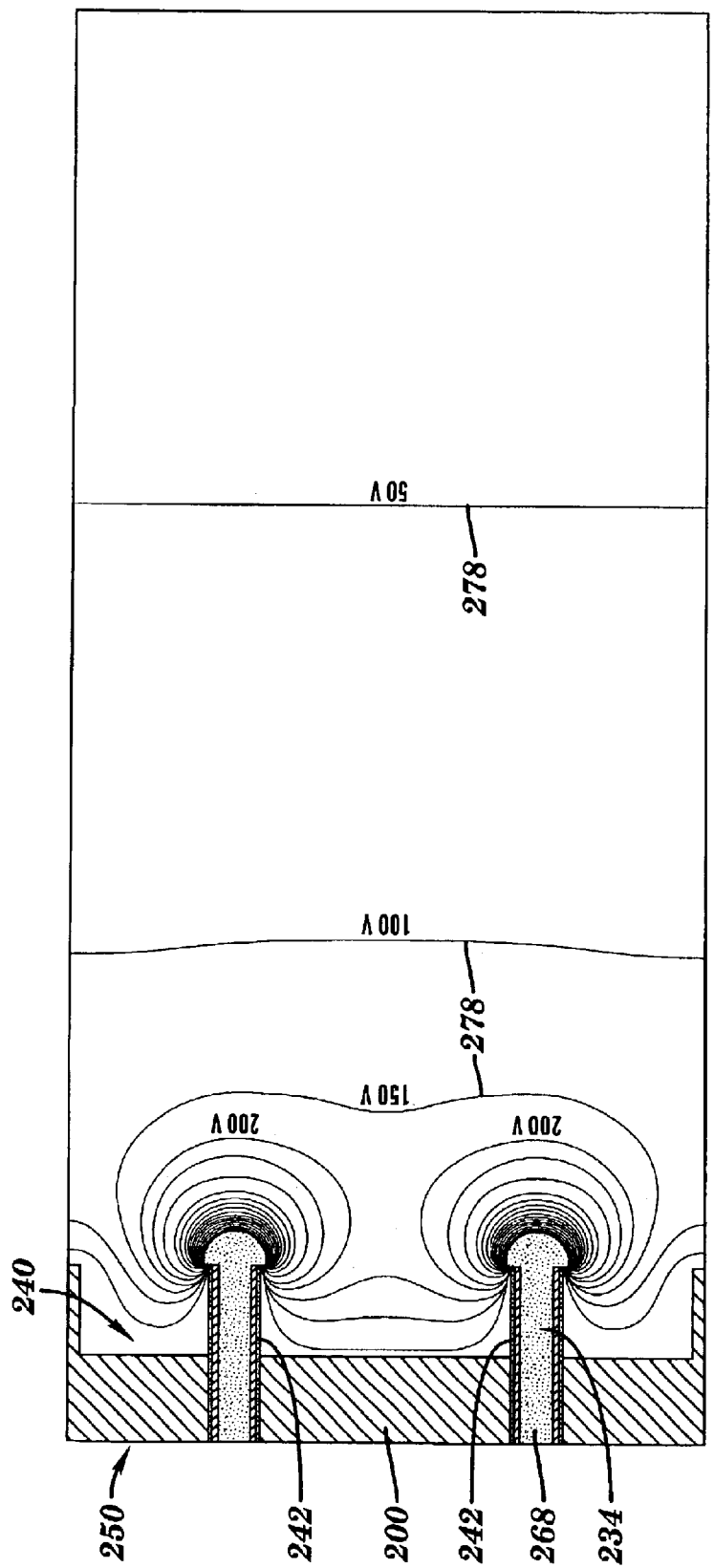
FIG. 12A is a cross-sectional view of two adjacent 20 gm diameter nozzles with heights of 50 $\mu$m. The nozzles are 120 $\mu$m center-to-center spaced. The fluid has a voltage of 1000V, substrate has a voltage of zero V and a third electrode (not shown due to the scale of the figure) is located 5 mm. from the substrate and has a 10 voltage of zero V. The equipotential field lines are shown in increments of 50 V.
Figure 12B:
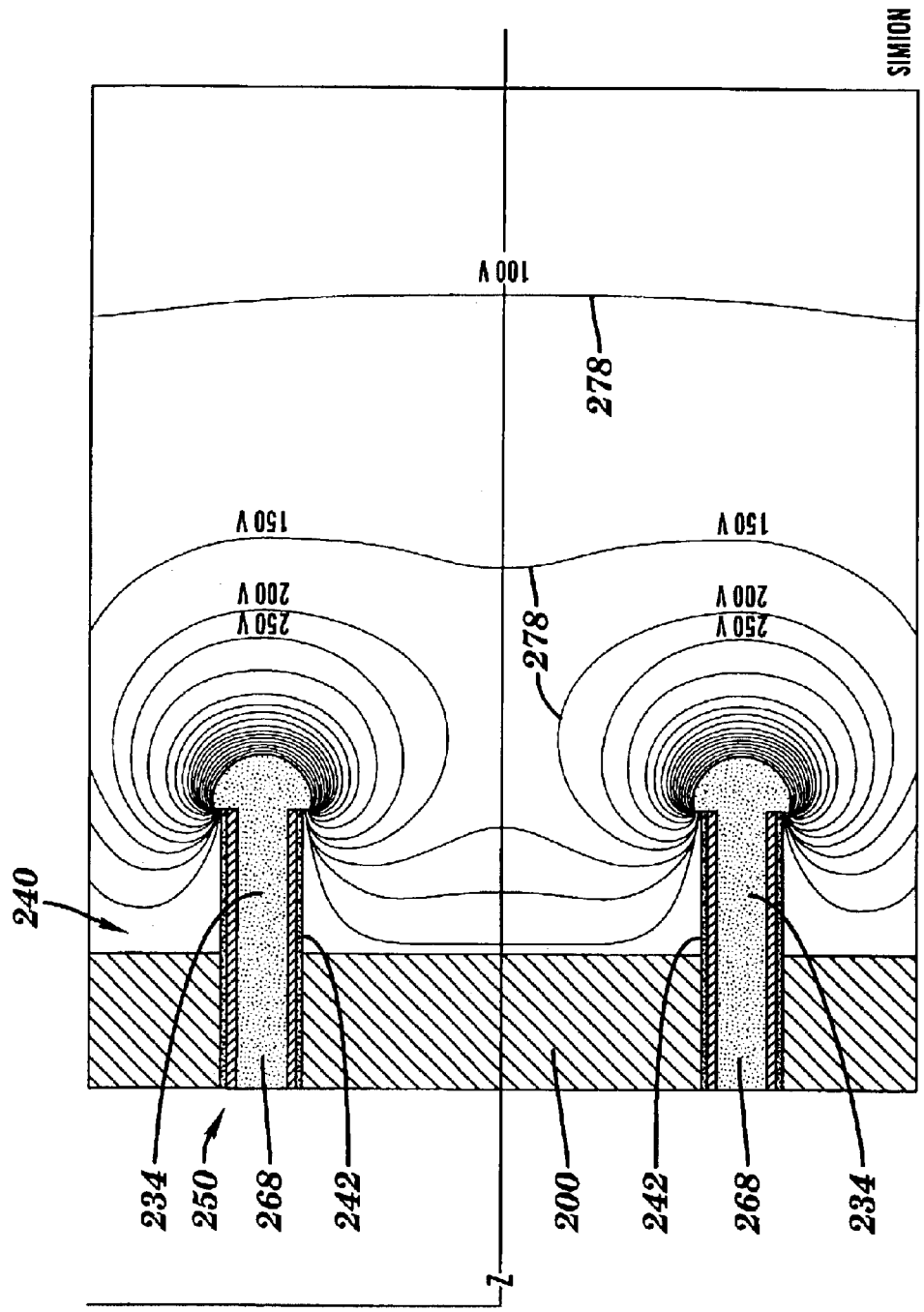
FIG. 12B is an expanded region around the nozzles shown in FIG. 11A.
Figure 12C:
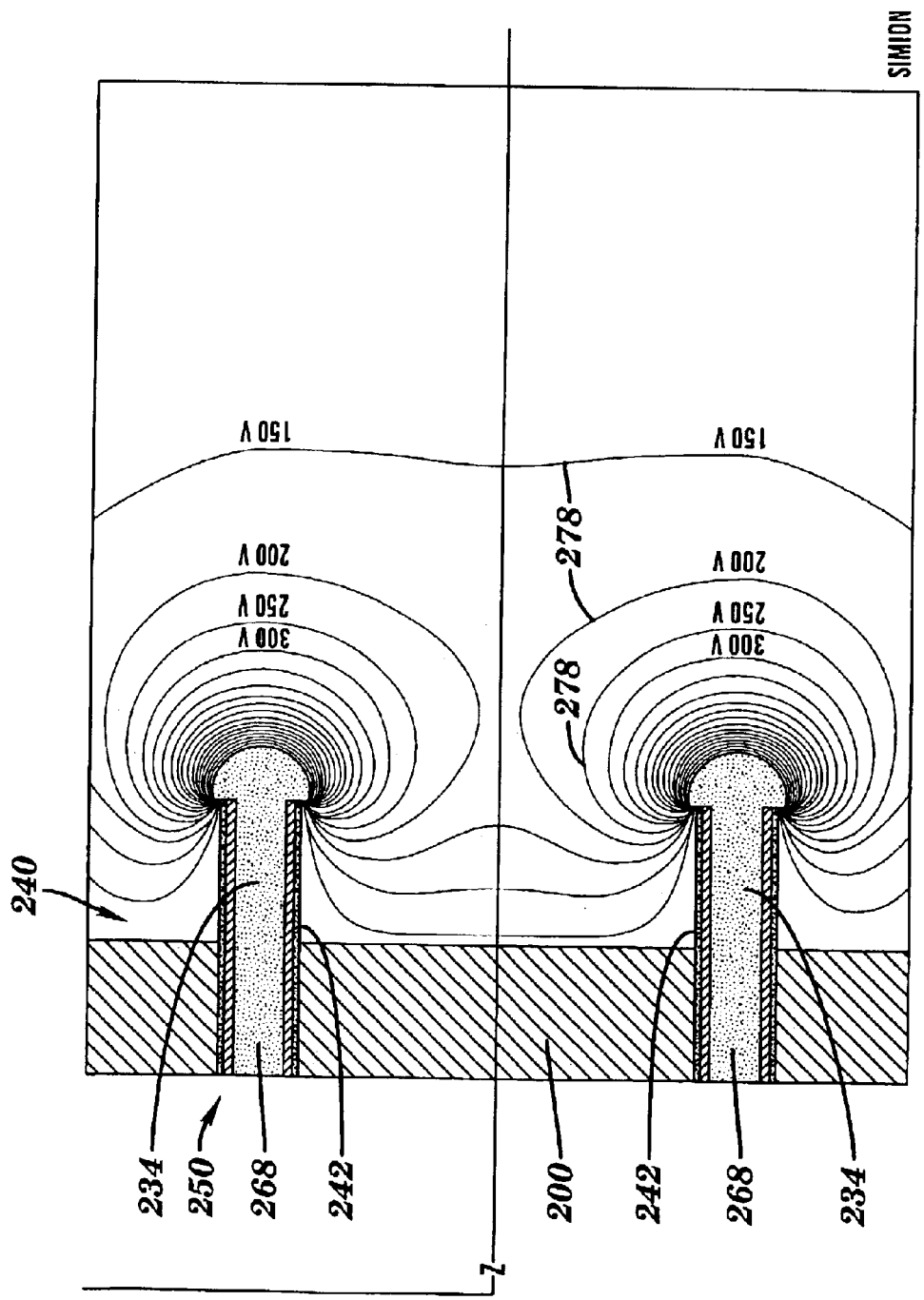
FIG. 12C is a cross-sectional view of two adjacent 20 $\mu$m, diameter nozzles with heights of 50 $\mu$m. The fluid has a voltage of 1000V, substrate has a voltage of zero V and a third electrode (not shown due to the scale of the figure) is located 5 mm. from the substrate and has a voltage of 800 V. The equipotential field lines are shown in increments of 50 V.
Figure 12D:
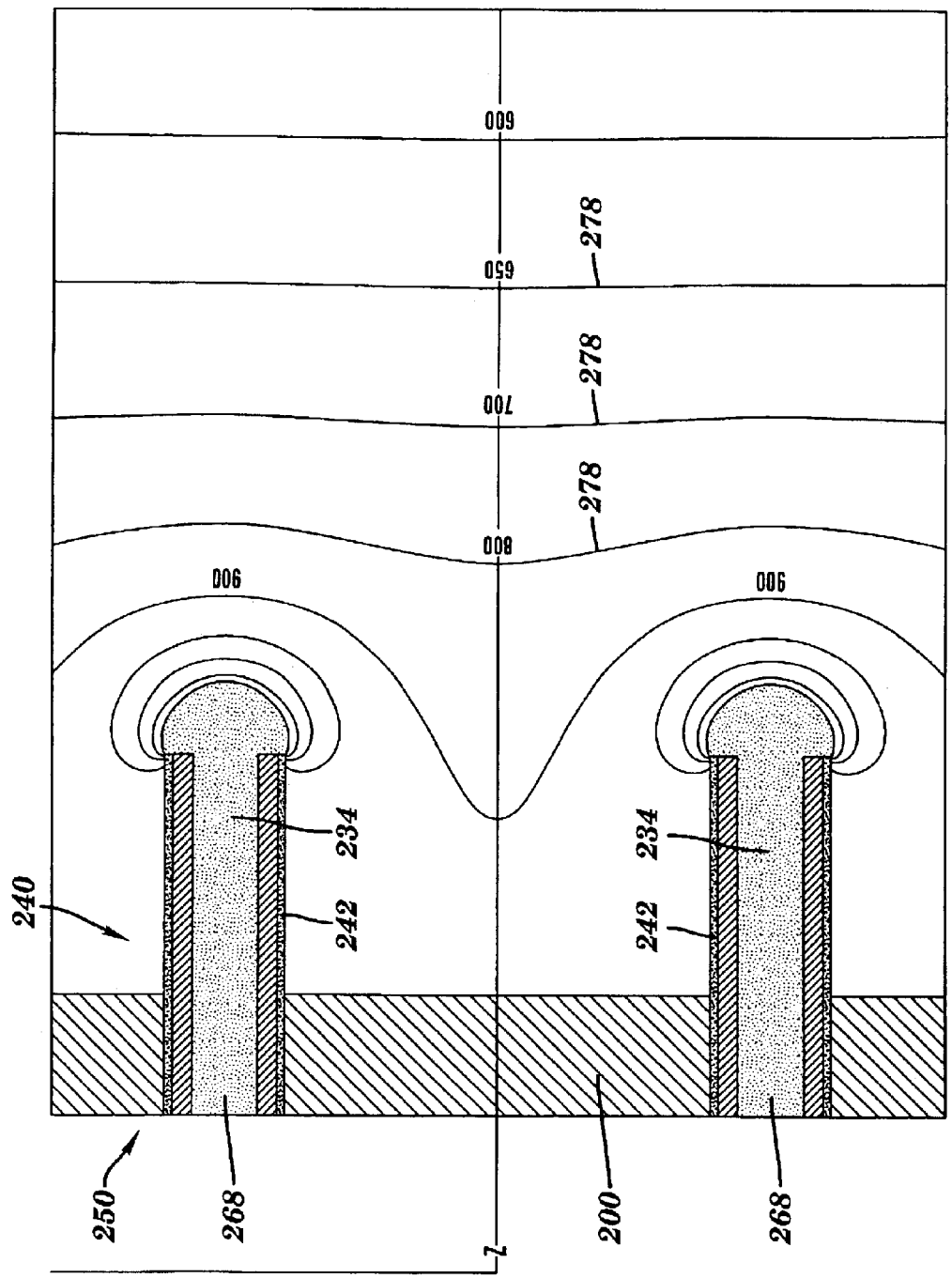
FIG. 12D is a cross-sectional view of two adjacent 20 $\mu$m diameter nozzles with heights of 50 $\mu$m. The fluid has a voltage of 1000V, substrate has a voltage of 800 V and a third electrode (not shown due to the scale of the figure) is located 5 mm from the substrate and has a voltage of zero V. The equipotential field lines are shown in increments of 50 V.

The electric field at the nozzle tip can be simulated using SIMION™ ion optics software. SIMION™ allows for the simulation of electric field lines for a defined array of electrodes. FIG. 12A shows a cross-sectional view of two 20 $\mu$m diameter nozzles 242 with a nozzle height of 50 $\mu$m and separated by 120 $\mu$m center-to-center. A fluid 268 flowing through the nozzles 242 and exiting the nozzle tips in the shape of a hemisphere has a potential voltage of 1000V. The substrate 200 has a potential voltage of zero volts. A simulated third electrode (not shown in the figure due to the scale of the drawing) is located 5 mm from the nozzle side of the substrate and has a potential voltage of zero volts. This third electrode is generally an ion-sampling orifice of an atmospheric pressure ionization mass spectrometer. This simulates the electric field required for the formation of a Taylor cone rather than the electric field required to maintain an electrospray. FIG. 12A shows the equipotential lines 278 in 50 V increments. The closer the equipotential lines 278 are spaced the higher the electric field. The simulated electric field at the fluid tips with these dimensions and potential voltages is 8.2×10$^7$ V/m. FIG. 12B shows an expanded region around the nozzles of FIG. 12A to show greater detail of the equipotential lines 278. FIG. 12C shows the equipotential lines 278 around the nozzles 242 with a fluid potential voltage of 1000V, substrate voltage of zero V and a third electrode voltage of 800 V. The electric field at the nozzle tip is 8.0×10$^7$ V/m indicating that the applied voltage of this third electrode has little effect on the electric field at the nozzle tips. FIG. 12D shows the electric field lines 278 around the nozzles 242 with a fluid potential voltage of 1000V, substrate voltage of 800 V and a third electrode voltage of 0 V. The electric field at the nozzle tips is reduced significantly to a value of 2.2×10$^7$ V/m. This indicates that very fine control of the electric field at the nozzle tips is achieved with this invention by independent control of the applied fluid and substrate voltages and is relatively insensitive to other electrodes placed up to 5 mm from the device. This level of control of the electric field at the closely positioned nozzle tips is of significant importance for electrospray of fluids from nozzles co-planar with the surface of a substrate. Accordingly, a nozzle can be provided having a discrete electric field which is not subject to interference from another closely positioned nozzle.

The fine control of the electric field allows for precise control of the electrospray of fluids from these nozzles. When electrospraying fluids from this invention, this fine control of the electric field allows for a controlled formation of multiple Taylor cones and electrospray plumes from a single nozzle. By simply increasing the fluid voltage while maintaining the substrate voltage at zero V, the number of electrospray plumes emanating from one nozzle can be stepped from one to four as illustrated in FIGS. 7 and 8.

The high electric field at the nozzle tip applies a force to ions contained within the fluid exiting the nozzle. This force pushes positively-charged ions to the fluid surface when a positive voltage is applied to the fluid relative to the substrate potential voltage. Due to the repulsive force of likely-charged ions, the surface area of the Taylor cone generally defines and limits the total number of ions that can reside on the fluidic surface. It is generally believed that, for electrospray, a gas phase ion for an analyte can most easily be formed by that analyte when it resides on the surface of the fluid. The total surface area of the fluid increases as the number of Taylor cones at the nozzle tip increases resulting in the increase in solution phase ions at the surface of the fluid prior to electrospray formation. The ion intensity will increase as measured by the mass spectrometer when the number of electrospray plumes increase as shown in the example above.

Another important feature of the present invention is that since the electric field around each nozzle is preferably defined by the fluid and substrate voltage at the nozzle tip, multiple nozzles can be located in close proximity, on the order of tens of microns. This novel feature of the present invention allows for the formation of multiple electrospray plumes from multiple nozzles of a single fluid stream thus greatly increasing the electrospray sensitivity available for microchip-based electrospray devices. Multiple nozzles of an electrospray device in fluid communication with one another not only improve sensitivity but also increase the flow rate capabilities of the device. For example, the flow rate of a single fluid stream through one nozzle having the dimensions of a 10 micron inner diameter, 20 micron outer diameter, and a 50 micron length is about 1 $\mu$L/min.; and the flow rate through 200 of such nozzles is about 200 $\mu$L/min. Accordingly, devices can be fabricated having the capacity for flow rates up to about 2 $\mu$L/min., from about 2 $\mu$L/min. to about 1 mL/min., from about 100 nL/min. to about 500 nL/min., and greater than about 2 $\mu$L/min. possible.

Arrays of multiple electrospray devices having any nozzle number and format may be fabricated according to the present invention. The electrospray devices can be positioned to form from a low-density array to a high-density array of devices. Arrays can be provided having a spacing between adjacent devices of 9 mm, 4.5 mm, 2.25 mm, 1.12 mm, 0.56 mm, 0.28 mm, and smaller to a spacing as close as about 50 $\mu$m apart, respectively, which correspond to spacing used in commercial instrumentation for liquid handling or accepting samples from electrospray systems. Similarly, systems of electrospray devices can be fabricated in an array having a device density exceeding about 5 devices/cm$^2$, exceeding about 16 devices/cm$^2$, exceeding about 30 devices/cm$^2$, and exceeding about 81 devices/cm$^2$, preferably from about 30 devices/cm$^2$ to about 100 devices/cm$^2$.

Dimensions of the electrospray device can be determined according to various factors such as the specific application, the layout design as well as the upstream and/or downstream device to which the electrospray device is interfaced or integrated. Further, the dimensions of the channel and nozzle may be optimized for the desired flow rate of the fluid sample. The use of reactive-ion etching techniques allows for the reproducible and cost effective production of small diameter nozzles, for example, a 2 $\mu$m inner diameter and 5 $\mu$m outer diameter. Such nozzles can be fabricated as close as 20 $\mu$m apart, providing a density of up to about 160,000 nozzles/cm$^2$. Nozzle densities up to about 10,000/cm$^2$, up to about 15,625/cm$^2$, up to about 27,566/cm$^2$, and up to about 40,000/cm$^2$, respectively, can be provided within an electrospay device. Similarly, nozzles can be provided wherein the spacing on the ejection surface between the centers of adjacent exit orifices of the spray units is less than about 500 $\mu$m, less than about 200 $\mu$m, less than about 100 $\mu$m, and less than about 50 $\mu$m, respectively. For example, an electrospray device having one nozzle with an outer diameter of 20 $\mu$m would respectively have a surrounding sample well 30 $\mu$m wide. A densely packed array of such nozzles could be spaced as close as 50 $\mu$m apart as measured from the nozzle center.

In one currently preferred embodiment, the silicon substrate of the electrospray device is approximately 250–500 $\mu$m in thickness and the cross-sectional area of the through-substrate channel is less than approximately 2,500 $\mu$m$^2$. Where the channel has a circular cross-sectional shape, the channel and the nozzle have an inner diameter of up to 50 $\mu$m, more preferably up to 30 $\mu$m; the nozzle has an outer diameter of up to 60 $\mu$m, more preferably up to 40 $\mu$m; and nozzle has a height of (and the annular region has a depth of) up to 100 $\mu$m. The recessed portion preferably extends up to 300 $\mu$m outwardly from the nozzle. The silicon dioxide layer has a thickness of approximately 1–4 $\mu$m, preferably 1–3 $\mu$m. The silicon nitride layer has a thickness of approximately less than 2 $\mu$m.

Furthermore, the electrospray device may be operated to produce larger, minimally-charged droplets. This is accomplished by decreasing the electric field at the nozzle exit to a value less than that required to generate an electrospray of a given fluid. Adjusting the ratio of the potential voltage of the fluid and the potential voltage of the substrate controls the electric field. A fluid to substrate potential voltage ratio approximately less than 2 is preferred for droplet formation. The droplet diameter in this mode of operation is controlled by the fluid surface tension, applied voltages and distance to a droplet receiving well or plate. This mode of operation is ideally suited for conveyance and/or apportionment of a multiplicity of discrete amounts of fluids, and may find use in such devices as ink jet printers and equipment and instruments requiring controlled distribution of fluids.

The electrospray device of the present invention includes a silicon substrate material defining a channel through the substrate between an entrance orifice on a reservoir surface and a nozzle on a nozzle surface such that the electrospray generated by the device is generally perpendicular to the nozzle surface. The nozzle has an inner and an outer diameter and is defined by an annular portion recessed from the surface. The recessed annular region extends radially from the nozzle outer diameter. The tip of the nozzle is co-planar or level with and preferably does not extend beyond the substrate surface. In this manner the nozzle can be protected against accidental breakage. The nozzle, channel, reservoir and the recessed annular region are etched from the silicon substrate by reactive-ion etching and other standard semiconductor processing techniques.

All surfaces of the silicon substrate preferably have insulating layers to electrically isolate the liquid sample from the substrate such that different potential voltages may be individually applied to the substrate and the liquid sample. The insulating layers can constitute a silicon dioxide layer combined with a silicon nitride layer. The silicon nitride layer provides a moisture barrier against water and ions from penetrating through to the substrate causing electrical breakdown between a fluid moving in the channel and the substrate. The electrospray apparatus preferably includes at least one controlling electrode electrically contacting the substrate for the application of an electric potential to the substrate.

Preferably, the nozzle, channel and recess are etched from the silicon substrate by reactive-ion etching and other standard semiconductor processing techniques. The nozzle side features, through-substrate fluid channel, reservoir side features, and controlling electrodes are preferably formed monolithically from a monocrystalline silicon substrate—i.e., they are formed during the course of and as a result of a fabrication sequence that requires no manipulation or assembly of separate components.

Because the electrospray device is manufactured using reactive-ion etching and other standard semiconductor processing techniques, the dimensions of such a device can be very small, for example, as small as 2 μm inner diameter and 5 μm outer diameter. Thus, a through-substrate fluid channel having, for example, 5 μm inner diameter and a substrate thickness of 250 μm only has a volume of 4.9 pL. The micrometer-scale dimensions of the electrospray device minimize the dead volume and thereby increase efficiency and analysis sensitivity when combined with a separation device.

The electrospray device of the present invention provides for the efficient and effective formation of an electrospray. By providing an electrospray surface from which the fluid is ejected with dimensions on the order of micrometers, the electrospray device limits the voltage required to generate a Taylor cone as the voltage is dependent upon the nozzle diameter, the surface tension of the fluid, and the distance of the nozzle from an extracting electrode. The nozzle of the electrospray device provides the physical asperity on the order of micrometers on which a large electric field is concentrated. Further, the electrospray device may provide additional electrode(s) on the ejecting surface to which electric potential(s) may be applied and controlled independent of the electric potentials of the fluid and the extracting electrode in order to advantageously modify and optimize the electric field in order to focus the gas phase ions resulting from electrospray of fluids. The combination of the nozzle and the additional electrode(s) thus enhance the electric field between the nozzle, the substrate and the extracting electrode. The electrodes are preferable positioned within about 500 microns, and more preferably within about 200 microns from the exit orifice.

The microchip-based electrospray device of the present invention provides minimal extra-column dispersion as a result of a reduction in the extra-column volume and provides efficient, reproducible, reliable and rugged formation of an electrospray. This electrospray device is perfectly suited for the electrospray of fluids from microchip-based separation devices. The design of this electrospray device is also robust such that the device can be readily mass-produced in a cost-effective, high-yielding process.

In operation, a conductive or partly conductive liquid sample is introduced into the through-substrate channel entrance orifice on the injection surface. The liquid is held at a potential voltage, either by means of a conductive fluid delivery device to the electrospray device or by means of an electrode formed on the injection surface isolated from the surrounding surface region and from the substrate. The electric field strength at the tip of the nozzle is enhanced by the application of a voltage to the substrate and/or the ejection surface, preferably zero volts up to approximately less than one-half of the voltage applied to the fluid. Thus, by the independent control of the fluid/nozzle and substrate/ejection surface voltages, the electrospray device of the present invention allows the optimization of the electric field emanating from the nozzle. The electrospray device of the present invention may be placed 1–2 mm or up to 10 mm from the orifice of an atmospheric pressure ionization ("API") mass spectrometer to establish a stable nanoelectrospray at flow rates in the range of a few nanoliters per minute.

The electrospray device may be interfaced or integrated downstream to a sampling device, depending on the particular application. For example, the analyte may be electrosprayed onto a surface to coat that surface or into another device for purposes of conveyance, analysis, and/or synthesis. As described above, highly charged droplets are formed at atmospheric pressure by the electrospray device from nanoliter-scale volumes of an analyte. The highly charged droplets produce gas-phase ions upon sufficient evaporation of solvent molecules which may be sampled, for example, through an ion-sampling orifice of an atmospheric pressure ionization mass spectrometer ("API-MS") for analysis of the electrosprayed fluid.

One embodiment of the present invention includes an array of multiple electrospray devices which allows for extensive parallel processing. The multiple electrospray devices or systems fabricated by an extensive amount of parallel processing on a single wafer may then be cut or otherwise separated into multiple devices or systems.

The polymer monolith/electrospray device may also serve to reproducibly distribute and deposit a sample from a mother plate to daughter plate(s) by nanoelectrospray deposition or by the droplet method. A chip-based combinatorial chemistry system including a reaction well block may define an array of reservoirs for containing the reaction products from a combinatorially synthesized compound. The reaction well block further defines channels, nozzles and recessed portions such that the fluid in each reservoir may flow through a corresponding channel and exit through a corresponding nozzle in the form of droplets. The reaction well block may define any number of reservoir(s) in any desirable configuration, each reservoir being of a suitable dimension and shape. The volume of a reservoir may range from a few picoliters up to several microliters.

The reaction well block may serve as a mother plate to interface to a microchip-based chemical synthesis apparatus such that the droplet method of the electrospray device may be utilized to reproducibly distribute discreet quantities of the product solutions to a receiving or daughter plate. The daughter plate defines receiving wells that correspond to each of the reservoirs. The distributed product solutions in the daughter plate may then be utilized to screen the combinatorial chemical library against biological targets.

The polymer monolith/electrospray device may also serve to reproducibly distribute and deposit an array of samples from a mother plate to daughter plates, for example, for proteomic screening of new drug candidates. This may be by either droplet formation or electrospray modes of operation. Electrospray device(s) may be etched into a microdevice capable of synthesizing combinatorial chemical libraries. At a desired time, a nozzle(s) may apportion a desired amount of a sample(s) or reagent(s) from a mother plate to a daughter plate(s). Control of the nozzle dimensions, applied voltages, and time provide a precise and reproducible method of sample apportionment or deposition from an array of nozzles, such as for the generation of sample plates for molecular weight determinations by matrix-assisted laser desorption/ionization time-of-flight mass spectrometry ("MALDI-TOFMS"). The capability of transferring analytes from a mother plate to daughter plates may also be utilized to make other daughter plates for other types of assays, such as proteomic screening. The fluid to substrate potential voltage ratio can be chosen for formation of an electrospray or droplet mode based on a particular application.

The electrospray device of the present invention can be integrated with miniaturized liquid sample handling devices for efficient electrospray of the liquid samples for detection using a mass spectrometer. The electrospray device may also be used to distribute and apportion fluid samples for use with high-throughput screen technology. The electrospray device may incorporate polymer monolith for producing a liquid separation stationary phase. The electrospray device may be chip-to-chip or wafer-to-wafer bonded to plastic, glass, or silicon microchip-based liquid separation devices capable of, for example, capillary electrophoresis, capillary electrochromatography, affinity chromatography, liquid chromatography ("LC"), or any other condensed-phase separation technique.

An array or matrix of multiple electrospray devices of the present invention may be manufactured on a single microchip as silicon fabrication using standard, well-controlled thin-film processes. This not only eliminates handling of such micro components but also allows for rapid parallel processing of functionally similar elements. The low cost of these electrospray devices allows for one-time use such that cross-contamination from different liquid samples may be eliminated.

A multi-system chip thus provides a rapid sequential chemical analysis system fabricated using Micro-ElectroMechanical System ("MEMS") technology. For example, the multi-system chip enables automated, sequential separation and injection of a multiplicity of samples, resulting in significantly greater analysis throughput and utilization of the mass spectrometer instrument for, for example, high-throughput detection of compounds for drug discovery.

Another aspect of the present invention provides a silicon microchip-based electrospray device for producing electrospray of a liquid sample. The electrospray device may be interfaced downstream to an atmospheric pressure ionization mass spectrometer ("API-MS") for analysis of the electrosprayed fluid. Another aspect of the invention is an integrated miniaturized liquid phase separation device, which may have, for example, glass, plastic or silicon substrates integral with the electrospray device.

Electrospray Device Fabrication Procedure

The polymer monolith/multiple-electrospray device 250 is preferably fabricated as a monolithic silicon substrate utilizing well-established, controlled thin-film silicon processing techniques such as thermal oxidation, photolithography, reactive-ion etching (RIE), chemical vapor deposition, ion implantation, and metal deposition. Fabrication using such silicon processing techniques facilitates massively parallel processing of similar devices, is time- and cost-efficient, allows for tighter control of critical dimensions, is easily reproducible, and results in a wholly integral device, thereby eliminating any assembly requirements. Further, the fabrication sequence may be easily extended to create physical aspects or features on the injection surface and/or ejection surface of the electrospray device to facilitate interfacing and connection to a fluid delivery system or to facilitate integration with a fluid delivery sub-system to create a single integrated system.

Ejection or Nozzle Surface Processing

Figure 13A:
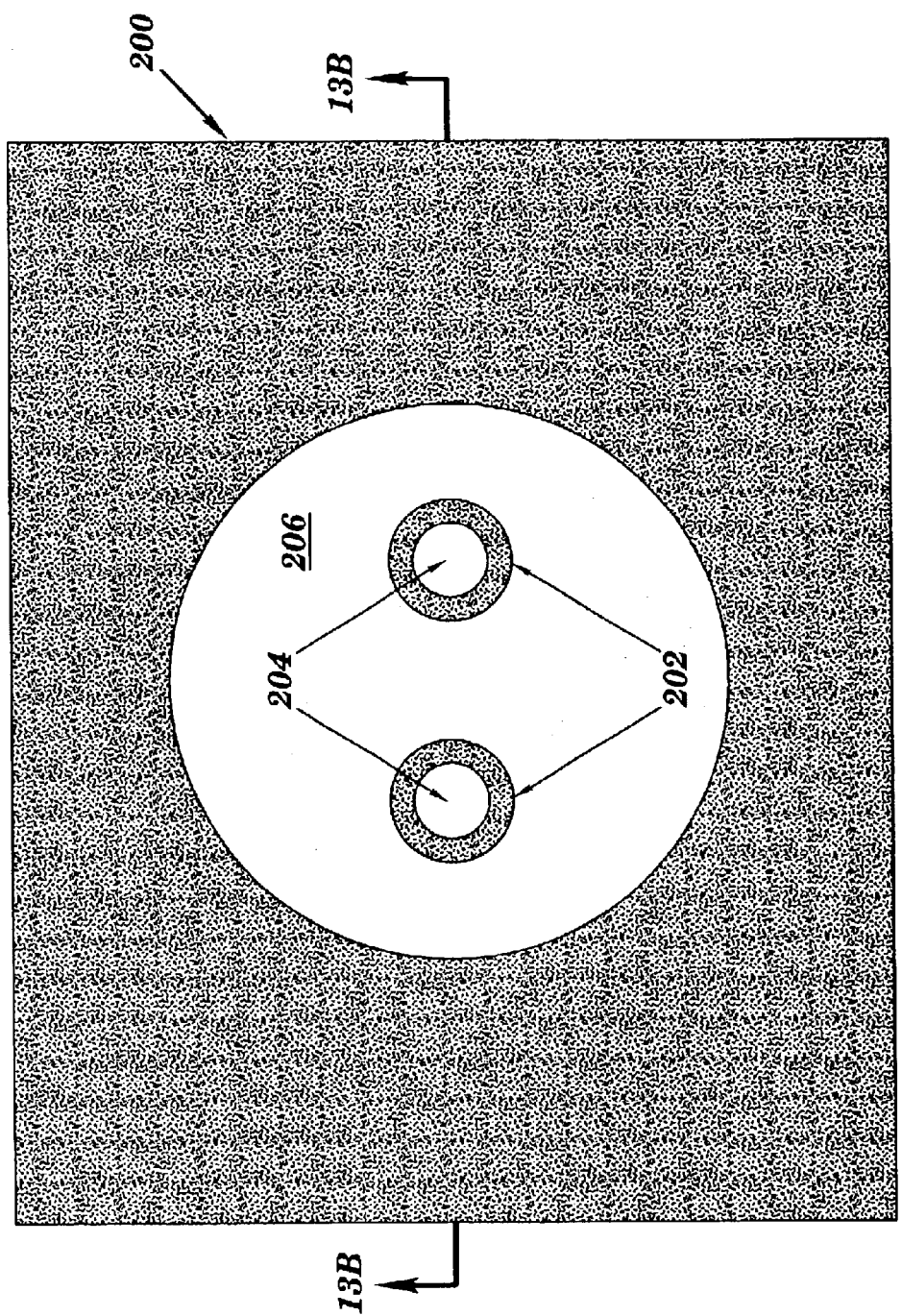
FIG. 13A is a plan view of mask one of a two-nozzle electrospray device.
Figure 13B:
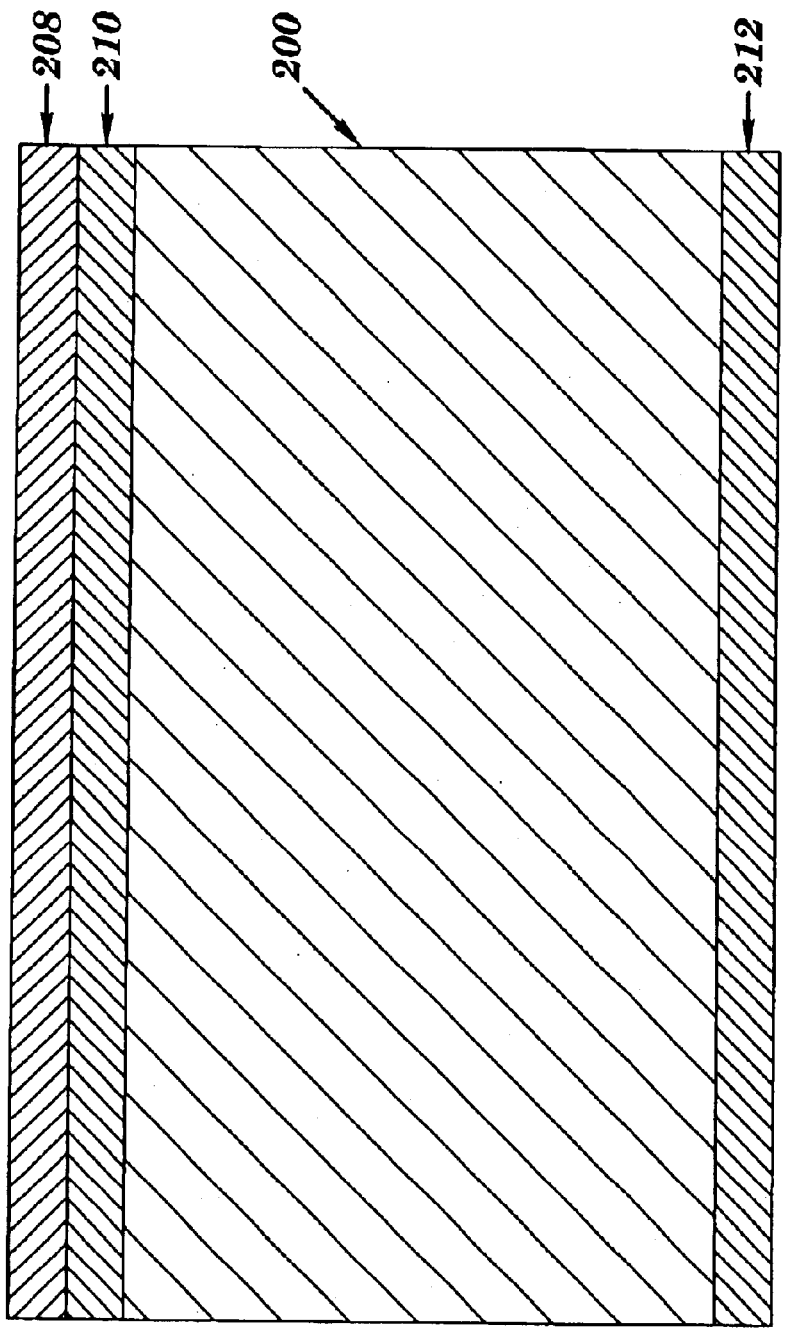
FIG. 13B is a cross-sectional view of silicon substrate 200 showing photoresist layer 208 and silicon dioxide layers 210 and 212.

FIGS. 13A–13E illustrate the processing steps for the ejection or nozzle side of the substrate in fabricating the electrospray device of the present invention. Referring to the plan view of FIG. 13A, a mask is used to pattern 202 that will form the nozzle shape in the completed electrospray device 250. The patterns in the form of circles 204 forms through-substrate channels and 206 forms a recessed annular space around nozzles of a completed electrospray device. FIG. 13B is the cross-sectional view taken along line 13B—13B of FIG. 13A. A double-side polished silicon wafer 200 is subjected to an elevated temperature in an oxidizing environment to grow a layer or film of silicon dioxide 210 on the nozzle side and a layer or film of silicon dioxide 212 on the reservoir side of the substrate 200. Each of the resulting silicon dioxide layers 210, 212 has a thickness of approximately 1–3 $\mu$m. The silicon dioxide layers 210, 212 serve as masks for subsequent selective etching of certain areas of the silicon substrate 200.

Figure 13C:
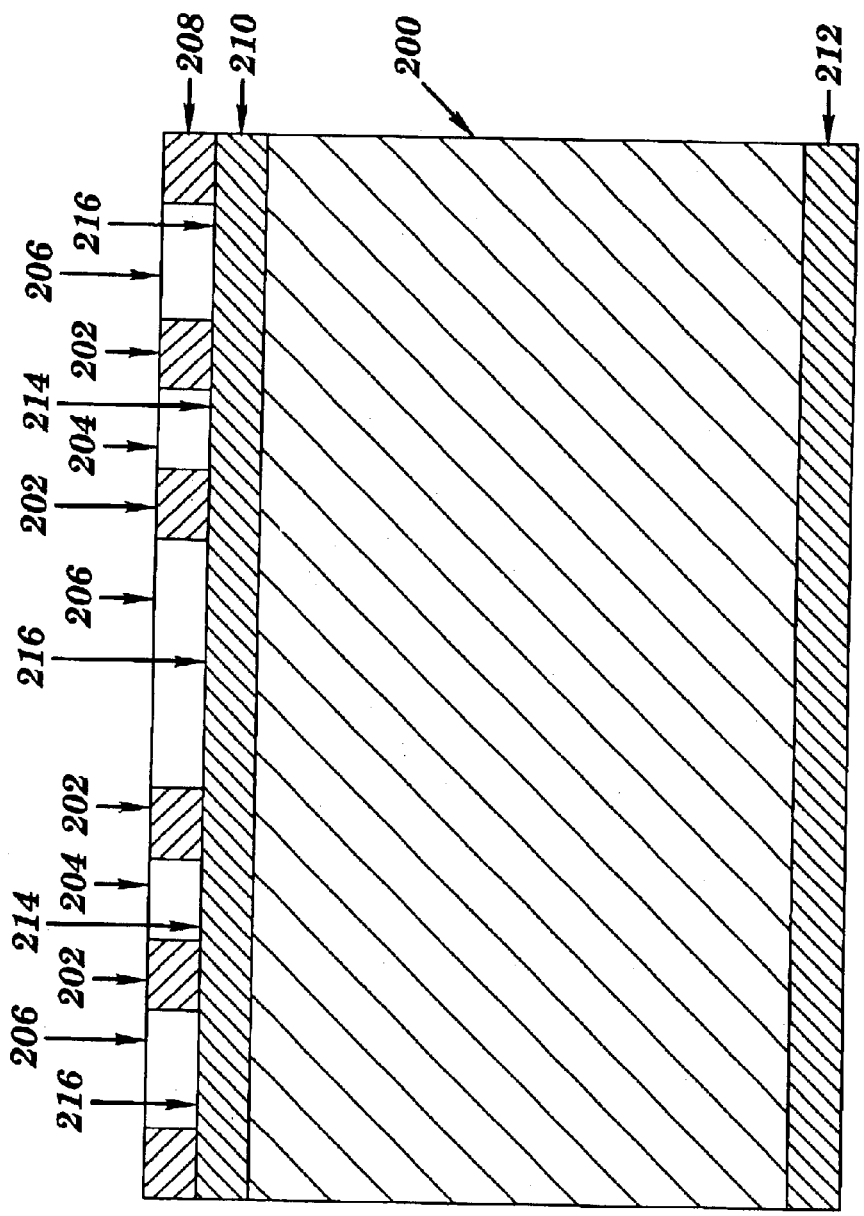
FIG. 13C is a cross-sectional view of a silicon substrate 200 showing removal of photoresist layer 208 to form a pattern of 204 and 206 in the photoresist.

A film of positive-working photoresist 208 is deposited on the silicon dioxide layer 210 on the nozzle side of the substrate 200. Referring to FIG. 13C, an area of the photoresist 204 corresponding to the entrance to through-wafer channels and an area of photoresist corresponding to the recessed annular region 206 which will be subsequently etched is selectively exposed through a mask (FIG. 13A) by an optical lithographic exposure tool passing short-wavelength light, such as blue or near-ultraviolet at wavelengths of 365, 405, or 436 nanometers.

Figure 13D:
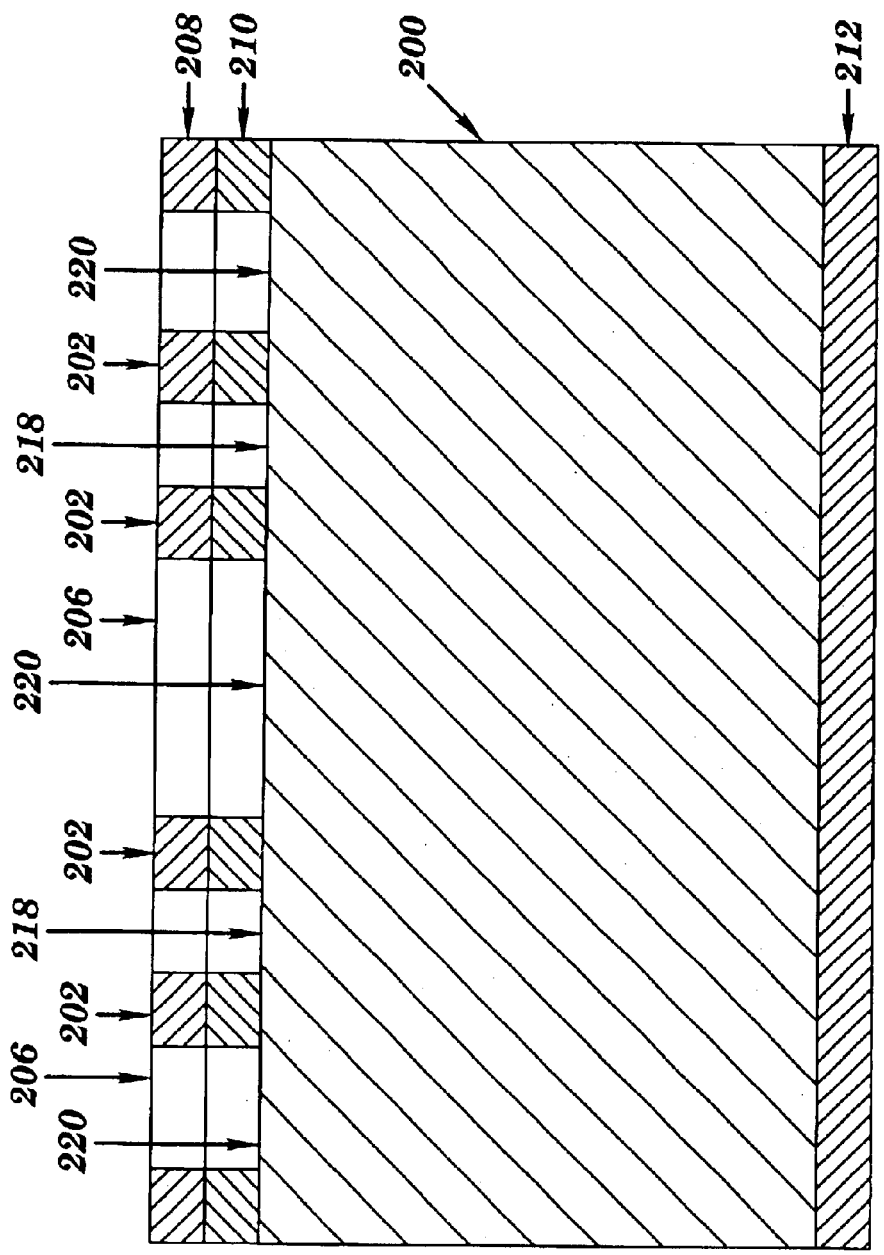
FIG. 13D is a cross-sectional view of a silicon substrate 200 showing removal of silicon dioxide 210 from the regions 214 and 216 to expose the silicon substrate 218 and 220 in these regions to form a pattern of 204 and 206 in the silicon dioxide 210.
Figure 13E:
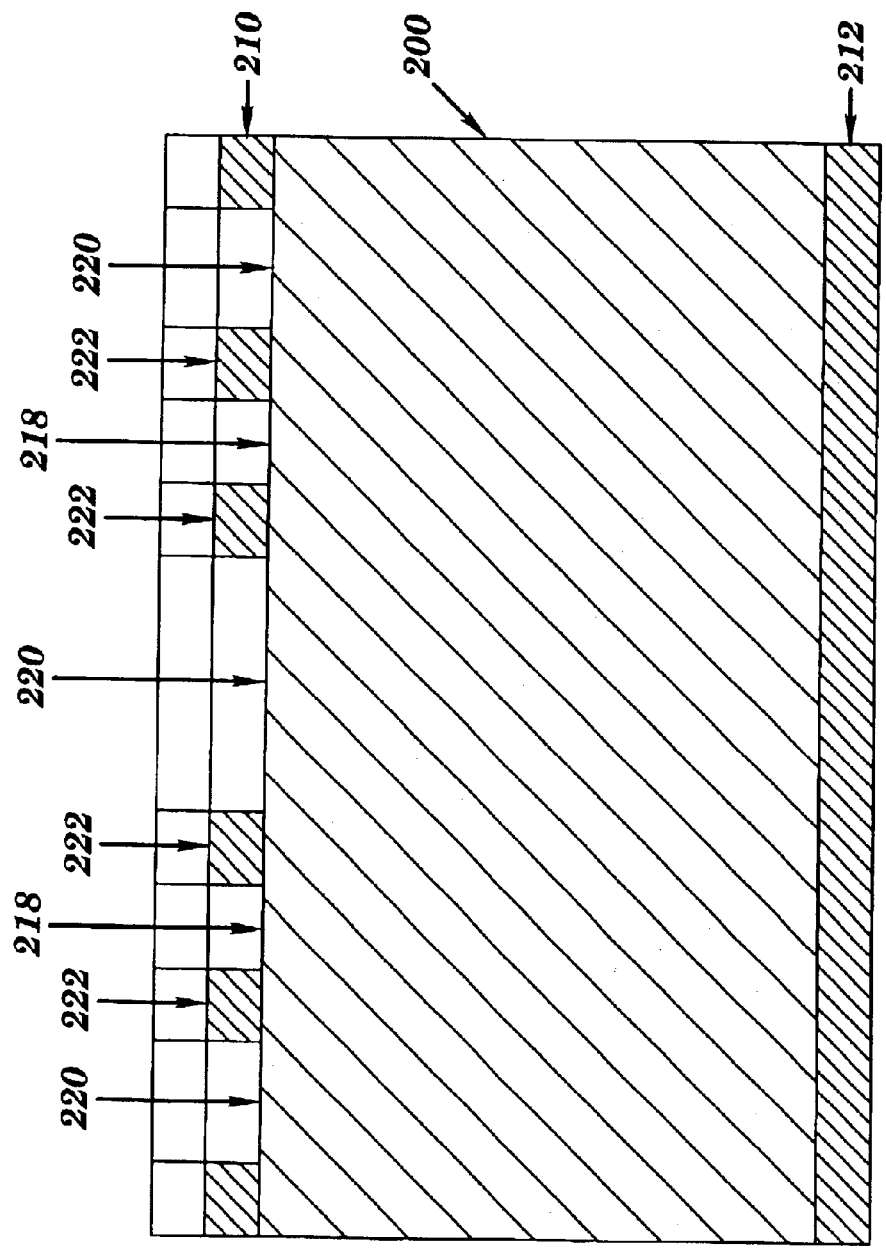
FIG. 13E is a cross-sectional view of a silicon substrate 200 showing removal of photoresist 208.

As shown in the cross-sectional view of FIG. 13C, after development of the photoresist 208, the exposed area 204 of the photoresist is removed and open to the underlying silicon dioxide layer 214 and the exposed area 206 of the photoresist is removed and open to the underlying silicon dioxide layer 216, while the unexposed areas remain protected by photoresist 208. Referring to FIG. 13D, the exposed areas 214, 216 of the silicon dioxide layer 210 is then etched by a fluorine-based plasma with a high degree of anisotropy and selectivity to the protective photoresist 208 until the silicon substrate 218, 220 are reached. As shown in the cross-sectional view of FIG. 13E, the remaining photoresist 208 is removed from the silicon substrate 200.

Injection or Reservoir Surface Processing

Figure 14A:
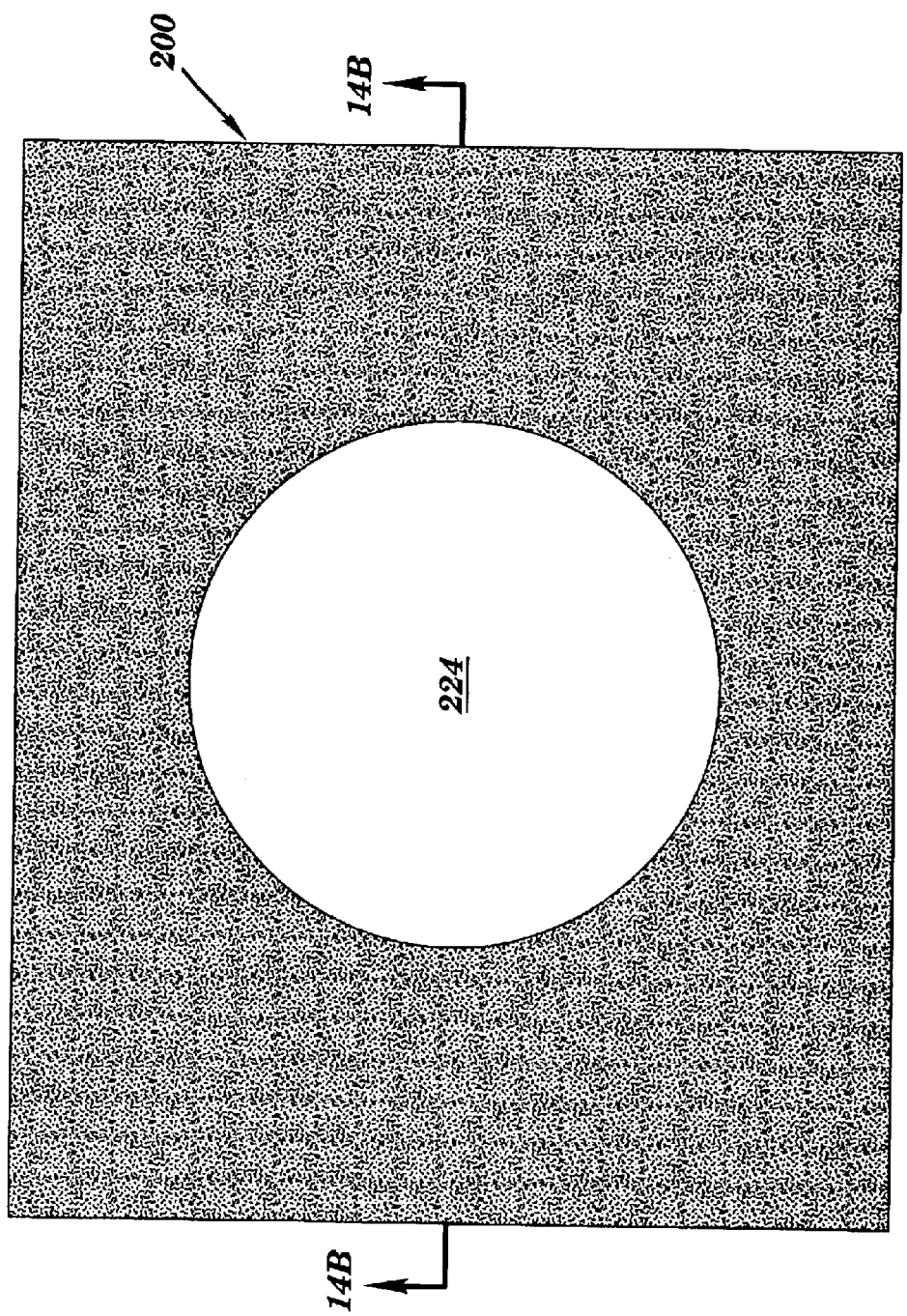
FIG. 14A is a plan view of mask two of a two-nozzle electrospray device.
Figure 14B:
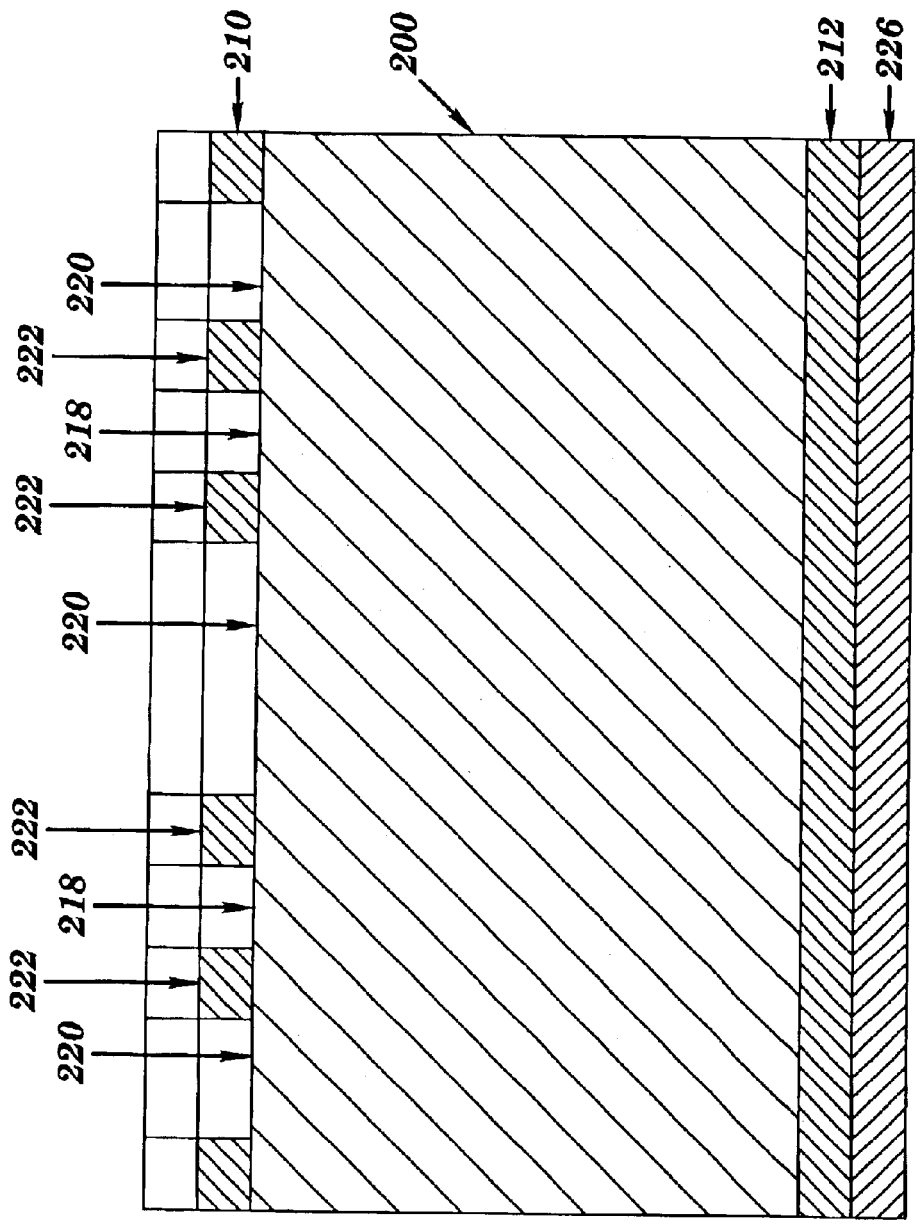
FIG. 14B is a cross-sectional view of silicon substrate 200 of FIG. 13E with a new layer of photoresist 226 on silicon dioxide layer 212.

Referring to the plan view of FIG. 14A, a mask is used to pattern 224 in the form of a circle on the injection surface. FIG. 14B is the cross-sectional view taken along line 14B—14B of FIG. 14A. A film of positive-working photoresist 226 is deposited on the silicon dioxide layer 212 on the reservoir side of the substrate 200. Referring to FIG. 14C, an area of the photoresist 224 corresponding to the reservoir placement is selectively exposed through a mask (FIG. 14A) by an optical lithographic exposure tool passing short-wavelength light, such as blue or near-ultraviolet at wavelengths of 365, 405, or 436 nanometers.

Figure 14D:
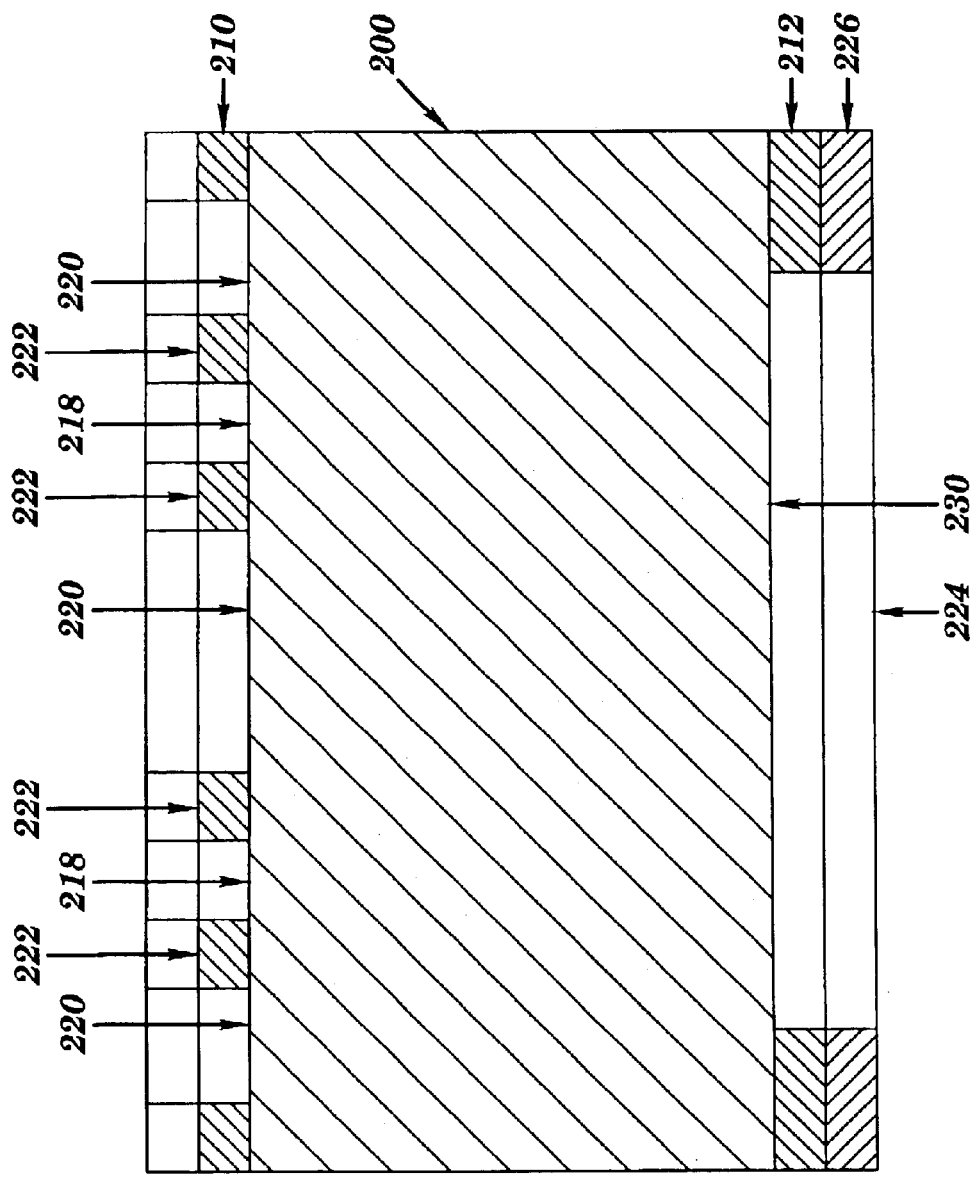
FIG. 14D is a cross-sectional view of a silicon substrate 200 showing the removal of silicon dioxide 228 from the region 224 to expose the silicon substrate 230.
Figure 14E:
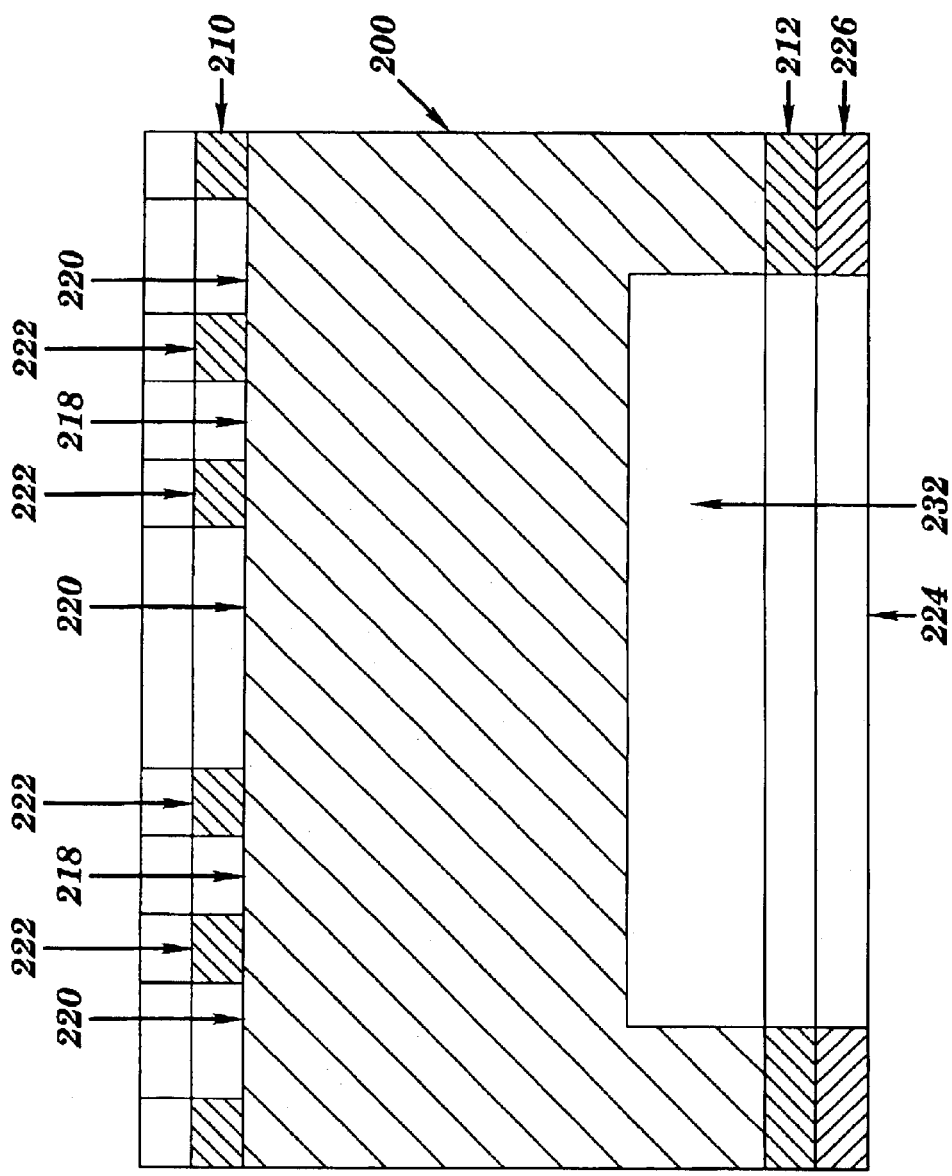
FIG. 14E is a cross-sectional view of a silicon substrate 200 showing removal of silicon 230 from region 224 to form reservoir 232 in the pattern of 224.

As shown in the cross-sectional view of FIG. 14C, after development of the photoresist 226, the exposed area 224 of the photoresist is removed to the underlying silicon substrate 228. The remaining photoresist 226 is used as a mask during the selective removal of silicon dioxide 228. The silicon dioxide 228 is then etched by a fluorine-based plasma with a high degree of anisotropy and selectivity to the protective photoresist 226 until the silicon substrate 230 is reached as shown in FIG. 14D. As shown in FIG. 14E, a DRIE silicon etch creates a cylindrical region in the silicon substrate 200 that defines a reservoir 232. The reservoir 232 is etched to the desired depth. The remaining photoresist 226 can then be removed.

Completion of the Ejection or Nozzle Surface Processing

Figure 15A:
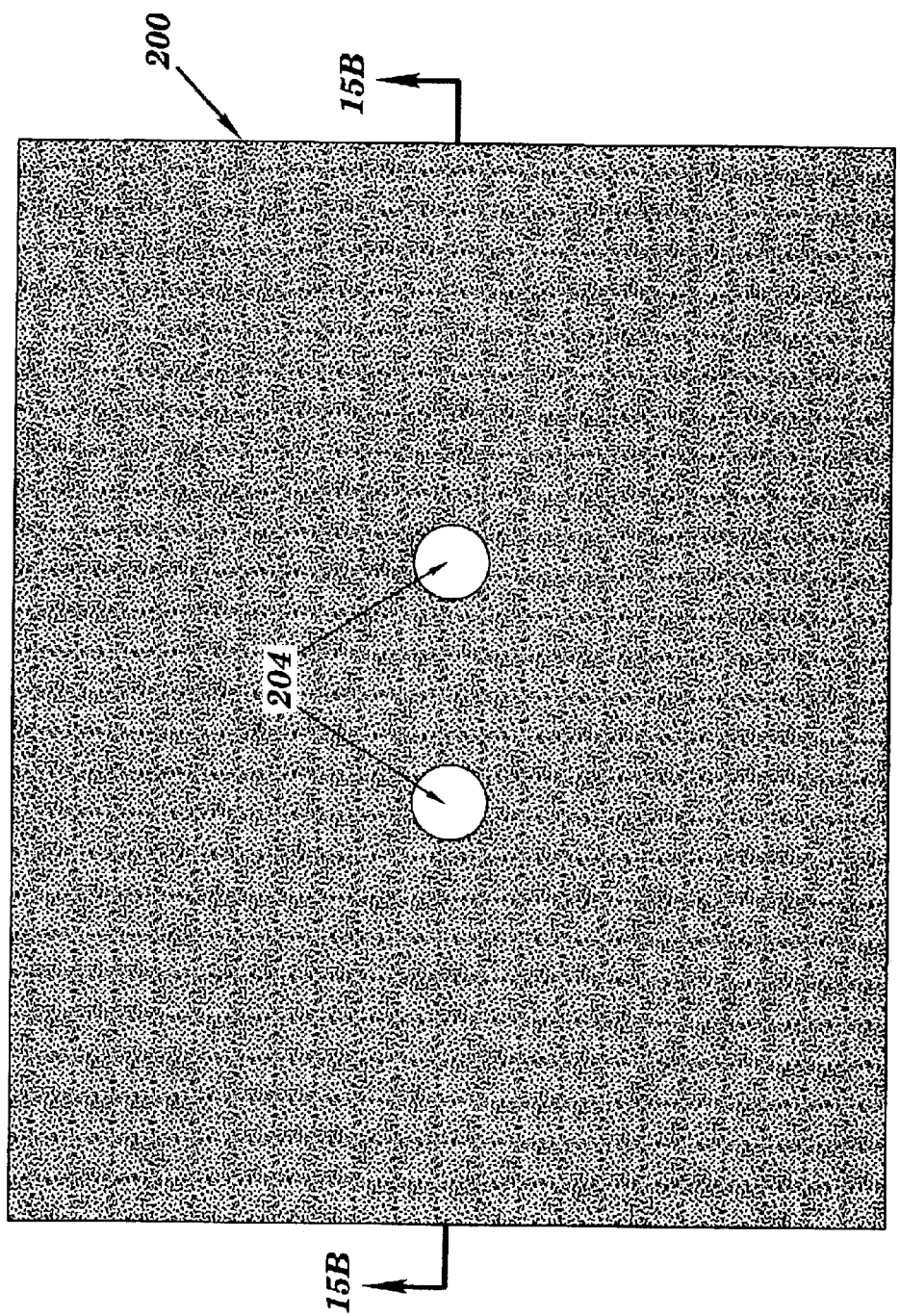
FIG. 15A is a plan view of mask three of a two-nozzle electrospray device.
Figure 15B:
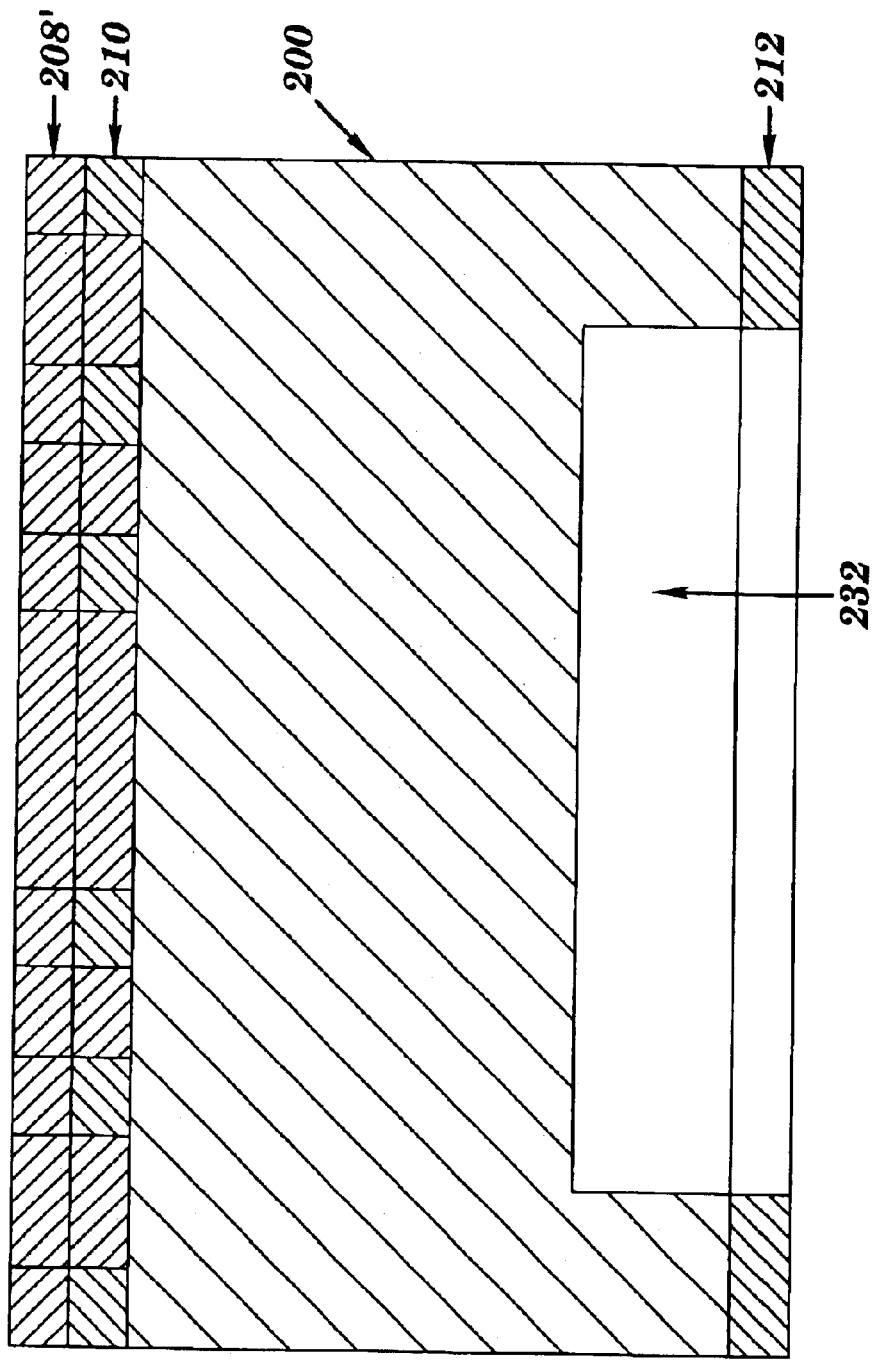
FIG. 15B is a cross-sectional view of a silicon substrate 200 showing a new layer of photoresist 208' on silicon dioxide layer 210.
Figure 15C:
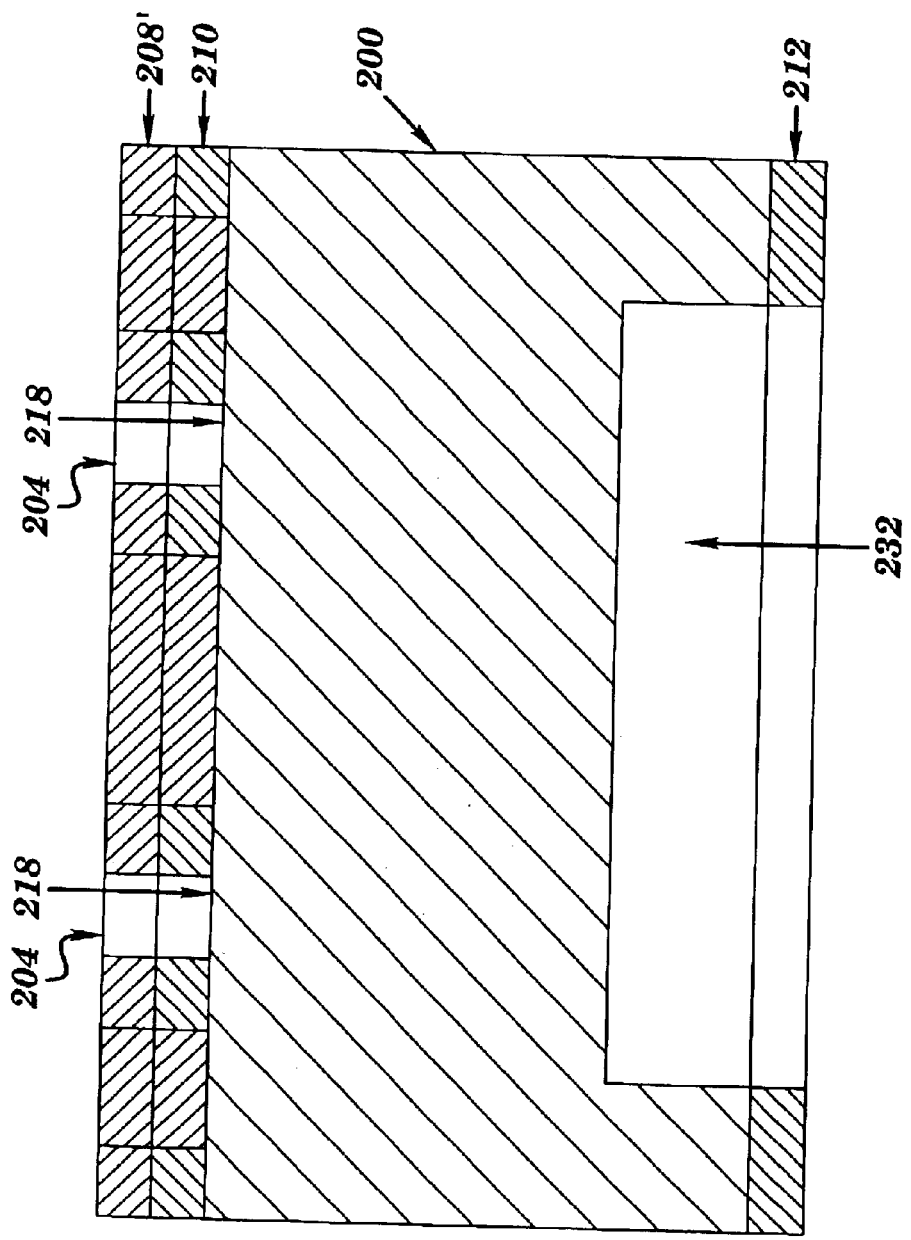
FIG. 15C is a cross-sectional view of a silicon substrate 200 showing removal of photoresist layer 208 to form pattern 204 in the photoresist exposing the underlying silicon substrate 218 in the pattern of 204.

FIGS. 15A–15J illustrate the processing steps for the ejection or nozzle side of the substrate in fabricating the electrospray device of the present invention. Referring to the plan view of FIG. 15A, a mask is used to pattern 204 to define the through-substrate channels of the device. FIG. 15B is the cross-sectional view taken along line 15B—15B of FIG. 15A. A film of positive-working photoresist 208' is deposited on the silicon dioxide layer 210 on the nozzle side of the substrate 200. Referring to FIG. 15C, an area of the photoresist 204 corresponding to the entrance to through-substrate channels which will be subsequently etched is silectively exposed through a mask (FIG. 15A) by an optical lithographic exposure tool passing short-wavelength light, such as blue or near-ultraviolet at wavelengths of 365, 405, or 436 nanometers.

Figure 15D:
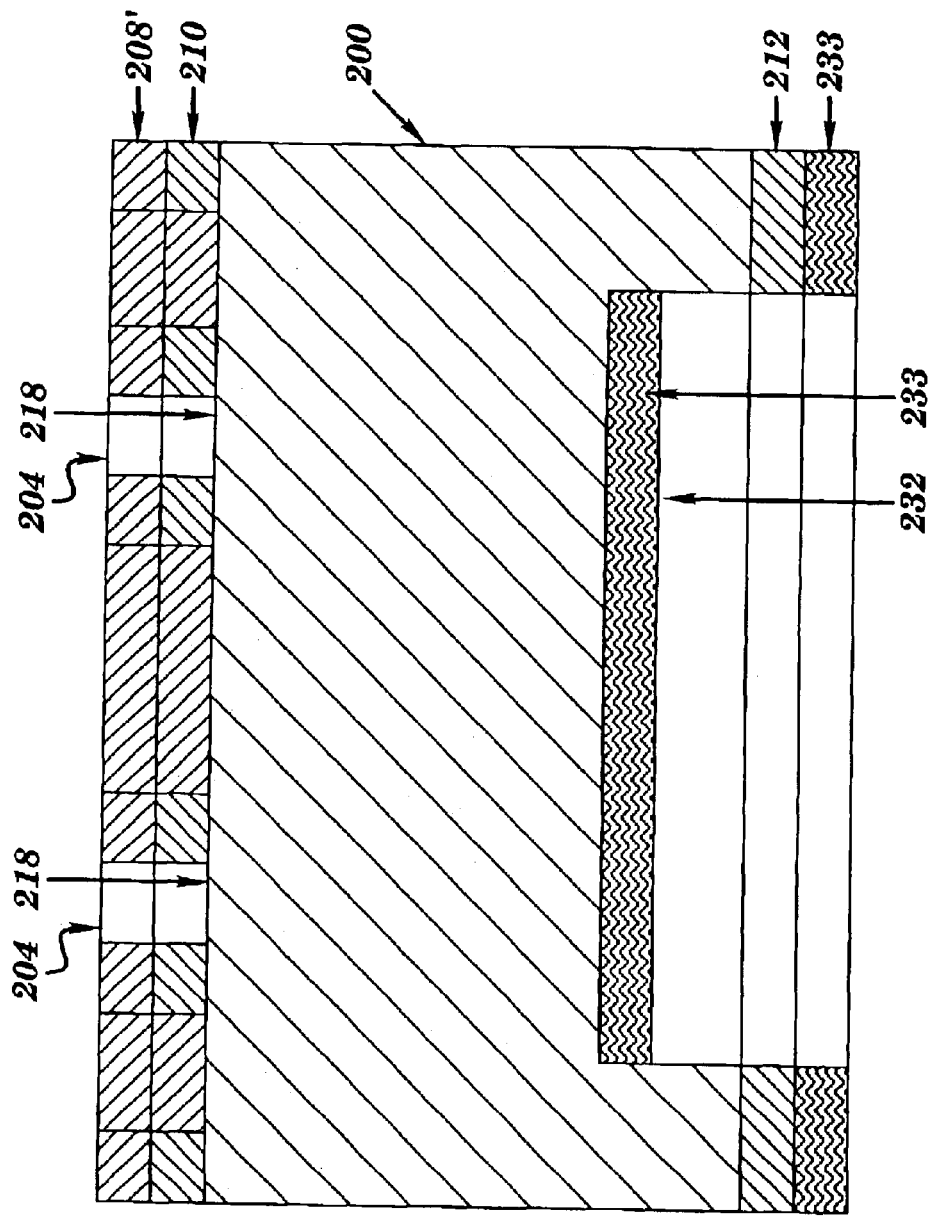
FIG. 15D is a cross-sectional view of a silicon substrate 200 showing removal of silicon material 234 corresponding to the pattern 204 until the reservoir 232 is reached.

As shown in the cross-sectional view of FIG. 15C, after development of the photoresist 208', the exposed area 204 of the photoresist is removed and open to the underlying silicon layer 218 while the unexposed areas remain protected by photoresist 208'. Referring to FIG. 15D, a plasma enhanced chemical vapor deposition ("PECVD") silicon dioxide layer 233 is deposited on the reservoir side of the substrate 200 to serve as an etch stop for the subsequent etch of the through-substrate channel 234 shown in FIG. 15E.

This technique has several advantages over other techniques, primarily due to the function of the etch stop deposited on the reservoir side of the substrate. This feature improves the production of a through-wafer channel having a consistent diameter throughout its length. An artifact of the etching process is the difficulty of maintaining consistent channel diameter when approaching an exposed surface of the substrate from within. Typically, the etching process forms a channel having a slightly smaller diameter at the end of the channel as it breaks through the opening. This is improved by the ability to slightly over-etch the channel when contacting the etch stop. Further, another advantage of etching the reservoir and depositing an etch stop prior to the channel etch is that micro-protrusions resulting from the side passivation of the channels remaining at the channel opening are avoided. The etch stop also functions to isolate the plasma region from the cooling gas when providing through holes and avoiding possible contamination from etching by products.

Figure 15E:
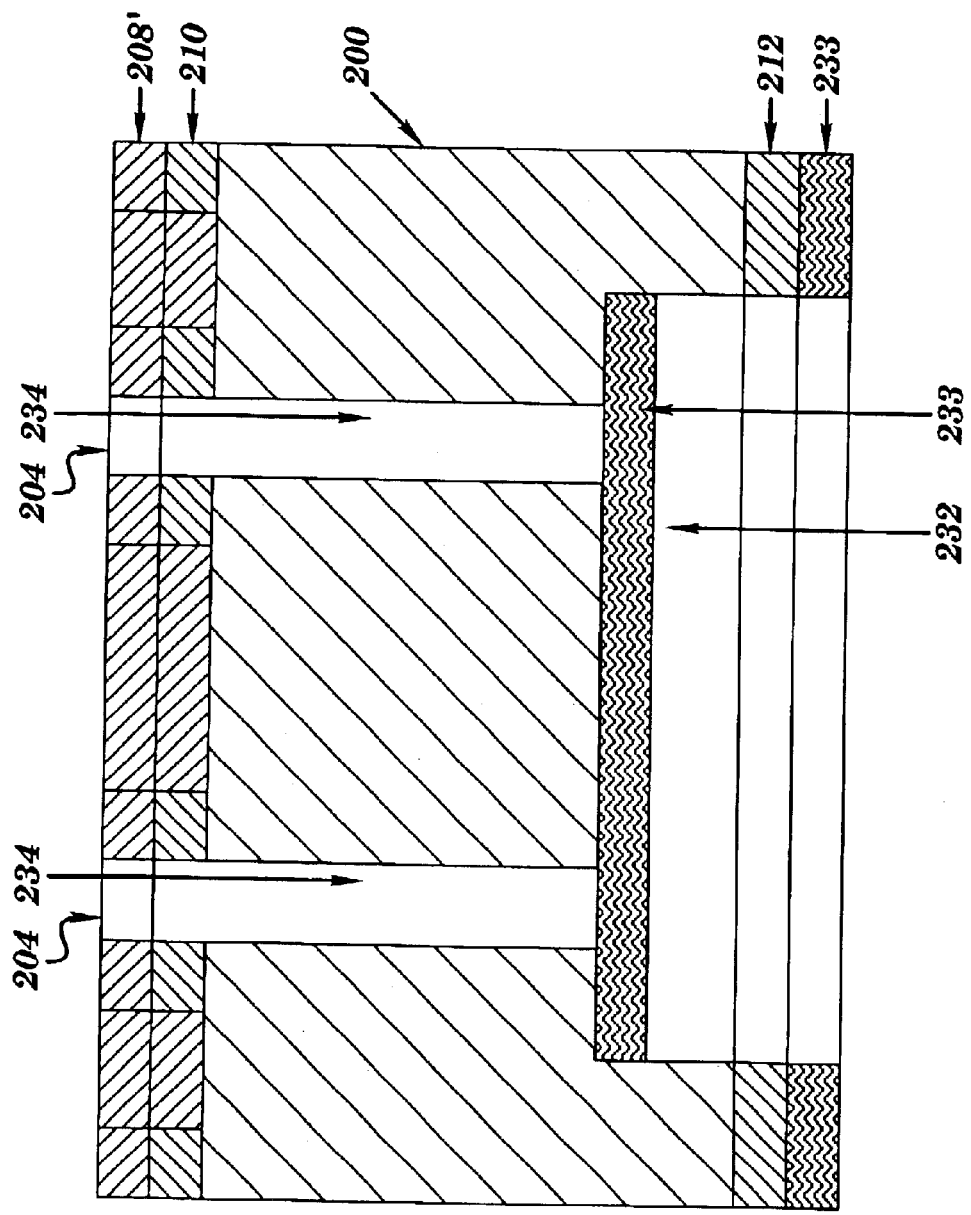
FIG. 15E is a cross-sectional view of a silicon substrate 200 showing removal of photoresist 208' and 226.
Figure 15F:
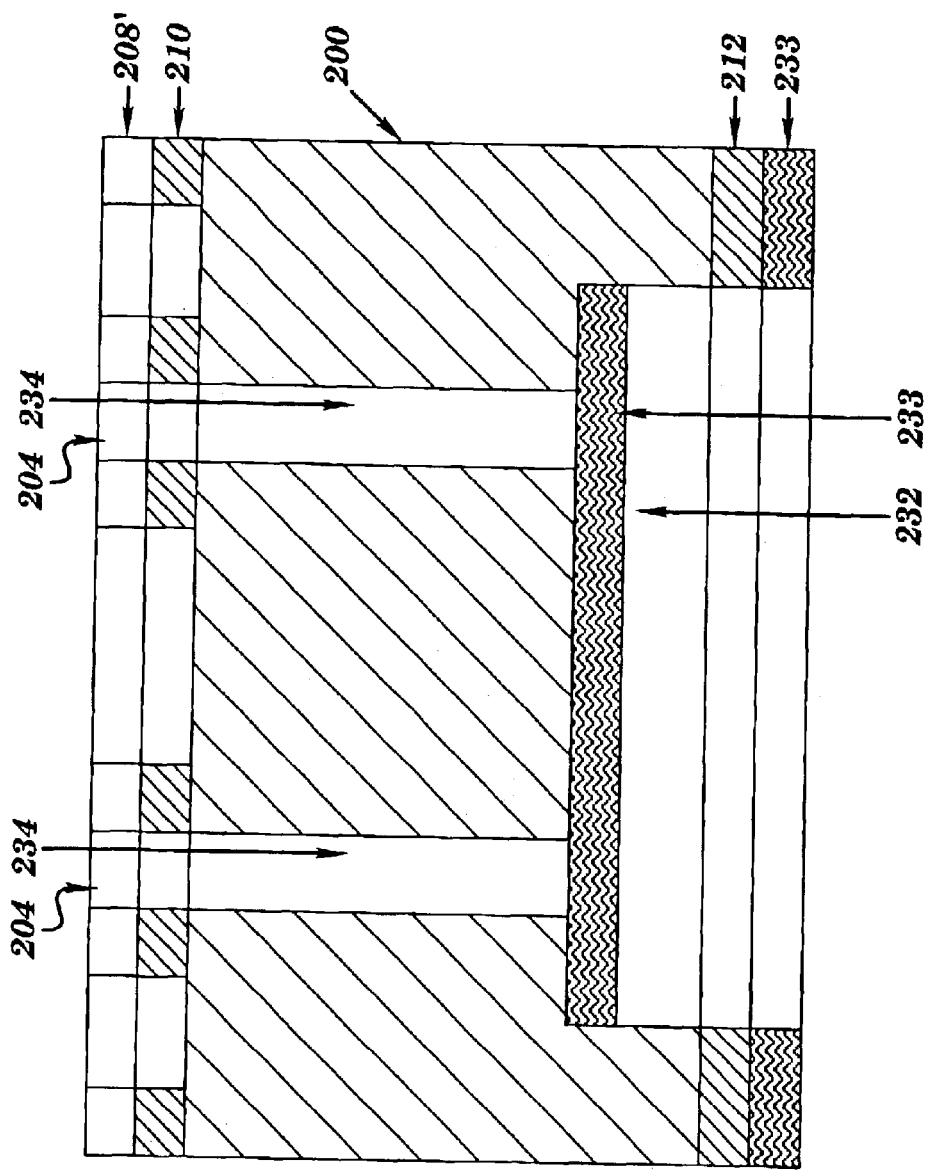
FIG. 15F is a cross-sectional view of a silicon substrate 200 showing thermal oxidation of the exposed silicon substrate 200 to form a layer of silicon dioxide 236 and 238 on exposed silicon horizontal and vertical surfaces, respectively.

Referring to FIG. 15E, the exposed areas 218 of the silicon substrate are then etched by a DRIE plasma with a high degree of anisotropy and selectivity to the protective photoresist 208' to define through-substrate channels 234 until the reservoir 232 is reached. As shown in the cross-sectional view of FIG. 15F, the remaining photoresist 208' and 226 is removed from the silicon substrate 200.

Figure 15G:
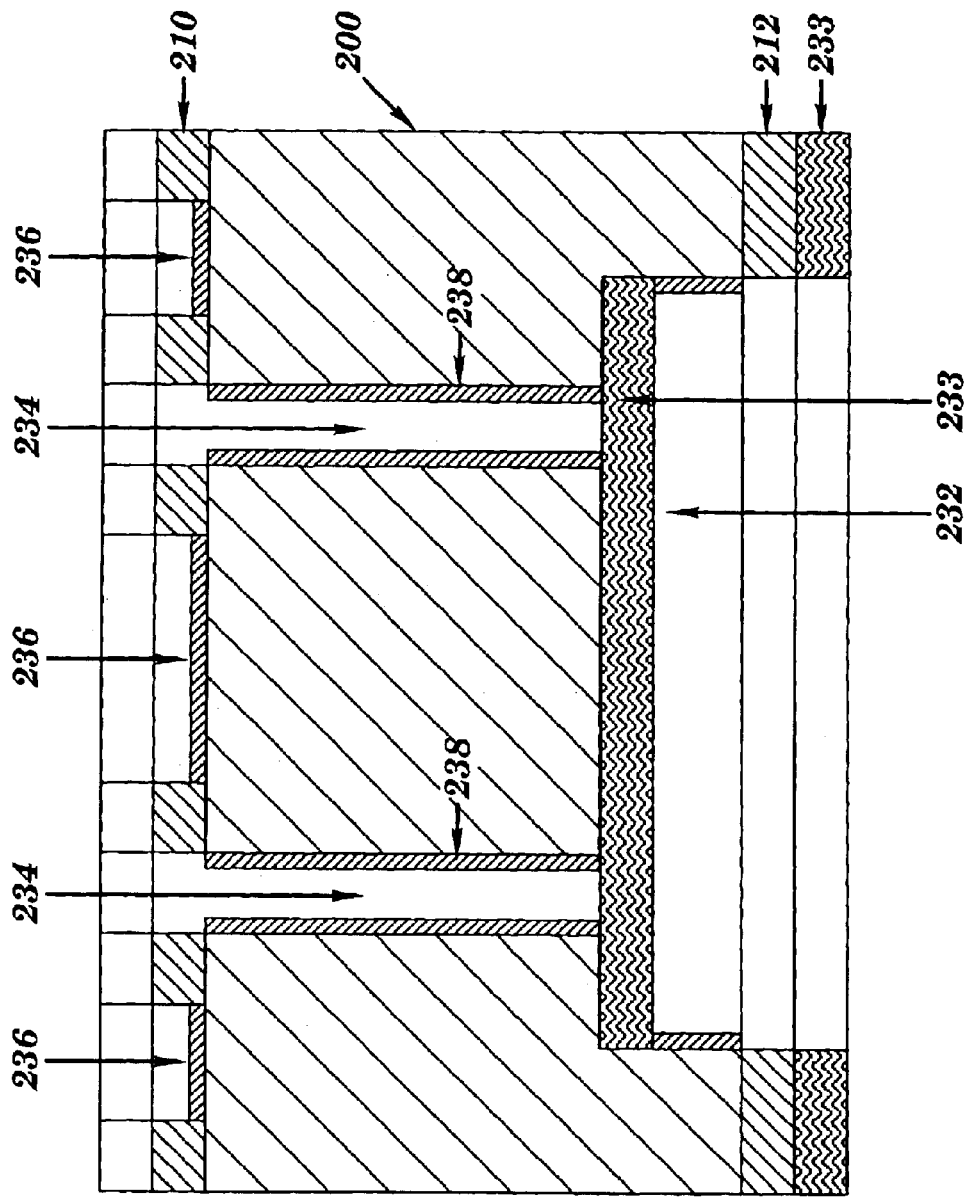
FIG. 15G is a cross-sectional view of a silicon substrate 200 showing selective removal of silicon dioxide 236 on the ejection side of the silicon substrate exposing the underlying silicon substrate 220.
Figure 15H:
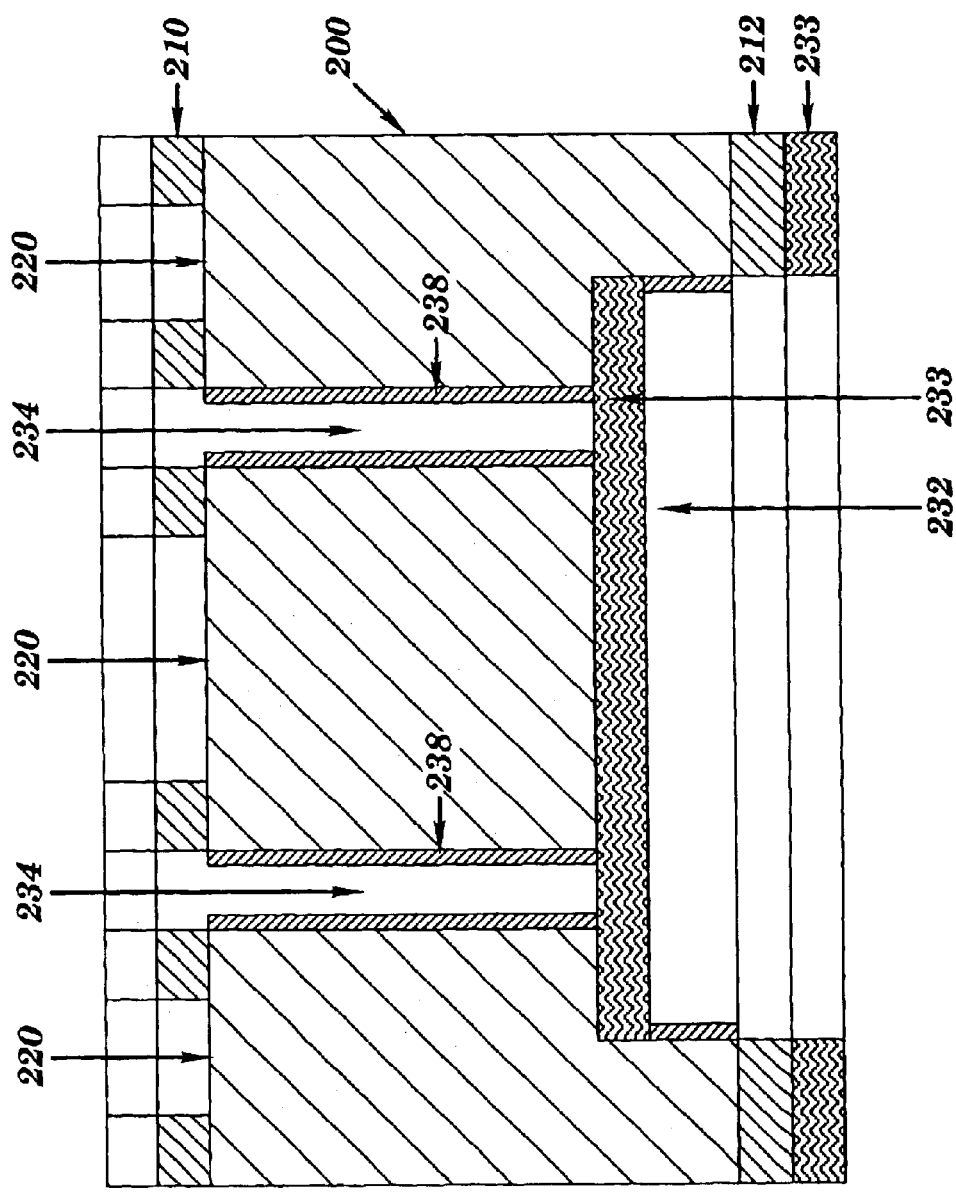
FIG. 15H is a cross-sectional view of a silicon substrate 200 showing removal of silicon substrate 220 to form an annular space 240 around the nozzles 242.
Figure 15I:
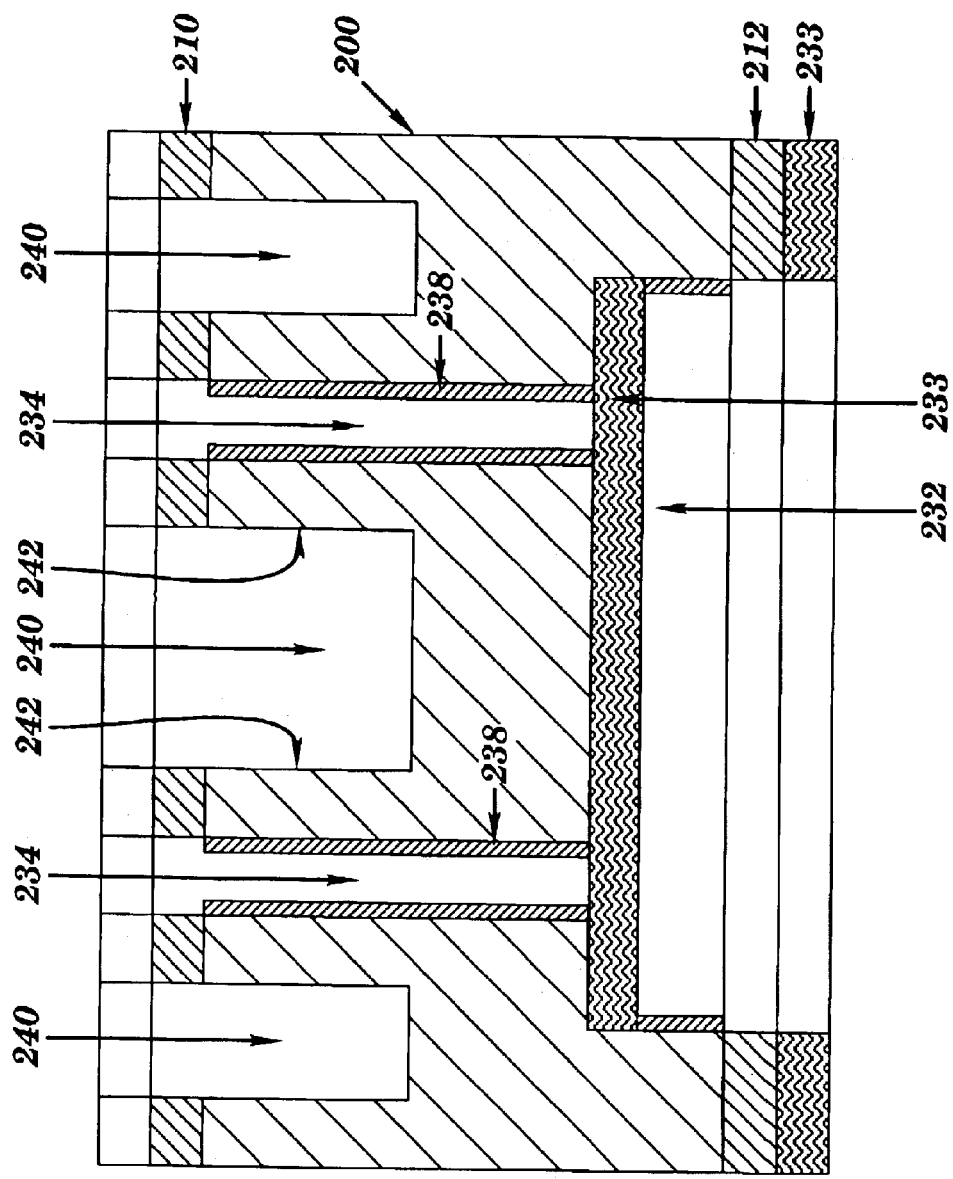
FIG. 15I is a cross-sectional view of the DRIE etch of silicon 220 to form the recessed annular region 240 and the nozzles 242.
Figure 15J:
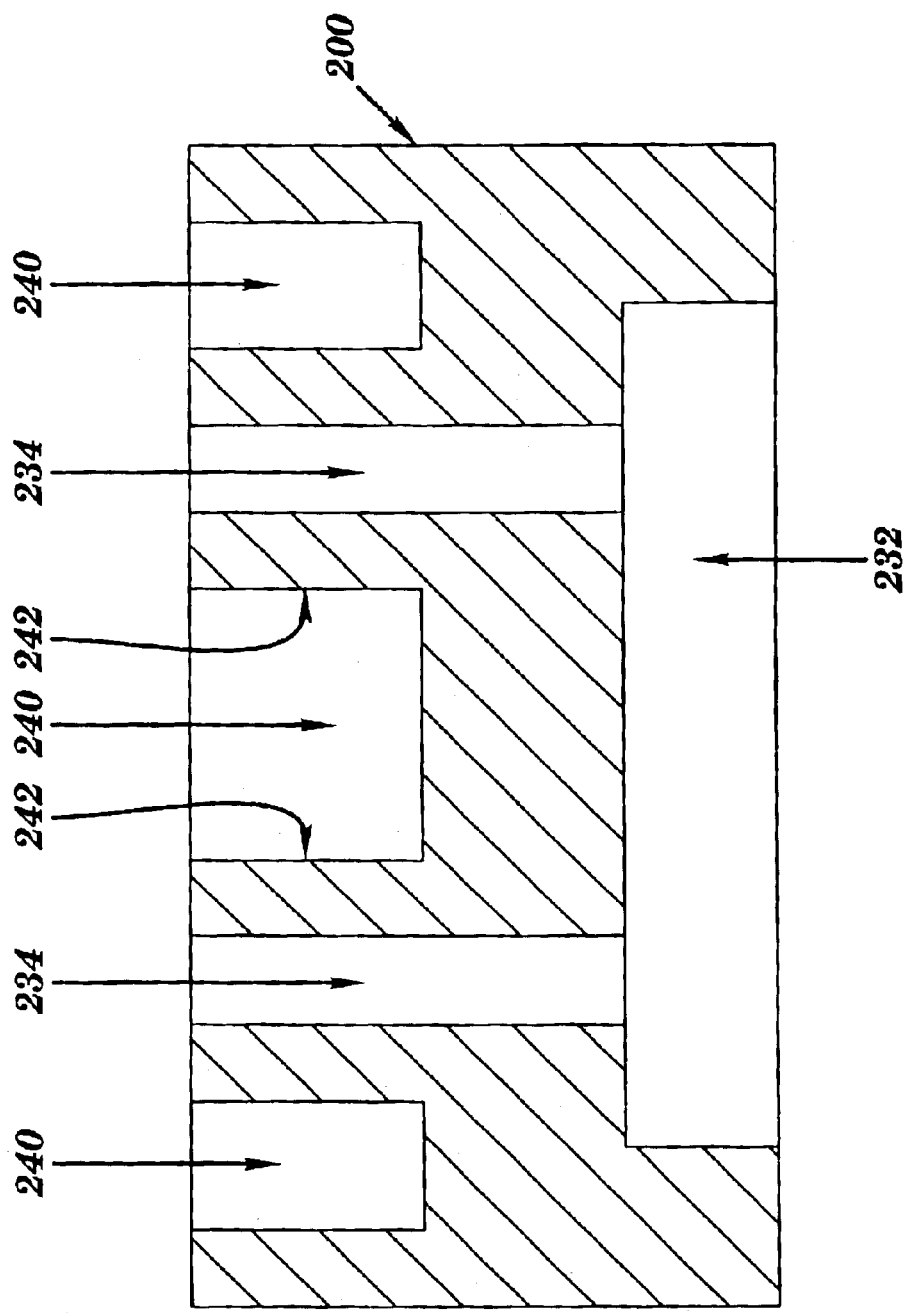
FIG. 15J is a cross-sectional view of a silicon substrate 200 showing removal of silicon dioxide layers 210, 212, 233 and 238.

Referring to FIG. 15G, the substrate 200 is subjected to an elevated temperature in an oxidizing environment to grow a layer or film of silicon dioxide 236 on the ejection or nozzle side of the substrate 200 and a layer or film of silicon dioxide 238 on all other exposed surfaces of the silicon substrate 200. Each of the resulting silicon dioxide layers 236, 238 has a thickness of approximately up to 2 $\mu$m. As shown in FIG. 15H, the silicon dioxide layer 236 is then etched by a fluorine-based plasma until the silicon substrate 220 is reached. The silicon dioxide 238 on the surface of the through-substrate channels 234 serves as an etch stop for the subsequent DRIE etch of the silicon 220 of the silicon substrate 200. This allows for formation of longer nozzles (i.e., a deeper DRIE etch) with wall thicknesses less than 2 $\mu$m over prior disclosed fabrication methods without accidental etching of the very thin silicon material that defines the nozzle wall thickness. FIG. 15I shows the DRIE etch of silicon 220 to form the recessed annular region 240 and the nozzles 242. FIG. 15J shows the removal of silicon dioxide layers 210, 212, 233 and 238 from the silicon substrate 200. The silicon dioxide layer 233 etch stop can be removed from the substrate by a hydrofluoric acid process.

An advantage of the fabrication process described herein is that the process simplifies the alignment of the through-substrate channels and the recessed annular region. This allows the fabrication of smaller nozzles with greater ease without any complex alignment of masks. Dimensions of the through channel, such as the aspect ratio (i.e. depth to width), can be reliably and reproducibly limited and controlled.

Preparation of the Substrate for Electrical Isolation

Figure 16A:
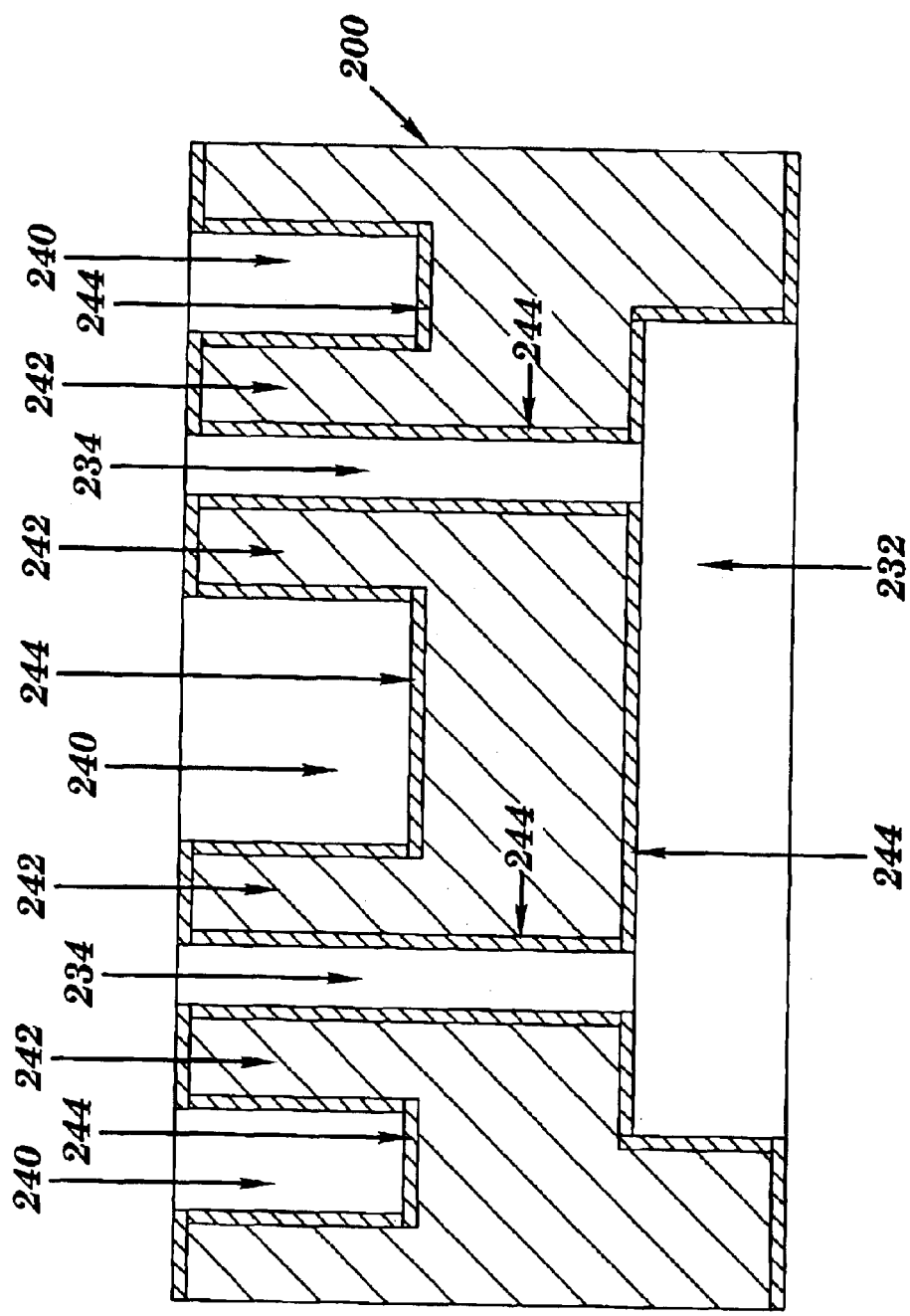
FIG. 16A is a cross-sectional view of a silicon substrate 200 showing thermal oxidation of the exposed silicon substrate 200 to form a layer of silicon dioxide 244 on all exposed silicon surfaces.
Figure 16B:
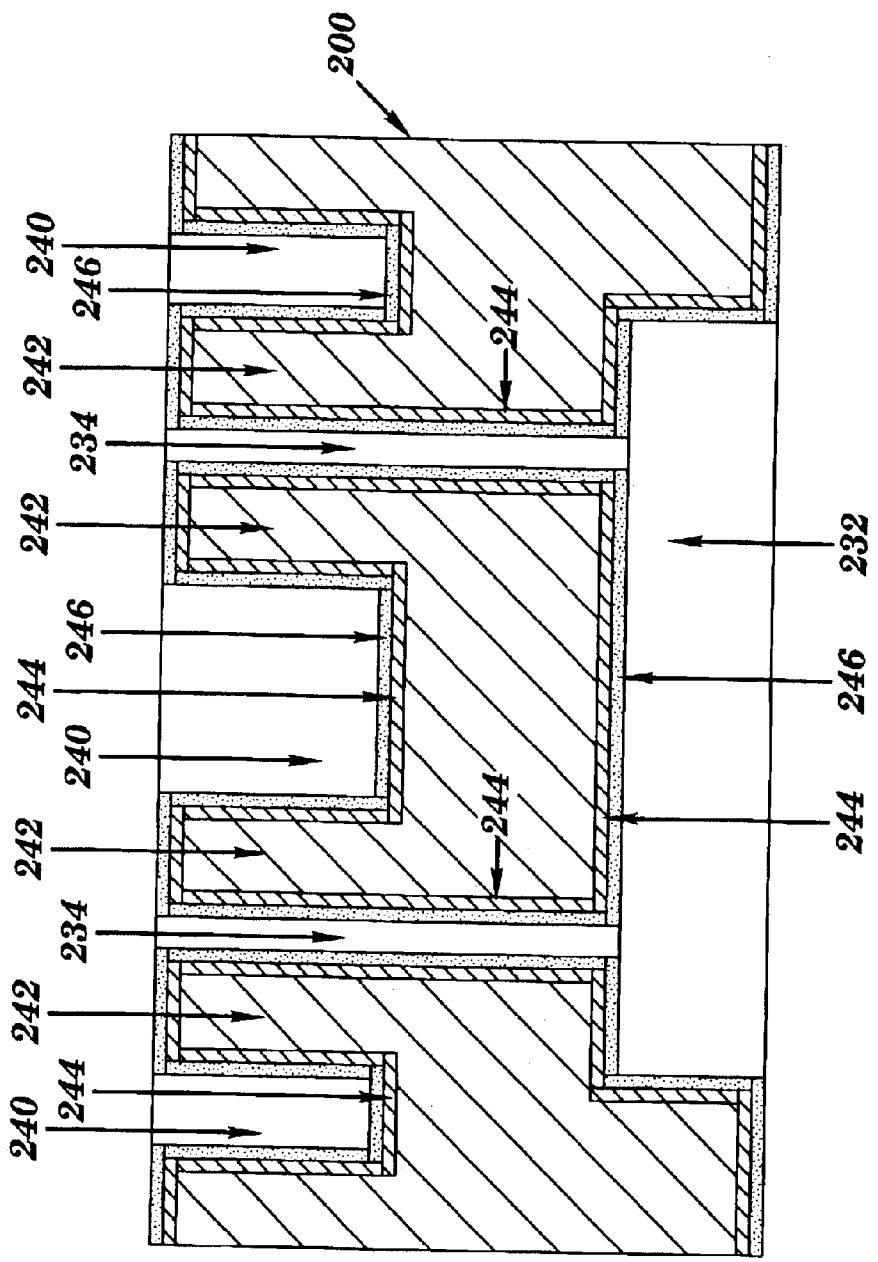
FIG. 16B is a cross-sectional view of a silicon substrate 200 showing low pressure vapor deposition of silicon nitride 246 conformally coating all exposed silicon surfaces.

Referring to FIG. 16A, the silicon wafer 200 is subjected to an elevated temperature in an oxidizing environment to grow a layer or film of silicon dioxide 244 on all silicon surfaces to a thickness of approximately up to 3 $\mu$m. The silicon dioxide layer serves as an electrical insulating layer. Silicon nitride 246 is further deposited as shown in FIG. 16B using low pressure chemical vapor deposition (LPCVD) to provide a conformal coating of silicon nitride on all surfaces up to 2 $\mu$m in thickness. LPCVD silicon nitride also provides further electrical insulation and a fluid barrier that prevents fluids and ions contained therein that are introduced to the electrospray device from causing an electrical connection between the fluid the silicon substrate 200. This allows for the independent application of a potential voltage to a fluid and the substrate with this electrospray device to generate the high electric field at the nozzle tip required for successful nanoelectrospray of fluids from microchip devices.

Figure 16C:
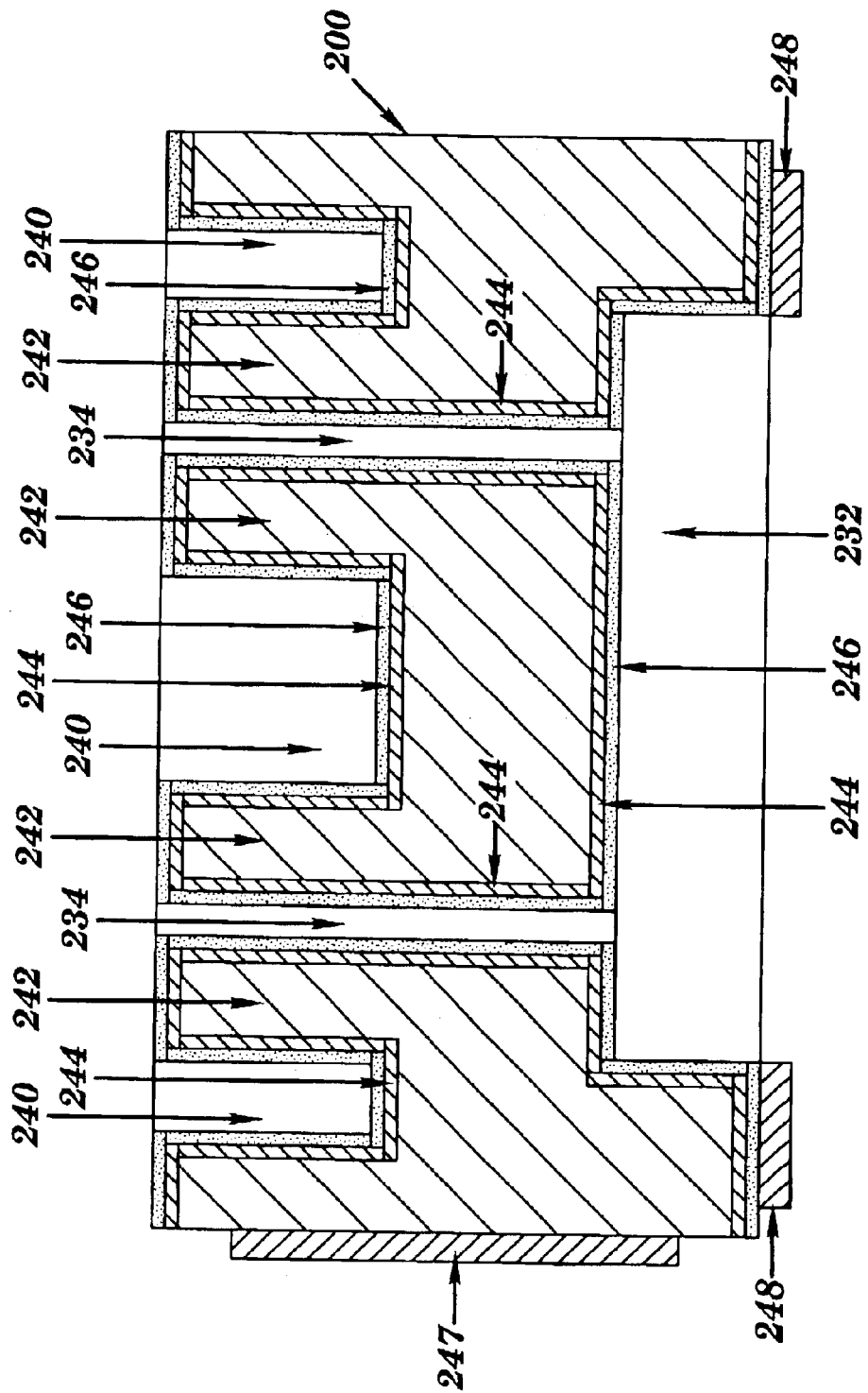
FIG. 16C is a cross-sectional view of a silicon substrate 200 showing deposition of layers of conductive metal 247, 248.

After fabrication of multiple electrospray devices on a single silicon substrate, the substrate can be diced or cut into individual devices. This exposes a portion of the silicon substrate 200 as shown in the cross-sectional view of FIG. 16C on which a layer of conductive metal 247 is deposited, which serves as the substrate electrode. A layer of conductive metal 248 is deposited on the silicon nitride layer of the reservoir side, which serves as the fluid electrode.

All silicon surfaces are oxidized to form silicon dioxide with a thickness that is controllable through choice of temperature and time of oxidation. All silicon dioxide surfaces are LPCVD coated with silicon nitride. The final thickness of the silicon dioxide and silicon nitride can be selected to provide the desired degree of electrical isolation in the device. A thicker layer of silicon dioxide and silicon nitride provides a greater resistance to electrical breakdown.

In situ Preparation of a Porous Polymer Monolith within a Microchip

Figure 17A:
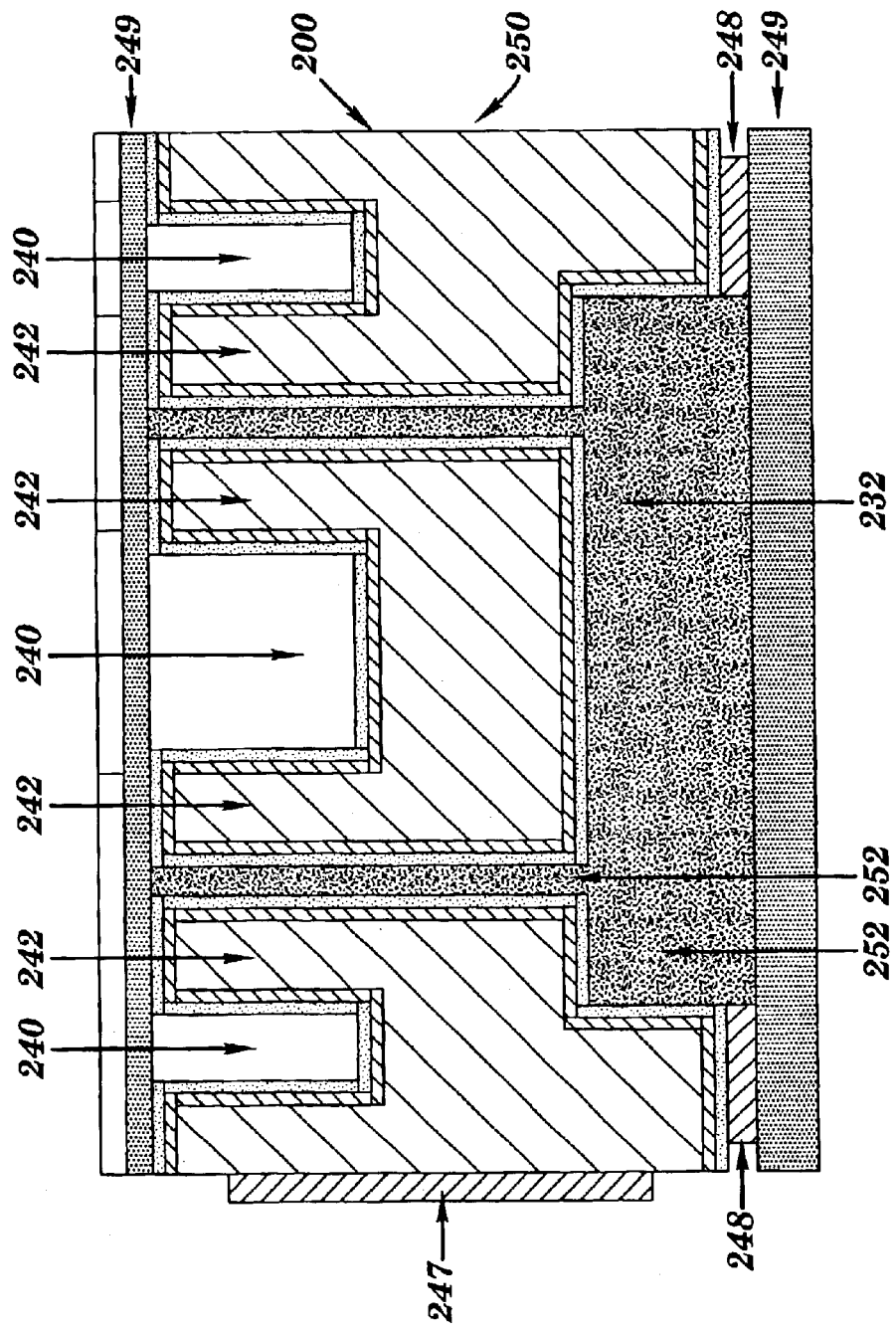
FIG. 17A is a cross-sectional view of a silicon substrate 200 showing the reservoir 232 and through-wafer channels 242 filled with a polymerizable solution 252. The polymerizable solution 252 is contained within the device with coverplates 248.
Figure 17B:
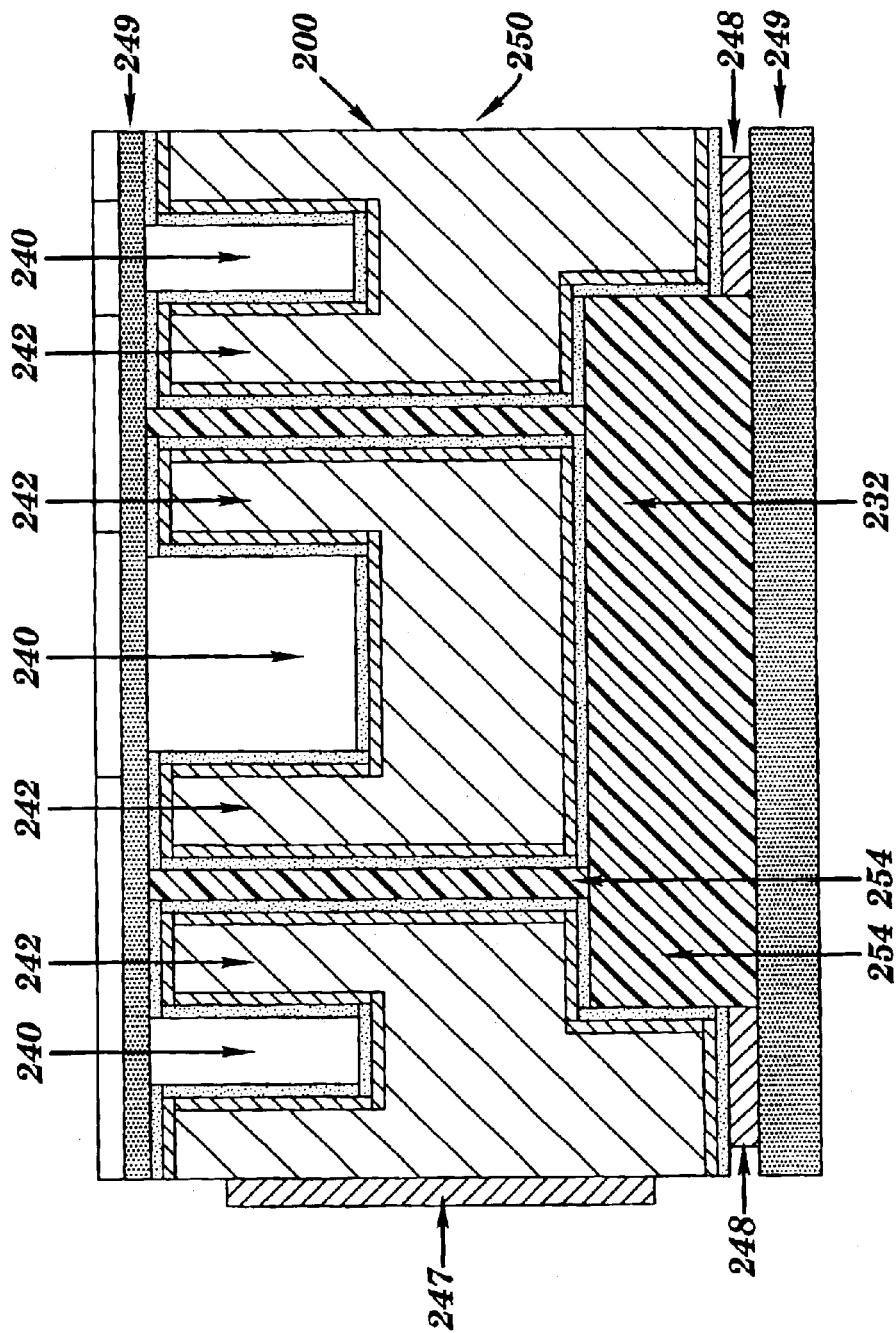
FIG. 17B is a cross-sectional view of a silicon substrate 200 showing the reservoir 232 and through-wafer channels 242 filled with polymer monolith 254.

The following is a general procedure for in situ preparation of a porous polymer monolith within the through-wafer channels and/or reservoir of a microchip electrospray device of the present invention. FIGS. 17A–17B are used as illustration of these basic steps. A cleaned silicon substrate 200 is placed within a container along with a mixture 252 of monomers, porogens and initiator. Suitable monomers include styrene, acrylic acid and its esters, methacrylic acid and its esters, vinyl pyridine, maleate, vinylester, vinyl ether, and vinylalcohol derivatives, crosslinked with divinylbenzene, ethylene dimethacrylate or diacrylate, diethylene glycol dimethacrylate or diacrylate, divinylpyridine, bis-N-vinyl-2-pyrrolidone, N,N-methylene-bisacrylamide or bismethacrylamide, or trimethylolpropane trimethacrylate. Porogens include suitable solvents compatible with the polymerization process of the present invention. A compatible porogen solubilizes the monomer but not the polymer to create pores in the polymerized material. The system is purged with nitrogen to degas the mixture and remove excess oxygen. A coverplate 249 is placed on each side of the substrate to seal the mixture within the reservoirs 232 and through-substrate channels 234. The system is heated to a temperature suitable for polymerization of the mixture or is polymerized using UV light if a UV sensitive initiator is used to form the integrated device containing polymer monolith 254, as shown in FIG. 17B. The coverplates 249 are removed.

Figure 18:
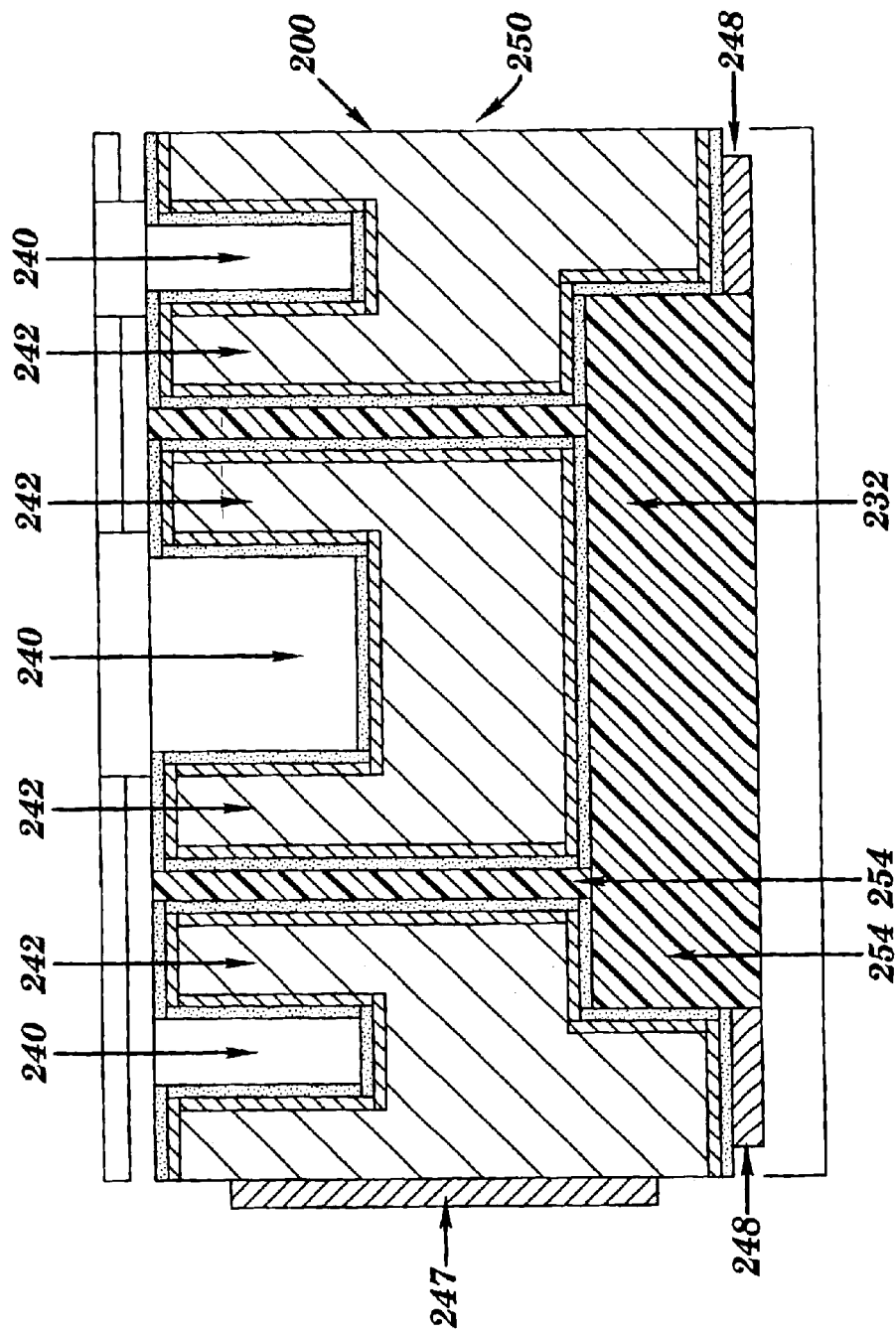
FIG. 18 is a cross-sectional view of a two nozzle polymer monolith/electrospray device of the present invention 250 showing metal deposition of electrode 256 on silicon substrate 200.

Alternately, after fabrication of multiple polymer monolith-electrospray devices on a single silicon wafer, the wafer can be diced or cut into individual devices. This exposes a portion of the silicon substrate 200 as shown in the cross-sectional view of FIG. 18 on which a layer of conductive metal 247 can be deposited using well known thermal evaporation and metal deposition techniques.

The fabrication method confers superior mechanical stability to the fabricated electrospray device by etching the features of the electrospray device from a monocrystalline silicon substrate without any need for assembly. The alignment scheme allows for nozzle walls of less than 2 µm and nozzle outer diameters down to 5 µm to be fabricated reproducibly. Further, the lateral extent and shape of the recessed annular region can be controlled independently of its depth. The depth of the recessed annular region also determines the nozzle height and is determined by the extent of etch on the nozzle side of the substrate.

An advantage of the fabrication process described herein is that the process simplifies the alignment of the through-wafer channels and the recessed annular region. This allows the fabrication of smaller nozzles with greater ease without any complex alignment of masks. Dimensions of the through channel, such as the aspect ratio (i.e. depth to width), can be reliably and reproducibly limited and controlled.

Figure 19A:
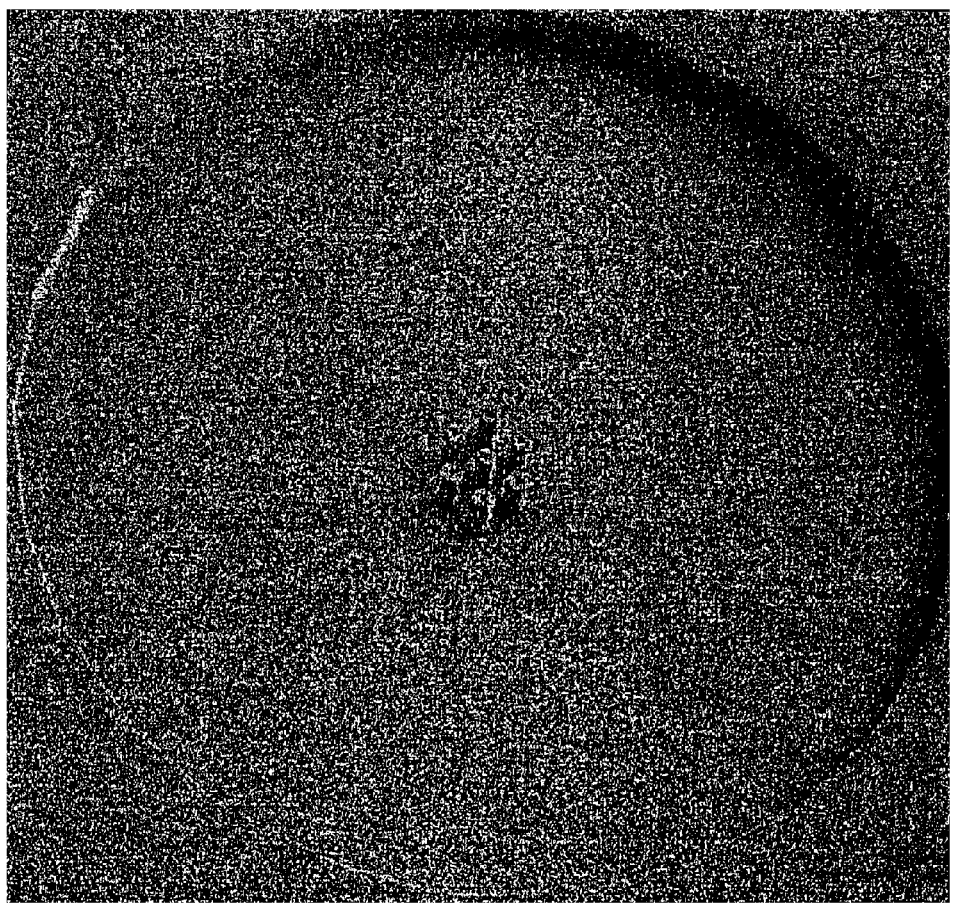
FIGS. 19A and 19B show a perspective view of scanning electron micrograph images of a multi-nozzle device fabricated in accordance with the present invention.
Figure 19B:
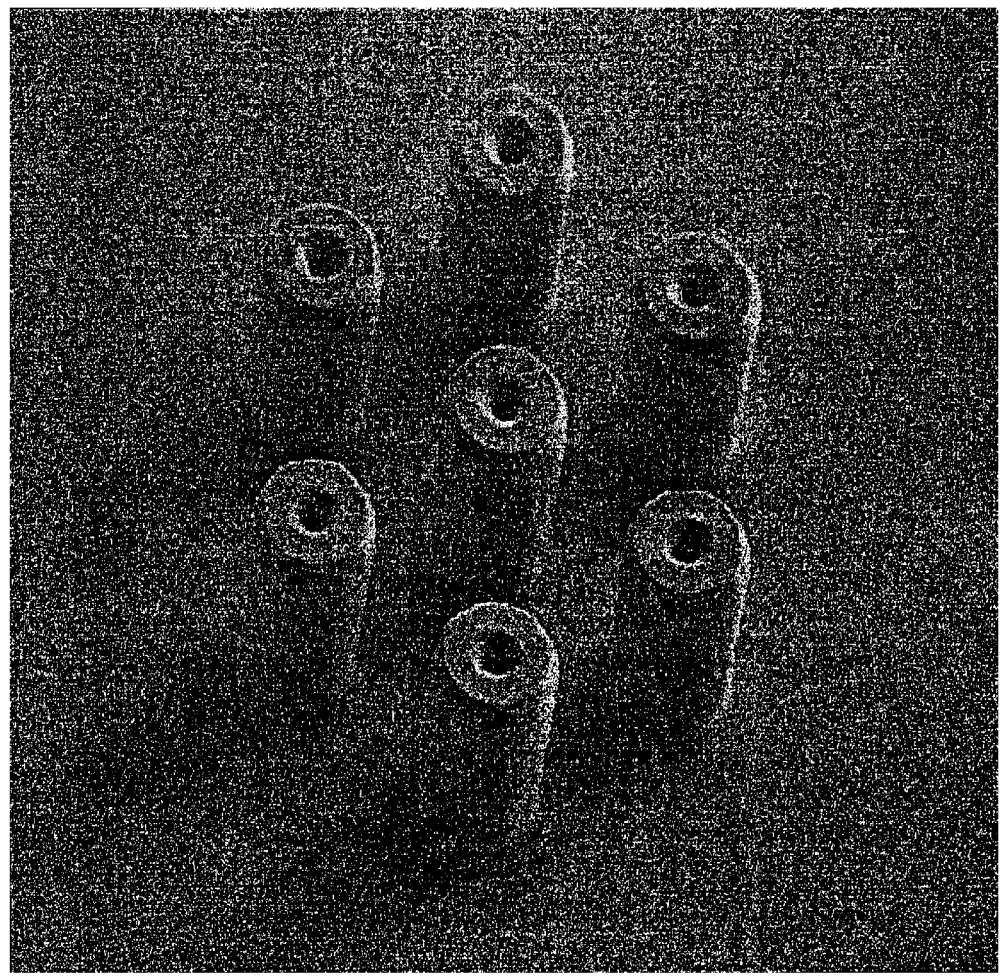

FIGS. 19A and 19B show a perspective view of scanning electron micrograph images of a multi-nozzle device fabricated in accordance with the present invention. The nozzles have a 20 µm outer diameter and an 8 µm inner diameter. The pitch, which is the nozzle center to nozzle center spacing of the nozzles is 50 µm.

The above described fabrication sequences for the electrospray device can be easily adapted to and are applicable for the simultaneous fabrication of a single monolithic system comprising multiple electrospray devices including multiple channels and/or multiple ejection nozzles embodied in a single monolithic substrate. Further, the processing steps may be modified to fabricate similar or different electrospray devices merely by, for example, modifying the layout design and/or by changing the polarity of the photomask and utilizing negative-working photoresist rather than utilizing positive-working photoresist.

Interface of a Multi-System Chip to a Mass Spectrometer

Arrays of separation-electrospray nozzles on a multi-system chip may be interfaced with a sampling orifice of a mass spectrometer by positioning the nozzles near the sampling orifice. The tight configuration of electrospray nozzles allows the positioning thereof in close proximity to the sampling orifice of a mass spectrometer.

A multi-system chip may be manipulated relative to the ion sampling orifice to position one or more of the nozzles for electrospray near the sampling orifice. Appropriate voltage(s) may then be applied to the one or more of the nozzles for electrospray.

Separation Block

The present invention also relates to a stackable separation block for use in effecting chromatographic separation of multiple samples. The separation block or stack of multiple separation blocks can be used alone or in combination with an electrospray device. The separation block can be made from any suitable material, preferably by conventional injection molding techniques. Each separation block has an array of a plurality of separation through-substrate channels. The multiple separation channels can be provided in an array having a spacing between adjacent channels and arrays having a density of channels corresponding to that of the entrance orifices of the arrays of multiple electrospray devices noted above. The separation material can be any material suitable for effecting a chromatographic separation of analytes, including polymer monolith, non-monolith polymer particles, particles containing a stationary phase, silica particles, non-porous silica, silica particles encapsulated in a polymer matrix, and the like. Stationary phase particles typically include from about 1 to about 60 µm, more preferably from about 1 to about 5 µm, most preferably about 1 to about 3 µm particle diameters coated with a stationary phase material. Separation particles can be retained in the channels by use of frits. The polymer monolith material can be fabricated in situ in accordance with the techniques noted above. Preferably, each channel of a particular block is filled with the same separation material or material having the same separation characteristics. The separation blocks can be used for sample preparation, as well as sample separation with or without integration with a microchip electrospray device.

Different chromatographic separations can be accomplished by stacking multiple blocks having different separation characteristics from one another. For example, the study of a proteome may involve the analysis of complex mixtures of up to several thousand different proteins within a sample. Analysis of these complex mixtures requires a multi-dimensional separation of the components of the mixture in order to identify and quantify the levels of the specific proteins. 2-dimensional ("2D") liquid chromatography ("LC") separations can be accomplished using multiple stacked separation blocks wherein the first block contains an LC separation phase based on ion exchange (strong cation exchange) or size exclusion separation modes. The second separation block contains a separation phase based on a reversed phase separation mode. In the case of ion exchange, a complex protein sample may be separated using an increasing salt concentration in the elution buffer over time. By performing a salt gradient in a stepwise method, for example, fractionation of complex mixtures from the first phase being an ion exchange phase to a second phase being a reversed phase provides for a 2D separation of the sample. Further combining this separation with mass spectrometry/mass spectrometry provides for 2 additional dimensions of separation based on mass/charge ratio.

FIG. 20A shows two blocks stacked one on top of the other. A sample is delivered to a plurality of separation channels 8 in a first separation block 1 at the entrance orifices 5. The sample may be delivered via a delivery device such as a conduit or from an exit orifice of an upstream separation block, or the like. The channel 8 is filled with a polymer monolith 3 for chromatographic separation of the sample. The sample travels through the separation channels 8 of the separation block 1 and is delivered at the interface 7 to the corresponding entrance orifices 5 of the channels 8 of a second separation block 2 which can be filled with a polymer monolith 4 having the same or different separation characteristics as that of the first separation block 1. The sample is eluted through exit orifices 6 to a fluid receiving device. The fluid receiving device can be a fluid control device, an electrospray device, a detection device, or the like. The fluid control device can be used to adjust the pressure of the sample stream by, for example, applying a positive pressure at one end or a negative pressure at the other end. For example, in a proteomics sample array a first separation device having an ion exchange polymer monolith can be stacked on top of a second separation device having an organic solvent separation polymer monolith coupled to a mass spectrometer.

Figure 20B:
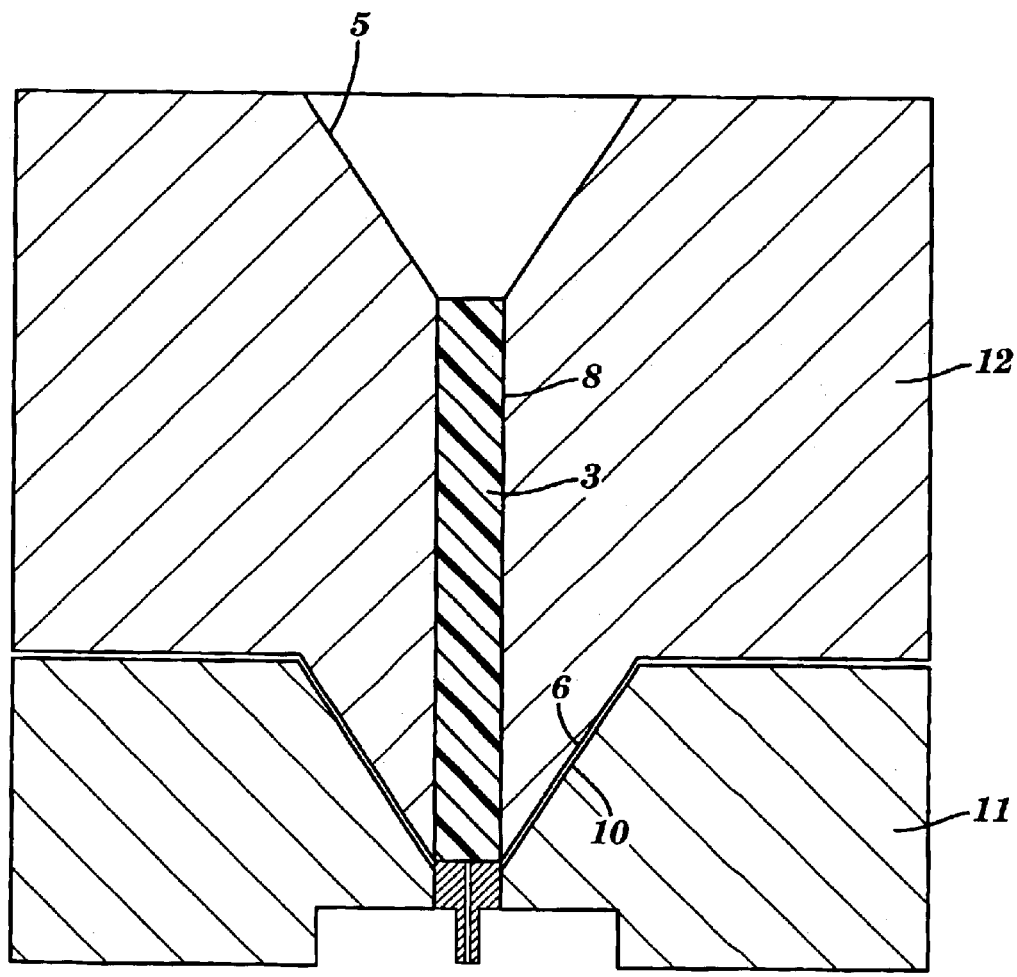
FIG. 20B shows a separation block having a separation channel filled with a porous polymeric material stacked on an electrospray device.

The separation characteristics of the polymer separation block of the present invention can be enhanced by coupling multiple blocks, such as in a stacked arrangement, together upstream of an electrospray chip. Several structural features of the blocks enhance the ability to couple multiple blocks together and couple to an electrospray chip. As can be seen in FIG. 20A, the entrance orifice 5 of the separation block 2 can be designed in the shape of a well such that it is compatible with the exit orifice 6 of the corresponding separation block 1 or, the exit orifice 6 of the separation block 12 can be mated with the entrance orifice 10 of an electrospray device 11, as shown in FIG. 20B. These features facilitate easy alignment and coupling of one block to another block and/or to a through-substrate electrospray device. They are also useful for the alignment and supporting of a gasket material 9, as shown in FIG. 20A, between the blocks or between the block and the electrospray device (not shown). The gasket can aid in preventing cross-contamination and leakage from one separation channel to another separation channel of adjacent blocks or adjacent electrospray chip device.

Accordingly, the sample can be transferred from one block to another to effect chromatographic fractionation from one block to one or more blocks and can also be coupled to the electrospray device of the present invention for further separation and sample preparation and/or to a detection device for spectroscopic detection such as, UV absorbance, laser induced fluorescence, and evaporative light scattering.

The polymer monolith can be prepared in accordance with the procedures noted above with respect to the in situ preparation of a porous polymer monolith within the through-substrate channels and/or reservoir of a microchip electrospray device of the present invention. In a preferred formulation of the present invention the polymer monolith of the separation block is formed from one or two monovinyl monomers with the addition of a cross-linker. Preferred monovinyl monomers include styrene, vinylbenzyl chloride, vinylacetate, alkyl methacrylates and glycidyl methacrylates. Preferred cross-linkers include divinyl monomers, such as divinylbenzene, ethyleleglycol and dimethacrylete. The preferred formulation has a 20–50 volume/volume percent cross-linker in the monomer mixture.

The preferred initiators in an 8–24 hour reaction under heating with a purge of an inert gas include 2'2-azobisisobutyronitrile (0.2–0.5 w/v %: 45–75° C.); and benzoyl peroxide (0.2–0.5% w/v %; 60–80° C.). For photo polymerization the above initiators can also be used as photo sensitized initiators at UV wavelengths of 2000–4000 Å.

The preferred porogen is a mixture of a relatively less polar organic solvent, for example an alcohol, such as 1-propanol and a more polar organic solvent, such as formamide. Preferably, the monomer to porogen ratio is about 40 to about 60 v/v.

The finished monolith pore size is preferably from 1 to 3 microns and the monolith has a porosity from 45 to 65 v/v %. The separation channel is typically less than ten centimeters, preferably less than five centimeters, more preferably less than three centimeters, more preferably less than one centimeter and most preferably less than five millimeters. Separation channels having an inner diameter of less than one millimeter are preferred, more preferably less than 0.5 millimeters, more preferably less than 0.3 millimeters, more preferably less than 0.2 millimeters, and most preferably less than 0.1 millimeter.

The chromatographic resolution of the polymer monolith is significantly independent of the flow rate of the mobile phase. The quality of the separation does not change when increasing the flow rate so long as the same gradient volume is maintained. For example, E. C. Peters et al. in Rigid Macroporous Polymer Monoliths, Advanced Materials, 1999, 11, No. 14, which is herein incorporated by reference in its entirety, disclose the separation of three proteins on a poly (styrene-co-divinylenzene) monolithic column at flow rates of 5 and 25 mL/min. using a column having a 50×8 mm inner diameter where the mobile phase is a linear gradient from 20 to 60 percent acetonitrile in water. By increasing the flow rate from 5 to 25 mL per minute, the time required for the separation is reduced from around four minutes to less than one minute. The polymer separation blocks formulated in accordance with the present invention, when used in combination with a through-substrate multi-nozzle array electrospray device, optimizes the higher flow rates achievable with the multi-nozzle array which can be used to increase sample analysis speed.

In accordance with the present invention, through-substrate separation is integrated with high density arrays of electrospray devices, which also have through-substrate electrospray channels. In this manner, high density arrays of through-substrate separation channels can be oriented parallel to corresponding electrospray channels of high density arrays of electrospray devices. Such configurations achieve separation/detection density capabilities and flow through volumes not possible with conventional technology. Through-substrate channels are characterized by channels extending from one surface through the width of the substrate to the other surface. Through-substrate channels can be distinguished from 3-sided or open channels which are typically etched on the surface of the substrate. Open channels are typically closed by placing a cover plate over the surface channels of the substrate.

Sample detection from multiple electrospray nozzles can be achieved from the sequential or simultaneous spraying of an array of electrospray nozzles. For sequential spraying, a detector such as a mass spectrometer can be placed in communication with a first electrospray of from, for example, an array of 8 electrospray devices. The electrospray is passed into the inlet of the mass spectrometer and analytes present in the electrospray are detected. The array of nozzles are then moved to place a second one of the 8 devices in communication with the mass spectrometer. Analytes present in the second electrospray are detected in a similar manner. The array of electrospray devices are moved in desired sequence until all electrosprays are analyzed.

For simultaneous spraying, fluid is simultaneously sprayed through each of the nozzles in the array. The analytes are analyzed by sweeping the detector, for example a mass spectrometer, across the face of the nozzle surface. The nozzles are spaced apart in a manner so as to readily correlate the detected sample with each of the corresponding nozzle samples. Processing capacity and time can thus be increased over that compared to the previous method. Alternately, when it is not necessary to distinguish between each nozzle spray, multiple electrosprays from the nozzle array can be simultaneously sprayed and detected to further increase processing capacity.

Accordingly, through-substrate separation integrated with through-substrate electrospray formatted in a high density array system in accordance with the present invention achieves an increased flow rate, volume, and density detection capabilities previously unachievable in the art.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of producing an electrospray device comprising:

providing a substrate having opposed first and second surfaces, at least the first surface coated with a photoresist over an etch-resistant material;

exposing the photoresist on the first surface to an image to form a pattern in the form of at least one ring on the first surface;

removing the exposed photoresist on the first surface which is outside and inside the at least one ring to form an annular portion;

removing the etch-resistant material from the first surface of the substrate where the exposed photoresist was removed to form holes in the etch-resistant material;

optionally, removing all photoresist remaining on the first surface;

exposing the photoresist on the second surface to an image to from a pattern circumscribing extensions of the at least one ring formed in the etch-resistant material of the first surface;

removing the exposed photoresist on the second surface;

removing the etch-resistant material on the second surface where the photoresist was removed;

removing material from the substrate coincident with where the etch-resistant material on the second surface was removed to form a reservoir extending partially into the substrate;

optionally, removing the remaining photoresist on the second surface;

coating the second surface with an etch-resistant material;

coating the first surface with a second coating of photoresist;

exposing the second coating of photoresist within the at least ring to an image;

removing the exposed second coating of photoresist from within the at least one ring to form at least one hole;

removing material from the substrate coincident with the at least one hole in the second layer of photoresist on the first surface to form at least one passage extending through the second layer of photoresist on the first surface and into the substrate to the extent needed to reach the etch-resistant material coating the reservoir;

removing photoresist from at least the first surface;

applying an etch-resistant layer to all exposed surfaces of the substrate;

removing the etch-resistant layer from the first surface that is around the at least one ring;

removing material from the substrate exposed by the removed etch-resistant layer around the at least one ring to define at least one nozzle on the first surface;

removing from the substrate at least the etch-resistant material coating the reservoir;

applying an etch-resistant material to all surfaces of the substrate;

filling at least one of the reservoir and the at least one passage with a polymerizable material; and polymerizing the polymerizable material.

2. The method according to claim 1, wherein the substrate is made from silicon and the etch-resistant material is silicon dioxide.

3. The method according to claim 1, further comprising:

applying a silicon nitride layer over all surfaces after said applying an etch-resistant material to all uncoated portions of the substrate.

4. The method according to claim 1, wherein the polymerizable material comprises styrene, acrylic acid and its esters, methacrylic acid and it esters, vinyl pyridine, maleate, vinylester, vinyl ether, and vinylalcohol derivatives, crosslinked with divinylbenzene, ethylene dimethacrylate or diacrylate, diethylene glycol dimethacrylate or diacrylate, divinylpyridine, bis-N-vinyl-2-pyrrolidone, N,N-methylene-bisacrylamide or bismethacrylamide, or trimethylolpropane trimethacrylate.

5. The method according to claim 4, wherein the polymerizable material further comprises a porogen and an initiator.

6. The method according to claim 1, wherein at least one passage is filled with the polymerizable material.

7. The method according to claim 1, wherein the reservoir is filled with the polymerizable material.

8. The method according to claim 1, wherein the reservoir and at least one passage are filled with the polymerizable material.

9. The method according to claim 1, wherein multiple passages are filled with the polymerizable material.

* * * * *